United States Patent [19]

Coli

[11] 4,315,309
[45] Feb. 9, 1982

[54] INTEGRATED MEDICAL TEST DATA STORAGE AND RETRIEVAL SYSTEM

[76] Inventor: Robert D. Coli, 470 Tollgate Rd., Warwick, R.I. 02886

[21] Appl. No.: 51,714

[22] Filed: Jun. 25, 1979

[51] Int. Cl.³ .............................................. G06F 15/42
[52] U.S. Cl. .................................... 364/200; 364/300
[58] Field of Search ... 364/200 MS File, 900 MS File, 364/415, 300; 128/2 R

[56] References Cited

U.S. PATENT DOCUMENTS

| | | | |
|---|---|---|---|
| 3,839,708 | 10/1974 | Bredesen et al. | 364/900 |
| 3,872,448 | 3/1975 | Mitchell | 364/200 |
| 3,898,373 | 8/1975 | Walsh | 364/200 |
| 3,970,996 | 7/1976 | Yasaka et al. | 364/900 |
| 4,053,951 | 10/1977 | Hudspeth et al. | 364/415 |
| 4,130,881 | 12/1978 | Haessler et al. | 364/900 |

OTHER PUBLICATIONS

Hadley et al., "Experience with Simplified . . . Patients", pp. 348–357, 1979 IEEE.

Primary Examiner—Raulfe B. Zache
Attorney, Agent, or Firm—Sixbey, Friedman & Leedom

[57] ABSTRACT

A patient report generating system for receiving, storing and reporting medical test data for an entire patient population by periodically forming individual patient reports containing all test results for each patient for the total time period during which the patient has been a member of the patient population. Each report is organized to present the cumulative test data in a highly compact pattern of data packages wherein each data package includes only results of tests making up a particular organ system disease related subset of tests. The disclosed apparatus includes a data entry terminal, such as a keyboard input, for generating a digital electrical field for each test which field identifies the test, the test results, the date of the test and the patient. Also included is a random access memory for receiving and storing all signal fields and a high speed printer for forming a hard copy of the patient report from the stored data. To insure that each patient report is formatted identically with all other reports, the system includes a control memory for generating report and data package formatting signals which cause the printer to present the test data in consistent orthogonally arranged data packages wherein the test data within each data package is organized to assist the clinician to assimilate and understand the test data in the least possible time.

30 Claims, 39 Drawing Figures

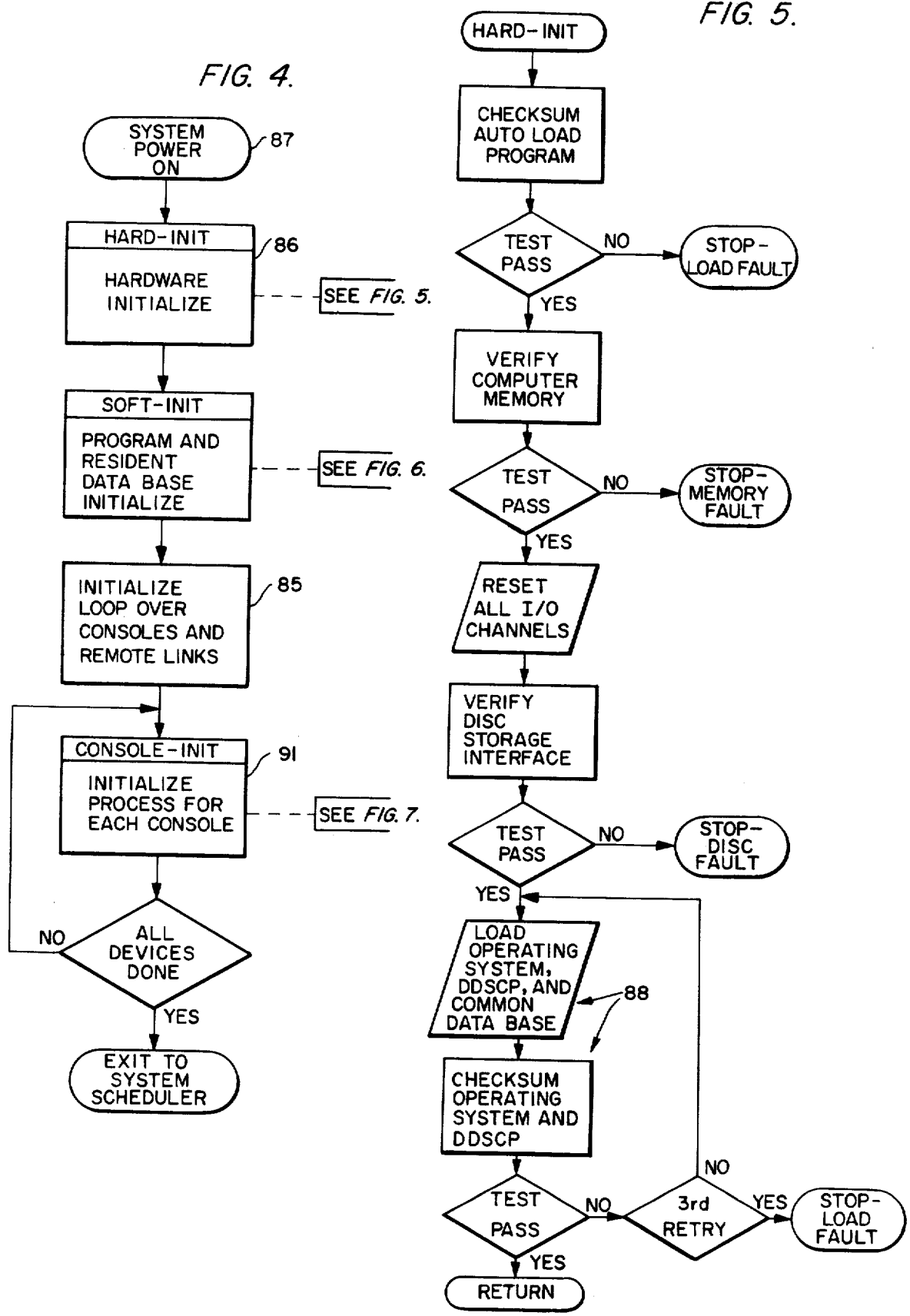

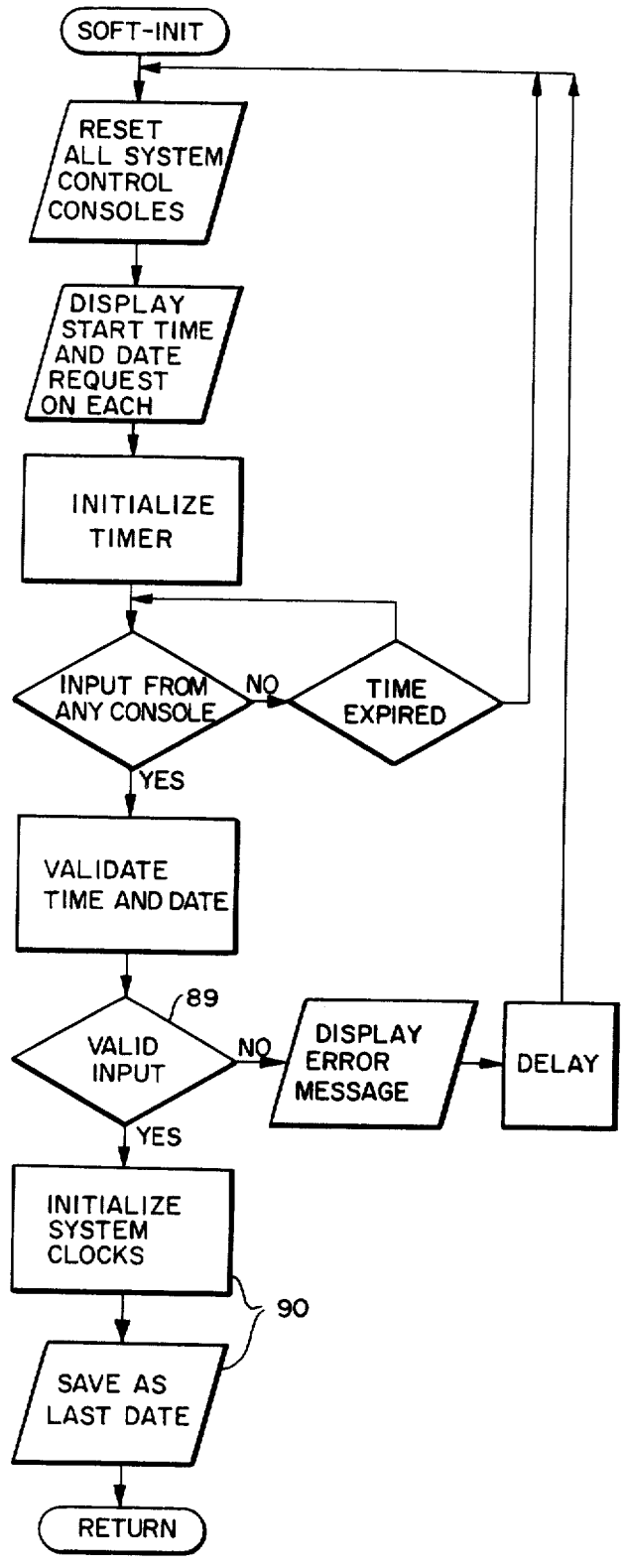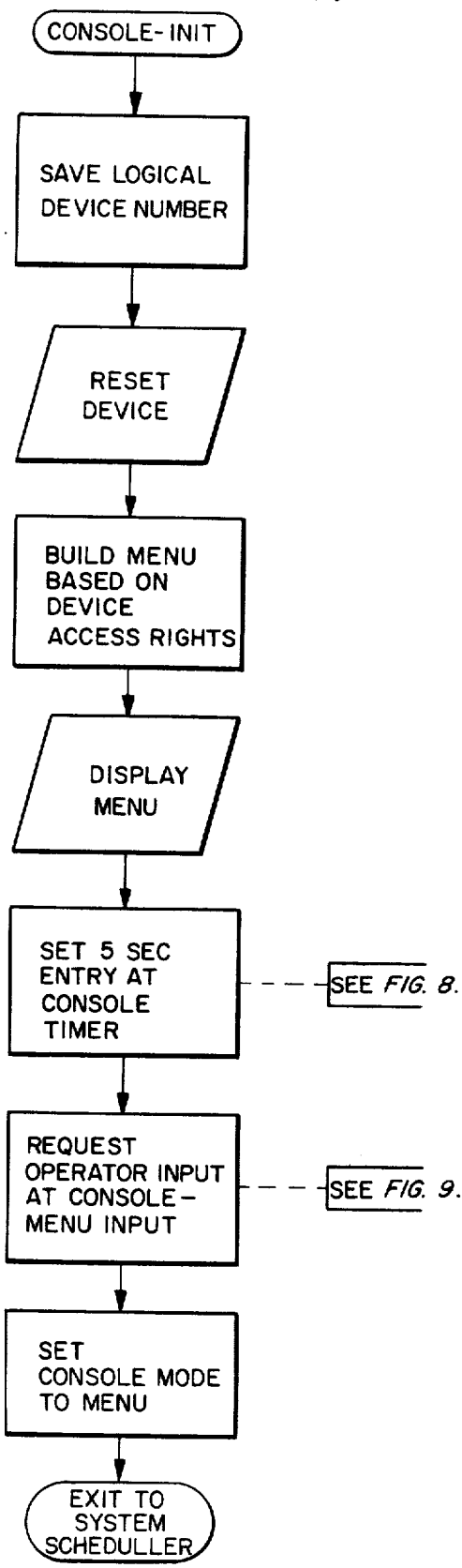

INTEGRATED MEDICAL TEST DATA STORAGE AND RETRIEVAL SYSTEM

TECHNICAL FIELD

This invention relates to method and apparatus for generating, storing and reporting medical test data on a given patient population such as the patients within a hospital. In particular the invention is directed to the generation and storage of hospital laboratory test results and to the formation of individual patient reports using the stored test results.

BACKGROUND ART

Medical knowledge in the areas of both diagnosis and treatment is now so advanced that good health care, in the aggregate, is as much a function of society's ability to pay as it is a function of the state of knowledge about proper health care. This fact has vastly increased the pessure on health care planners and administrators to seek greater cost effectiveness in health care delivery. One obvious technique has been to employ computerized data handling.

A variety of computerized data handling systems exist ranging from a computer assisted system for taking patient medical histories as disclosed in U.S. Pat. No. 4,130,881 to extremely sophisticated systems such as that recently instituted in a California hospital in which virtually all of the data handling functions within the hospital were computerized, 123 Cong. Rec. (June 10, 1977) (Remarks of Congressman Ottinger). A limited degree of success in reducing hospital costs has been achieved by the use of these systems. However, health care costs have continued to rise at a rate which far exceeds the rate of increase in the cost of living. Annual amounts spent for health care now account for about 10 percent of the Gross National Product and could easily exceed 229 billion dollars by 1981, double the amount spent in 1976. Prior attempts at computerization of data handling functions within the health care industry have generally centered around the use of electronic data handling as a mere substitution for normal recordation and transmission of information. While such attempts are certainly useful insofar as they go, they have failed to capitalize on the immense power of modern electronic data handling systems to sift, categorize and format information in a way which measurably improves the efficiency of individual medical practitioners.

One explanation for lack of success in health care cost containment despite wide spread use of computerized data handling is the fact that the amount of potentially relevant data has been expanding enormously. A careful medical practitioner thus requires vastly greater amounts of such information as laboratory test results, diagnostic information and pharmacological alternatives for treatment than was true only a decade ago when computers were first introduced. For example, in the last decade the number of available diagnostic laboratory tests has doubled and heretofore unknown diagnostic procedures are now commonly performed. The body of medical knowledge has undergone such an exponential increase that decisions regarding the best medical treatment can be reached only after careful consideration of a vast quantity of input. Generation of this input is extremely expensive and often turns out subsequently to have been unnecessary.

Further compounding this problem is the fact that health care planners and administrators are now calling upon the individual physician to be cost conscious regarding each of his diagnostic and treatment decisions. In response to this request, some medical schools have now integrated basic questions of cost with the standard considerations of diagnosis and treatment in their curricula.

This emphasis on cost containment has been stressed further by professional organizations such as the American Medical Association and the American College of Physicians as critical to making proper treatment decisions. Physicians are now being urged to become cost conscious by programs such as those designed to assess medical knowledge in preparation for the fulfillment of licensing and certification requirements. These programs evaluate physician decisions requesting tests and procedures in the diagnosis and management of given clinical conditions on the basis of cost to the patient, as well as such traditional factors as risk.

Physicians are thus being asked to include a whole new world of information on top of an already exponentially expanding body of conventional medical knowledge. Without new tools to provide assistance it is unrealistic to expect the majority of practicing physicians to contribute to effective cost reduction in the delivery of health services. Some hospitals have made attempts in this direction by instituting partially or fully computerized systems for presenting the results of diagnostic tests. While the available systems have helped physicians provide patients with the best available medical care, the information they present has not been organized with any conscious effort to save the physician's time and reduce costs. Accordingly, these systems do not enable the physician to assimilate significant information in a minimum amount of time so that information can be utilized optimally in patient care and management.

The greatest volume of information generated from diagnostic tests and procedures confronting the physician comes from those tests and procedures most often performed on hospitalized patients. These are most likely to be chemical and microbiological laboratory analyses of blood and other body fluids, x-rays, and electrocardiograms. All other diagnostic procedures, such as ultrasound examinations and isotopic scans of body organs, tend to be performed much less frequently. Of all of these diagnostic tests and procedures, the data generated by laboratory tests on blood is the most profuse and requires the most time for the physician to interpret and apply in making patient management decisions. For example, about one million of the 1.1 million diagnostic tests and procedures performed in one medium sized hospital, Kent County Hospital, Warwick, R.I., during one year were laboratory analyses of patients' blood. The data from these blood tests is quite diverse in nature and is quickly accumulated in massive amounts in patient records, especially if the hospital stay is a long one or the patient's clinical condition requires close monitoring of his blood chemistry. Unless this profusion of information is organized and presented in a format so that information regarding patient management is readily available, valuable physician time will be wasted in sifting through the mass of data to find the most significant test results.

In a large number of hospitals today, laboratory blood test results are entered manually by laboratory personnel on slips of paper approximately 7 inches by 3 inches in size including information regarding several sometimes unrelated tests which are then sent to the hospital floor and pasted in the patient's record by floor personnel. Each time a test is repeated, another slip reporting the results must be added to the petient's record. The physician who must utilize these blood test results to make a diagnosis, prescribe treatment and otherwise provide patient care is confronted with a confusing array of clinically unrelated data which can require considerable time to organize and assimilate before it can be used in any meaningful way. In the case of a patient whose clinical condition requires a long hospital stay or frequent laboratory blood analyses, the numbers of slips of paper containing test results can increase at a phenomenal rate. As the number of tests performed and, hence, the number of slips of paper increases, it becomes extremely difficult if not impossible for the physician to follow clearly the results of important tests and to determine the correctness of a diagnosis or the effectiveness of a prescribed course of treatment and therapy. In hospitals where such a system of presenting laboratory test data is in effect medical students or nurses are often required to make charts organizing the data so that the physician can make some sense out of it and devote more time to the patient. The time and cost consuming aspects of such a system are clear. It is neither cost effective nor beneficial to the quality of patient care for physicians to spend their time performing manual information processing tasks, especially when computer assisted methods of reporting diagnostic information are available.

However, computer assisted methods of reporting diagnostic information do not necessarily result in time savings to the physicians or other end users of the information. U.S. Pat. No. 4,053,951 discloses a system for recording and reproducing medical data which generates an individual patient report printout each time the data is recorded, which could be several times a day. The resulting multiplicity of individual slips are then compiled in the patient's chart in much the same way as the manual laboratory slips described above. While this system represents an improvement over previously used noncomputer assisted systems, the data is cumbersome to use and requires more time for evaluation than is desirable with an automated system.

While some of the automated data display systems presently in use have attempted to organize at least portions of the patient test data reports in some semblance of a relationship to recognized clinical conditions, none of the existing automated systems has fully integrated the relationship between diagnostic tests and the organ system related clinical conditions in which their use is indicated. An additional drawback presented by prior art systems producing hard copy reports of individual patient test data is the failure of such systems to present the test data in a truly cumulative form which enables the clinician to review at a glance a chronological listing of all the results of a particular test. Some hard copy reports display the data on which tests are performed across the top of the page and list the individual tests down the left margin, thus limiting the number of test results which can be chronologically displayed. The systems which use this format generally put four or five days worth of tests on each page of the patient test data report, which requires the end user to review many sheets of the patient report to follow the results of significant tests over the course of hospital stay which is more than four or five days in duration. Those systems which display test data across and the dates down the left margin of the patient test data report approximate more closely a truly cumulative report. However, some of these systems often print test data covering only a specified period of time on each page of the patient report. Therefore, all such reports must be saved since the information they contain will not appear in future reports.

An additional drawback of the automated systems for presenting patient test data presently in existence concerns the reference data and the way in which these systems indicate whether a test is within normal limits. Since the levels of most chemical substances in the blood depend upon the age and sex of the individual whose blood is analyzed, a truly meaningful patient test data report includes a reference range for each test which is adjusted to the age and sex of the patient. Some of the prior art systems do utilize reference ranges for which some adjustment has been made to take into account the age and sex of the patient. When this has been done, however, the pool of individuals from which the data has been drawn has not been as large as desirable to yield the best reference data.

If a test is outside the values determined to constitute the normal range, prior art systems have usually indicated this fact by printing an H or a + (for a value that is higher than the normal range) or an L or a − (for a value that is below the normal range). The end user of the patient test data report must then determine the significance of a test result outside the normal range. In the case of most commonly used diagnostic tests, the physician performs this task mentally in a minute or so based on his expertise. In the case of a diagnostic test or procedure which is used infrequently or when a consulting physician with a different area of expertise is called in, the indication of a test result outside normal ranges, while quite helpful, may necessitate the expenditure of considerable time to ascertain the significance of the suspect test result so that the information can be used correctly and effectively in the management of the patient's condition. Although such information has been provided as part of the raw data received from professional laboratory reports, no prior integrated hospital reporting system has been designed to incorporate such information. One known hospital system has utilized explanatory footnotes to describe, to a limited extent, abnormal cellular morphology, but this information was not generated as a result of comparing out-of-range test values with an established normal reference range.

In another partially automated system, employed at The Rhode Island Hospital, Providence, R.I., tests are grouped in one data package which relate to renal function and acid-base balance and in another some of the commonly used tests relating to liver function, both of which are clinically relevant data packages. However, the third and fourth data packages in this system do not share the same clinical orientation. the third combines indicia of liver function with those of parathyroid function and fat metabolism, while the fourth mixes therapeutic drug levels with a pancreatic function test and a metabolic test. Miscellaneous blood and urine chemistry tests are then listed randomly in a way that has no clinical orientation whatever. Normal ranges are presented with only some of the tests, the remainder being listed on a page separate from the patient test data report. In this system, however, all other diagnostic laboratory tests, including all blood tests commonly referred to as hematology tests, are reported manually on slips of paper as described above.

Still another system, which is fully automated and has been in use at Roger Williams Hospital in Providence, R.I. since 1971, presents one blood chemistry data package containing twelve separate tests in the order these tests are performed by the automatic blood analyzer operated by the hospital's laboratory. These tests are not performed in any organ system specific, clinically related order; therefore, the presentation of this data in the patient test data report does not facilitate the physician's performance of diagnostic and clinical patient management functions. Another data package produced by this system includes liver, kidney and metabolic tests arranged in a way which requires the unnecessary expenditure of valuable professional time to assimilate and interpret. Still another data package is labeled "Enzymes" and is somewhat clinically oriented in that it contains the remainder of the liver function tests not performed by the automatic analyzer. Such a data package, however, presents only a partial picture of the clinical condition to the end user of the data. This system includes an additional data package entitled "Elect:" (Electrolytes) which contains tests relating to acid-base balance, but only a single test of kidney function. This, too, presents data in a form which does not give the physician a complete picture. Other critical kidney function data which would enable the physician to evaluate acid-base balance/renal function interrelationships is buried with liver function data. Results of all other laboratory blood tests are randomly listed so that there is no logical clinical relationship between them. For example, an activated partial thromboplastin time (APPT) test, which relates to blood coagulation, is followed by a serum amylase level, which is indicative of pancreatic function. This system has also incorporated microbiological tests in the hard copy of the patient test data report. However, the format in which this information is presented is analogous to a compilation of manually printed slips since the microbiological data generated each time a body site is cultured occupies a space on the page about the size of one of the traditional manual laboratory slips. In addition, the data is not cumulative, thus requiring the physician to flip through many pages to determine, for example, if a prescribed course of antibiotic therapy is effective. A further problem encountered by the end user of the above described system is posed by the generally noncumulative nature of the entire data presentation. It accumulates all the data from certain tests for only a limited time period before reporting it in the hard copy of the patient test data report. Since this data will not appear in future reports, the page containing it must be retained to maintain a complete record. The test data report of a patient who spent four weeks in Roger Williams Hospital was over forty pages in length, and thus required a substantial amount of time for the physician to organize, assimilate, interpret and apply the information in the format generated by this system.

A third fully computerized system currently in use at the 500 bed Medical Center Hospital of Vermont, Burlington, Vt., presents in its patient test data report two data packages, one essentially complete and one missing an important element, which bear some clinical relationship to each other. The remainder of the test data is listed below these data packages. Unlike other systems which have listed test data vertically down the page, these are listed in somewhat of a related way. For example, the serum creatinine and BUN results, both important indicators of renal function, are set forth together. However, as a whole, the system is not designed to enable the end user of the information to focus on organ system related conditions in the most efficient way. Moreover, since the data in this system is cumulative for only seven days, the potential exists for a massive accumulation of data during a long hospital stay. This fact, coupled with the absence of a well-defined organ system relationship of the data, does not facilitate patient management for the clinician.

The patient test data report of still another fully computerized system recently instituted at Holyoke Hospital, Holyoke, Mass., is an improvement on the system just described in that all of the diagnostic tests are arranged in horizontal data packages so that the report is somewhat easier to follow. Two of the data packages in this system are essentially complete in that the data they present is sufficient to enable the end user to monitor a particular organ system related condition. These are data package labeled "Electrolytes -BUN- Creatinine", which contains most of the tests related to acid-base balance and renal function, and the data package labeled "Arterial Blood Gases", which includes the major information relative to changes in respiratory function. The remaining data packages provide, at best, only a partial picture of important organ system related clinical conditions. For example, the data package entitled "Enzymes" includes some of the diagnostic tests needed to diagnose, treat and follow liver dysfunction. However, to obtain a complete picture of liver function, it is necessary for the clinician to refer to a second data package which contains most of the rest of the clinically relevant information.

Only one prior art system, the patient test data reporting system offered by Burroughs Hospital Information System, is known which includes diagnostic data from other than laboratory tests in its patient test data. This system includes a concise statement of data generated from diagnostic radiology procedures in addition to the standard hematology and urinalysis data. However, the remainder of the patient test data report suffers from the same lack of orientation to clinically related conditions as the other prior art systems. For example, a blood chemistry data package generated by an automated laboratory analyzer is included under the heating of Hematology.

As can be appreciated from the above discussion, the known types of diagnostic test data presentation systems currently in effect range from those in which only some diagnostic data is reported by a computer assisted system to fully computerized presentations of information from laboratory analyses of blood and body fluids. Perhaps the most serious drawback presented by such computerized system lies in the difficulty encountered by the clinician or other end user in utilizing this information efficiently to manage patients. None of the known systems has attempted to include all known diagnostic tests and procedures within a single clinically oriented format. Moreover, none of the existing systems has organized all of the test data packages so that each data package includes tests which are diagnostic for certain organ system related medical conditions. All of the existing fully computerized systems present data from complete blood counts and differential blood counts together since most hospitals now have automated laboratory equipment which performs these laboratory tests. The patient test data report generated by these systems usually reflects the information in the order the tests are performed by this equipment. In addition, all existing fully automated systems put the standard information determined from a urinalysis in the same area of the patient test data report. Some of the existing systems have attempted to group together in data packages across the top of a page those diagnostic blood tests which are commonly ordered together. This has been attempted most often with tests which analyze the chemical composition of the blood. While grouping together those tests which are often ordered together may have some relationship to convenience, such an arrangement is not always the most clinically relevant one. No single computer assisted system has been developed which collects data from diagnostic laboratory tests and diagnostic procedures and reports it in a condensed, organized and clinically relevant form that is specifically designed to assist the clinical physician, primary end user of the data, in making a clinical diagnosis, prescribing a course of treatment or therapy consistant with the diagnosed clinical condition, and readily following the effects of the prescribed treatment or therapy on the clinical condition during the patient's hospital stay.

DISCLOSURE OF THE INVENTION

It is a general purpose of this invention to overcome the drawbacks of the prior art by providing a system for generating, storing and reporting medical test data in a manner to assist patient treatment personnel to assimilate and understand in the least possible time all of the medical test results necessary to properly diagnose and trest individual patients.

A more specific object of this invention is to provide apparatus for generating periodic cumulative patient reports superseding all previous reports and including all medical tests conducted on the patient during the time that he has been a member of a predefined patient population wherein the test results are formatted to assist in assimilation and interpretations of the reported data.

It is still another object of this invention to supplement the results contained on each patient report by providing automatically supplementary information in association with pre-defined out-of-range test results wherein the supplementary information is designed to assist the clinician to better treat the patient and to lessen overall medical costs.

The subject invention is designed to provide patient care personnel such as doctors, nurses and others with individualized patient test reports incorporating all accumulated test results wherein the results are consistently formatted in accordance with a predetermined pattern applied repeatedly to all patients existing within a patient population to thereby assist the patient care personnel in assimilating this information in the least possible time while eliminating the necessity to consider irrelevant test data which might otherwise become intermixed with that appearing in the patient report.

Still another object of this invention is to provide a system for generating electrical signals, storing the signals, and retrieving and formatting the signals to permit a high speed printer or CRT to display the formatted test results in a predetermined associative pattern having relevance to patient care personnel who must make diagnostic and treatment decisions based upon results and perceived patterns of results relating to organ system diseases.

The disclosed method and apparatus is designed to collect, organize, and consistently format relevant technical information for use by patient care personnel to assist such personnel in making not only correct medical decisions but decisions which are cost effective from the standpoint of providing the best possible care to the largest number of patients.

A still more specific object of this invention is to provide apparatus for generating, storing and reporting medical test data arranged to produce periodic cumulative patient reports organized to present test data in a manner to facilitate use of the test data by a wide variety of health care personnel including not only physicians but also nurses, students and other personnel who must assimilate and act upon the results. In particular, the apparatus is designed to generate periodic individual patient test data reports for each patient within a patient population wherein each report includes all stored test data for the particular patient for the total time period during which the patient has been a member of the patient population. Each report is organized to present the cumulative test data in a highly compact pattern of data packages with each data package including only results of tests making up a particular organ system disease related subset of tests.

Still another object of this invention is to provide method and apparatus for generating individual patient test data reports by means of a high speed printing device arranged to convert digital electrical signals representative of the type of test and of the dates and results of such tests into visually perceptible indicia appearing in an orthogonal pattern of rows and columns on a hard copy report combined with data package formatting means for generating successive data package formatting signals to cause the results of repeated performance of the same tests on the same patient to appear in a single column of a single data package and to cause the results from all tests within the corresponding subset of tests conducted on the same patient on the same date to appear in a single row of the same data package.

It is a more specific object of this invention to provide apparatus for generating patient reports of the type described above including report formatting means for generating an identical succession of report formatting electrical signals each time a patient report is produced by the high speed printer for identifying the tests and sequence of tests included in each successively formed data package and for identifying the sequence in which the data packages are to appear in each patient report.

Yet another object of this invention is to provide apparatus including a system controller connected with a high speed printer to cause the printer to form a patient report for each patient within the patient population by retrieving all data accumulated on each patient during the entire period that the patient has remained a member of the patient population and for causing the printer to form a predetermined succession of comprehensive data packages in accordance with formatting signals which cause each data package to contain a orthogonal pattern of visible indicia including the results of all tests defined by the data package which were conducted on the patient during the entire period in which the patient has remained a member of the patient population and with the visible indicia in each column representing the results of each corresponding test and for generating printer control signals which cause the printer to print the visible indicia in each column of each data package is chronological order as determined by the information stored in the system.

Another object of this invention is to provide method and apparatus for forming comprehensive patient test data reports including data packages containing not only test results pertaining to specific organ system diseases and reference level information for each test adjusted for the age and sex of the patient but also supplemental diagnostic, alternative treatment, and current cost information which is automatically generated in response to the existence of certain out-of-range test results as determined by the age and sex adjusted reference levels stored in the system.

Still other and more detailed objects of this invention will appear from a consideration of the following Brief Description of the Drawings and the Best Mode for Carrying Out the Invention.

BRIEF DESCRIPTION OF THE DRAWINGS

FIGS. 4-39 are successive flow charts describing a program for operating the apparatus illustrated in FIGS. 1 through 3 by which medical test data may be generated, stored and retrieved in accordance with the subject invention.

BEST MODE FOR CARRYING OUT THE INVENTION

Figure 1:
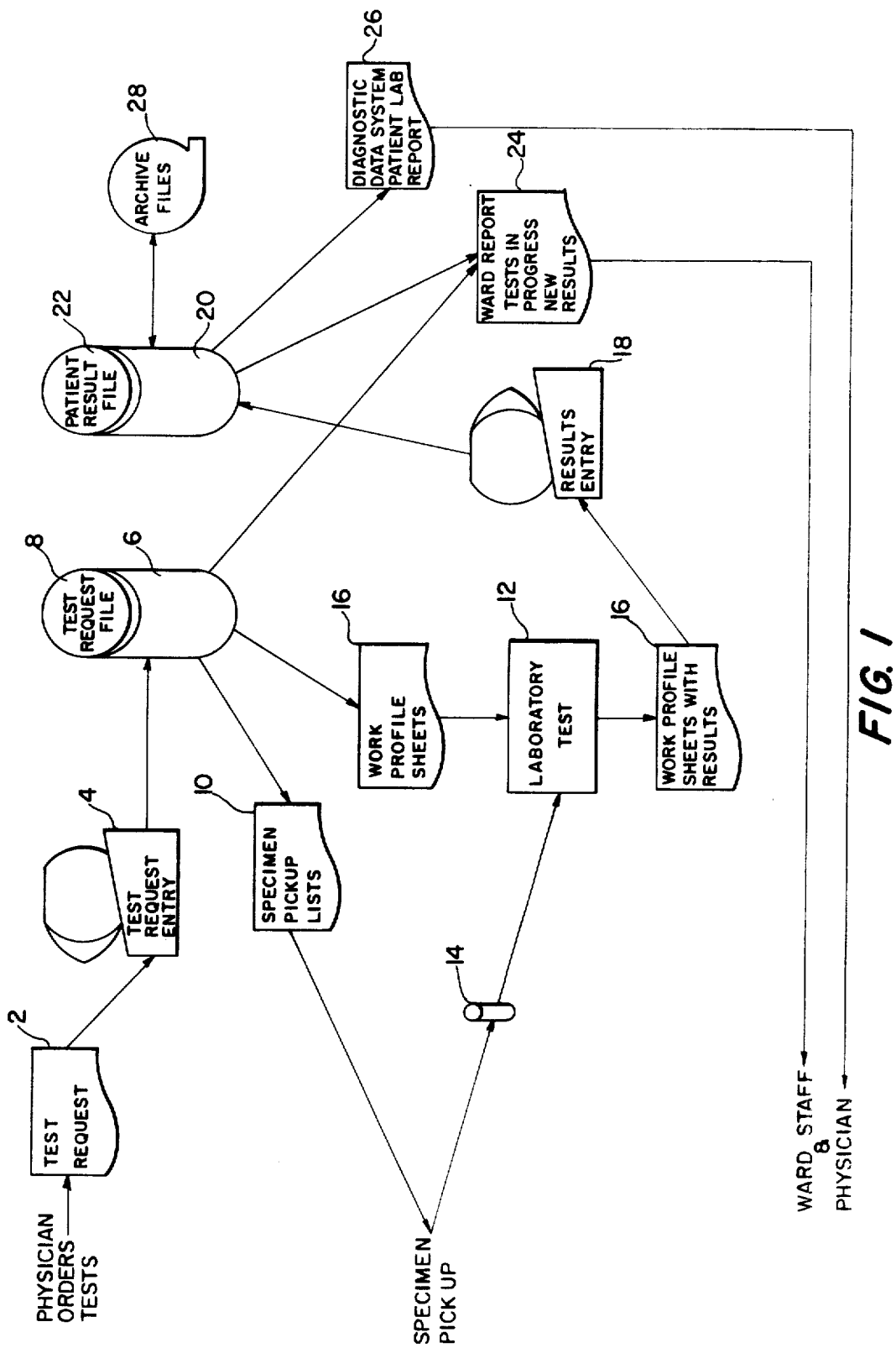
FIG. 1 is a schematic diagram of a system for generating, storing and retrieving medical test data for a predetermined patient population in accordance with the subject invention.

To provide a clear understanding of the subject invention, reference is initially made to FIG. 1 which discloses a schematic illustration of the overall flow of test data information within a hospital utilizing the subject invention. As in any hospital, medical services are dispensed to a changing patient population by a staff of professional patient treatment personnel including doctors, nurses, clinical technologists, and others whose responsibilities include generating test requests, conducting tests, storing the results, and interpreting the results upon retrieval. More particularly, FIG. 1 indicates that medical test requests 2 are normally generated by physicians but other personnel within the hospital may have limited authority to order patient tests such as nurses or other trained medical personnel. Prior to the use of computerized medical data handling systems, the test request 2 was given directly to those personnel charged with the responsibility of obtaining patient specimens after which the test request and specimen would be forwarded to the laboratory for performance of the test and recording of the results on the test request form for return to the physician.

In the system illustrated in FIG. 1, the test request 2 is no longer used in this way. Rather, the information contained on request 2 is entered into the system by test request entry apparatus 4 such as a keyboard input. Entry apparatus 4 may be equipped with a CRT display to allow vertification of the fact that the appropriate test request has been entered into the system. From the test request entry terminal 4, or other terminals which may be placed throughout the hospital, all requests are electronically forwarded to a test request compiler 6 for storage in a test request file 8. The function of compiler 6 and file 8 may be performed by a specially programmed general purpose digital computer having a capacity commensurate with the total volume of test requests which can be expected given the size of the patient population. Naturally, it is not necessary that the compiler and storage file be located within the hospitabl since the function of these two units could be performed by equipment located at a distance and used by the hospital on a time sharing basis with other data processing service users. The test request compiler 6 is organized to periodically generate specimen pick-up lists 10 which are then distributed to the various wards in the hopsital to assist nursing personnel or others in collecting the various patient specimens necessary for cnducting the specific test requests generated by the patient treatment personnel who prepared the original test request 2. Obviously, this sytem of organizing the requests can result in very considerable savings of time in paperwork. The system also promotes efficient execution of the specimen pick-up regimen which occurs within each ward since the pick-up can be organized in accordance with the classes of tests requested and the physical location of the patients from which the specimens must be derived.

Normally the patient specimens constituting body fluids, or tissue samples, which are forwarded to a laboratory 12 in individual specimen containers 14 marked to identify the patient and type of sample or specimen contained therein. Once received in the laboratory 12, the various requested tests may be performed on the specimen samples in accordance with a work profile generated by the compiler 6 on profile sheets 16 describing the specific type of test to be performed on the respective patient specimens. Again improved efficiency is achieved by this process since the various tests required to be performed may be organized in a logical fashion to assist the laboratory personnel to organize their equipment and their activities in accordance with a logical regimen or daily protocol to thereby assure greater accuracy and efficiency in their activities.

Once the tests are performed the results may be recorded on the work profile sheets 16 for subsequent manual and/or machine entry at an entry terminal 18. A keyboard input, card reader or other type of peripheral input device may be employed as the entry terminal 18 as long as it is capable of generating electrical signals representative of the patient, the type of test, the date and/or time of the test and the test results. Such signals may in some instances be generated automatically by on-line laboratory test equipment such as a COULTER COUNTER designed to generate electrical signals which may be directly received by a data processing system. The results received by terminal 18 are forwarded to a patient result compiler 20 for storage in a patient result file 22. Compiler system 20 and 22 may be the same equipment as compiler and request file 6 and 8 or may be a separate stand alone specially programmed digital computer which is capable of receiving, storing and formatting the test data received from the laboratory through terminal 18.

On a daily basis or at various times during the day, compiler 20 is designed to generate a ward report 24 consisting of all tests then in progress which were requested on patients located on a particular patient ward as well as all new test results for tests completed but not previously reported to the same ward. The ward report 24 may take the form of a hard copy generated by the compiler 20 and distributed to the wards or may take the form of an electrical signal designed to generate an image on a CRT tube located in the ward. Compiler 20 is also designed to generate a diagnostic data system patient lab report 26. As will be explained in much greater detail below it is a primary object of this invention to generate electrical signals through terminal 18 or otherwise for storage in the compiler 20 for subsequent presentaion in a patient report 26. The data appearing or report 26 is formatted to assist patient treatment personnel to assimilate the test results and related supplementary information and to arrive at a diagnosis and mode of treatment which represents the best possible medical service not only to the individual patient but to the overall patient population in light of the total amount of resources avaiable for health delivery services. When a patient leaves the predetermined patient population, his accumulated tests records are transferred to an archives file 28 for permanent storage and subsequent recall should the need arise.

Figure 2:
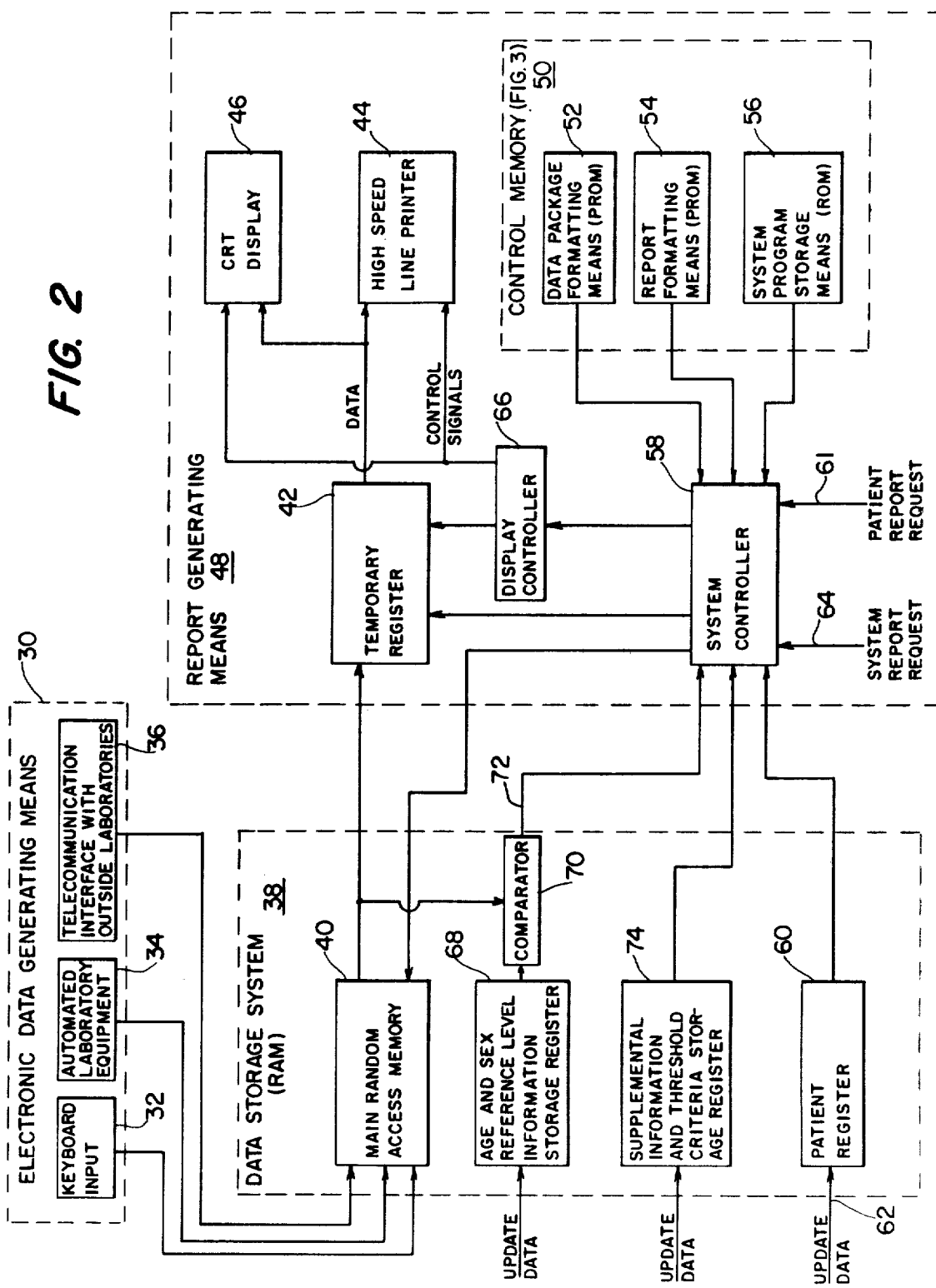
FIG. 2 is a more detailed schematic illustration of the electrical apparatus for generating patient data reports in accordance with the subject invention.

Attention is now directed to FIG. 2 in which a detailed schematic diagram appears of the hardware which may be employed to implement the subject invention. Data representing the results of particular tests conducted on specimens of patients making up a given patient population, such as all of the patients in a particular hospital, is entered into the system by means of an electronic data generating means 30. This portion of the system may take the form of a keyboard input 32, located in the hospital clinical laboratory, with which laboratory technicians may enter individual test results. Input 32 may also be used to add addiational data to machine generated information for entry into the system storage as discussed hereinbelow. Test data may also be entered into the system by means of on-line laboratory equipment 34 of the type wherein one or more patient specimens are fed into the machine for serial or parallel tests, the results of which are converted to electrical signals compatible with the remainder of the data system illustrated in FIG. 2. The electronic data generating means 30 may further include a telecommunication interface 36 for connection with laboratory remotely located from the hospital such that data generated in the remote laboratory can be directly communicated to the system of FIG. 2 over communication lines such as commercial telephone lines.

The electrical signals generated by the electronic data generating means 30 may take the form of a separate digital electrical signal field for each test result stored in the system wherein each digital electric signal field includes (1) a first set of electrical digital signals identifying a particular medical test from a predetermined set of known medical tests, (2) a second set of electrical digital signals identifying the results of the tests identified by the first set, (3) a third set of electrical signals indentifying the date on which the test identified by the first set was conducted and (4) a fourth set of electrical digital signals identifying the patient for whom the test identified by the first set was conducted. Each of the digital electrical signal fields produced by means 30 is forwarded to a data storage system 38 which is designed to receive and store all of the electrical digital signal fields on the entire patient population serviced by the overall system.

Data storage system 38 includes a main random access memory 40 having the capabiity and capacity to store all of the test results produced for each of the patients making up the entire patient population serviced by the system for the entire period that each patient remains a member of the patient population. Thus, the capacity and form of the random access memory 40 will be dictated by the capacity required to store all of the data for the then existing total patient population. Obviously as patients are discharged from the hopsital, the stored test data relating to that patient may be removed from the main random access member 40 and placed in the archive 28 (FIG. 1). Even for a medium size hospital the amount of test data involved can become extremely voluminous necessitating the use of very high capacity storage memory such as magnetic tape and/or large scale magnetic discs. A critical characteristic of this memory, however, is that the data stored therein must be retrievable randomly in accordance with the informaion identified in each of the sets making up each digital electrical signal field. As will be described further hereinbelow, the data storage system 38 includes additional programmable storage registers which expand the capabilities of the disclosed system.

At predetermined times, such as once a day or more often if required, the system illustrated in FIG. 2 is operated to generate individual patient reports by withdrawing the test data for a particular patient, storing this test data in a temporary register 42, formatting the data, and generating an output image such as by means of a high speed line printer 44 designed to produce a hard copy bearing the medical test data in a desired format. In addition or alternatively, the patient report image may be formed on the screen of a CRT display 46. Both the printer 44 and display 46 may be located centrally in the hospital, or, alternatively, separate printers 44 and/or displays 46 may be located through the hospital to produce patient reports at desired locations adjacent the patient and/or the patient treatment personnel.

Register 42, printer 44 and display 46 form a portion of report generating means 48 which is designed to generate periodically the individual patient test data reports for each patient within the patient population. Each of these reports includes all stored test data for the particular patient for the total time period during which the patient has been a member of the patient population and is organized to present the cumulative test data in a highly compact pattern of data packages. A particularly critical characteristic of this invention is that each data package includes only results of tests making up a particular organ system disease related subset of tests out of the total set of tests which are available to the patient treatment personnel. The exact format of each data package will be discussed in greater detail hereinbelow.

In order to achieve a consistently repeated pattern of test results in each patient report, the report generating means 48 includes a control memory 50 containing a data package formatting means 52 for generating successive data package formatting signals to cause results of repeated performance of the same test on the same patient to appear in a single column of a single data package and to cause the results from all tests within the corresponding subset of tests making up the data package, which test were conducted on the same patient on the same day, to appear in a single row of the same data package. Thus, data package formatting means 52 has the function of insuring that each data package is formatted exactly in the same manner as all other data packages within each and every patient report generated by the system illustrated in FIG. 2. Control memory 50 also includes a report formatting means 54 for generating an identical succession of report formatting electrical signals each time a patient report is produced by the printer 44 or CRT display 46. The identical report formatting electrical signals are designed to identify the test and sequence of tests included in each successively formed data package and for identifying the sequence in which the data packages are to appear in each patient report.

Control memory 50 further includes a system program storage means 56 within which is sorted the iterative program commands necessary for operation of the overall system. Formatting means 52 and 54, in combination with storage means 56, may form portions of a single control memory 50 such as the control memory of a general purpose digital computer. Alternatively, means 52, 54 and 56 may be individual programmable read only memories. Ideally, each of these elements should be reprogrammable to accommodate changes in the data package formatting or the report formatting and to accommodate modification in the options of the overall system operation.

Connected with each portion of the control memory 50 is a system controller 58 adapted to generate image control signals which cause the printer 44 or CRT 46 to form a patient report for each patient within the patient population by retrieving all test data accumulated on each patient during the entire period that the patient has remained a member of the patient population. The system controller 58 is designed to cause the CRT or printer to form a predetermined succession of comprehensive data packages in accordance with the report and data package formatting signals generated by means 52 and 54, respectively. Each data package is caused to contain a consistent pattern of visible indicia including the results of all tests defined by the data package which were conducted on the patient during the entire period in which the patient has remained a member of the patient population. The visible indicia in each column represents the second sets of those signal fields having identical first sets of signals stored in memory 40 for each patient. System controller 58 is designed to generate printer control signals which cause the printer to print the visible indicia in each column of each data package in chronological order as determined by the fourth set of each corresponding signal field stored in memory 40.

By organizing the system as described above, each successively formed patient report will supersede all prior reports and will include all stored medical test results organized in a compact comprehensive organ system disease related pattern in which the order of the data packages and the order of tests appearing in each package is identical in all reports. This identity of pattern from one report to the next will assist the patient treatment personnel to assimilate and understand organ system disease related test information in the least possible amount of time. The system controller 58 is designed to respond to requests supplied on input line 61 for successive generation of patient reports for each of the patients contained in a patient register 60 which forms a part of the data storage system 38. Patient register 60 is designed to receive update data on line 62 consisting of signals representing the addition of patients to the total patient population upon admission of patients and conversely signals representative of the discharge of patients. The content of the admission signals will include the patient's age, sex, and other vital statistics useful to the hospital in maintaining adequate records relating to each individual patient.

System controller 58 is also designed to receive special system report requests on line 64 which can assist the hospital administration to manage and analyze the hospital operation particularly as regards to the medical test laboratory functions.

The printer 44 and display 46 may be controlled directly by the system controller 58 or may include a separate display controller 66 which is designed to operate semi-independently of the system controller 58 thereby freeing the system controller to operate more quickly and efficiently.

As further illustrated in FIG. 2, the data storage means 38 may include a reference level information storage register 68 for storing reference level information signals indicating the normal range for a patient of a given sex and age for each of the possible tests for ultimate display in the inidivudal patient reports. As will be described hereinbelow, the reference level information recorded in register 68 is caused to be printed on each inidivudal patient report at a position which allows the clinician to use the reference level information as an aid to interpretation of the displayed test results. Further assistance is given to the clinician by means of a comparator circuit 70 connected with both the main random access memory 40 and the reference level information storage register 68 to permit a comparison between the tests results stored in the main random access memory 40 and the normal range for each test adjusted in accordance with the age and sex of the patient whose report is being generated. Comparator circuit 70 is thus designed to compare the test results as represented by the second set of each signal field stored in the main random access memory 40 with the age and sex adjusted normal reference range defined by register 68. If an out-of-range test result is discovered, comparator 70 produces a signal over line 72 connected with the system controller 58 which signal is designed to cause the controller to generate a signal causing a visible out-of-range indicator to appear in the image formed by the CRT display 46 or the high speed line printer 44 adjacent the visible indicia appearing in the patient report which represents the out-of-range test results.

Data storage means 38 is designed to include an additional register 74 for storing information useful to a clinician in interpreting specific test results which are out of the normal range for such tests. This register may be deemed a supplemental information and threshold criteria storage means. The type of information stored in register 74 could include inidications of possible diagnosis normally indicated by a particular out-of-range test result or alternative types of treatment and the current cost for such type to aid thereby the clincain in selecting an appropriate treatment which is both suitable for the patient and the most cost effective under the circumstances. For example, certain types of antibotics may be prescribed despite their high daily cost when other types of antibotics having the same efficacy in a given circumstance, and costing significantly less could be prescribed without compromised quality patient care.

Figure 3:
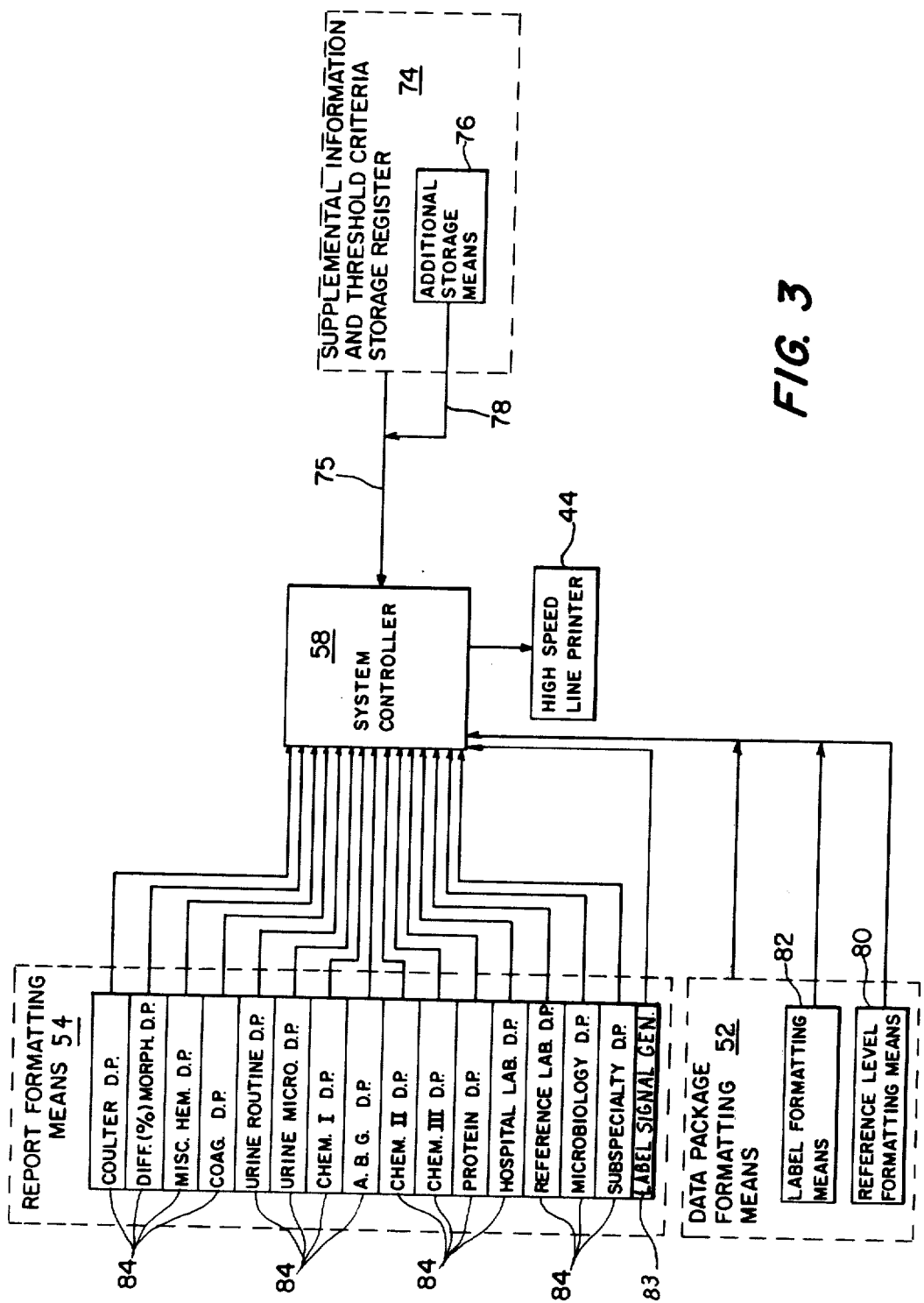
FIG. 3 is still more detailed schematic illustration of a data storage, control memory and system controller of the subject invention.
Figure 8:
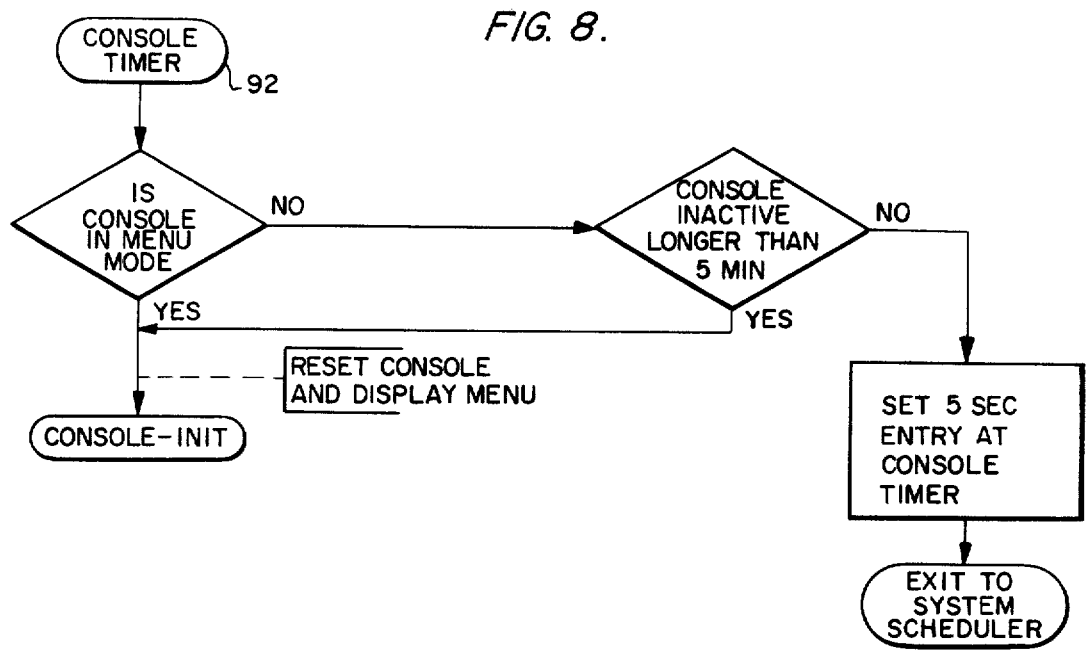
Figure 37:
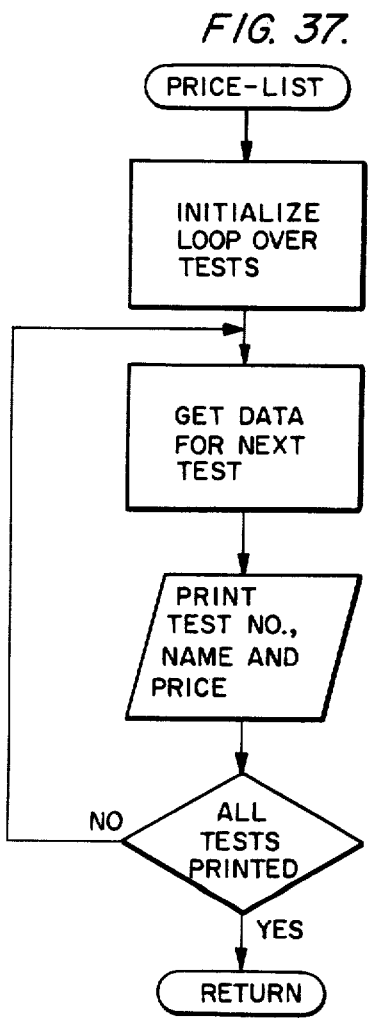
Figure 9:
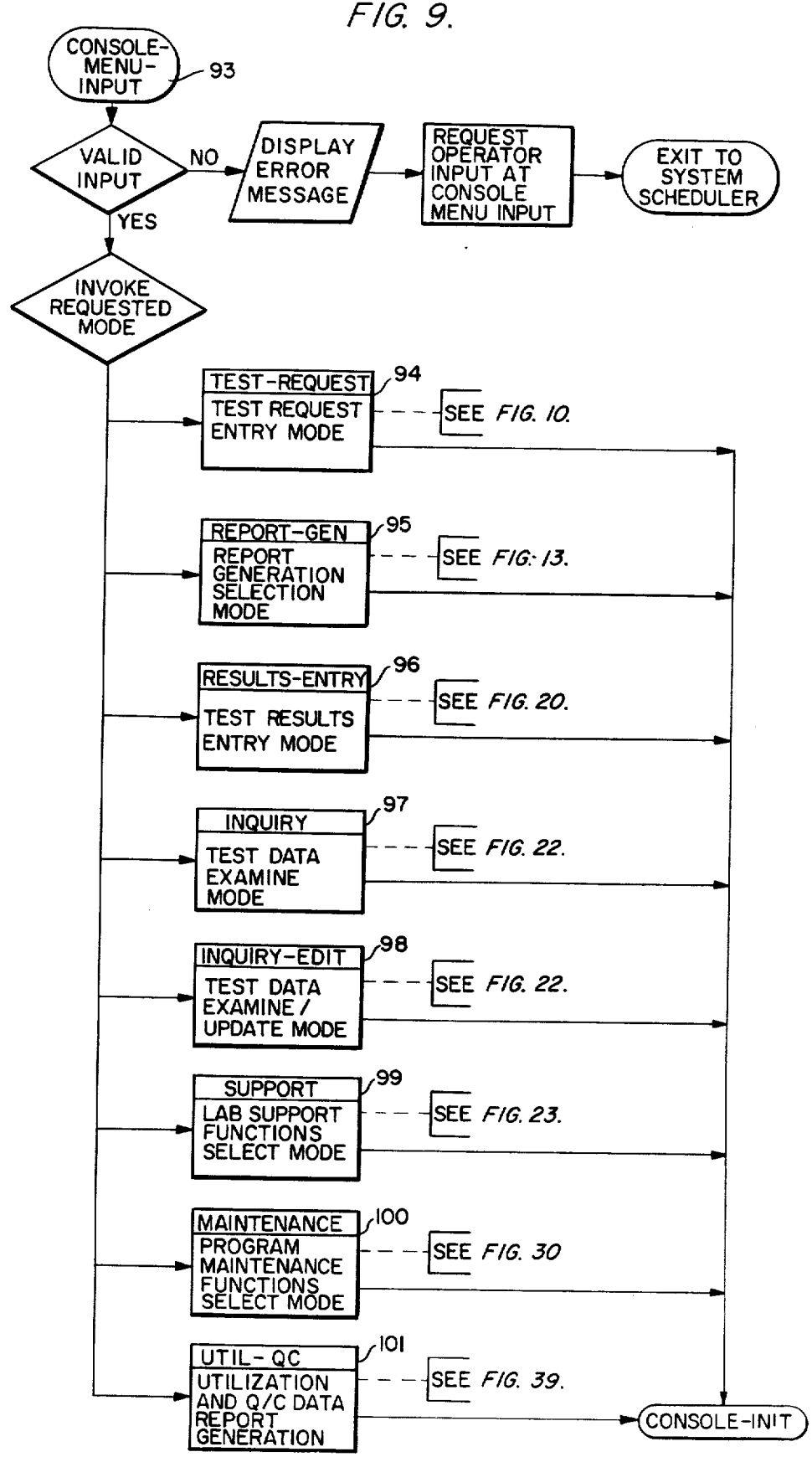

Turning now to FIG. 3, the supplemental information and threshold criteria storage register 74 is illustrated as including an additional storage means 76 which is designed to store signals representative of the information regarding alternative treatment and current costs for each type of treatment. Note that additional storage means 76 is connected to system controller 58 through line 78 and line 75 to cause the controller to generate signals operating the printer 44 to print the alternative treatment and current cost information on the patient report in association with the particular printed test results whenever the stored signals indicate an out-of-range result given the age and sex of the patient.

The data package formatting means 52 is shown in FIG. 3 as including a reference level formatting means 80 for generating reference level formatting signals to cause reference levels for a patient to be displayed above each column of test results appearing in each data package formed by printer 44. Similarly, the data package formatting means 52 may also include a label formatting means 82 for generating label formatting signals to cause visible indicia identifying the type of tests to appear above each column of test results in each data package corresponding to the first set of each signal field associated with the column. FIG. 3 further discloses that the report formatting means 54 includes a signal generator 83 for generating label signals representative of each type of test within each data package. Means 54 also includes separate data package generators 84 for generating the test identifying signals necessary to allow system controller 58 to retrieve, organize and format the test data for each patient report generated by the system in order to insure that test data corresponding to a particular test will always appear at the same location and within the same data package appearing within each patient report.

The hard copy produced by printer 44 on the image produced by CRT 46 will generally include, in its complete form, two parts: the Microchem Section, including all known microbiological and biochemical diagnostic tests, and the Subspeciality Section, including all known diagnostic procedures utilized by the various medical subspecialties such as Radiology and Cardiology. The Microchem Section includes most of the diagnostic tests known and used by the medical profession and is therefore subdivided into five categories to present all of this information in a logical, clincially oriented format. Category I includes the basic hematology tests, Category II includes routine urinalysis, Category III includes basic chemistry tests, Category IV includes special chemistry tests and Category V includes microbiological tests. Each category is subdivided into data packages to organize the information further so that all of the information is presented to the clinical physician so that it will provide the maximum assistance in diagnosing, treating and monitoring organ system related clinical conditions. The arrangement of the data packages has been determined to be one which will enable the physician to absorb critical information quickly and follow clinical trends at a glance. As discussed above with regard to FIGS. 2 and 3, the tests and sequence of tests appearing in each data package is determined by the electrical signals generated by the report formatting means 52. In response to the signals the system controller causes the line printer 44 or CRT 46 to produce the desired data package. In each of the data packages discussed hereinbelow the individual tests are identified by an abbreviation the meaning of which appears in the following Chart I along with an indication of the units in which the results are reported:

CHART I

| ABG | Arterial Blood Gases |
|---|---|
| ACET | Acetone |
| ALB | Albumin |
| ALPHA1 | Globulin |
| ALPHA2 | Globulin |

CHART I-continued

| AMY | Amylase |
|---|---|
| APP | Appearance |
| APTT | Activated Partial Thromboplastin Time |
| BACT | Bacteria |
| BASO | Basophil |
| BETA | Globulin |
| BILD | Bilirubin Direct |
| BILT | Bilirubin Total |
| BLD | Blood |
| BND | Bands |
| BT | Bleeding Time |
| BUN | Blood Urea Nitrogen |
| CA | Calcium |
| CAP | College of American Pathologists |
| CHOL | Cholesterol |
| CL | Chloride |
| COAG | Coagulation |
| $CO_2$ | Carbon Dioxide, Total Carbon Dioxide |
| CPK | Creatine Phosphokinase |
| CREA | Creatinine |
| CT | Count |
| DIFF/MORPH | Differential/Morphology |
| EOS | Eosinophil |
| EPC | Epithelial Cells |
| ESR | Erythrocyte Sedimentation Rate |
| FDP | Fibrin Degradation Products |
| FE | Iron |
| FIBRINO | Fibrinogen |
| GAMMA | Globulin |
| GGTP | Gamma Glutamyl Transpeptidase |
| GLOB | Globulin |
| GLU | Glucose |
| GM/DL | Gram/Deciliter |
| HCT | Hematocrit |
| HDL | High Density Lipoprotein |
| HGB | Hemoglobin |
| HT | Height |
| IBC | Iron Binding Capacity |
| IU/L | International Units/Liter |
| K | Potassium |
| K/MM3 | Thousand/Cubic Millimeter |
| LDL | Low Density Lipoprotein |
| LDH | Lactate Dehydrogenase |
| LIP | Lipase |
| LYM | Lymphocytes |
| L/MIN | Liter/min |
| MCG/ML | Microgram/Milliliter |
| MCH | Mean Corpuscular Hemoglobin |
| MCHC | Mean Corpuscular Hemoglobin Concentration |
| MCV | Mean Corpuscular Volume |
| MEQ/L | Milliequivalents/liter |
| MG | Magnesium |
| MG/DL | Milligram/Deciliter |
| MIN | Minute |
| MMHG | Millimeters of Mercury |
| MMOL/L | Millimoles/liter |
| MM/HR | Millimeters/hour |
| MONO | Monocytes |
| MOSM/KG | Milli Osmoles/KG |
| M/MM3 | Million/cubic millimeter |
| NA | Sodium |
| NG/ML | Nanograms/Milliliter |
| OSM(U) | Osmolarity-Urine |
| OSM(S) | Osmolarity-Serum |
| OTHR | Other |
| $O_2RX$ | Oxygen Therapy |
| $O_2$ SAT | Oxygen Saturation |
| $PCO_2$ | Partial Pressure of $CO_2$ |
| % | Percent |
| % $O_2$ | Oxygen Therapy % $O_2$ |
| PG/ML | Picogram/ML |
| PLAT | Platelets |
| POLYS | Polymorphonuclear Leukocytes |
| $PO_2$ | Partial Pressure of $O_2$ |
| $PO_4$ | Phosphate |

CHART I-continued

| | |
|---|---|
| PROT | Protein |
| PTA | Prothrombin Activity |
| RBC | Red Blood Count, Cells |
| RETIC CT | Reticulocyte Count |
| SAP | Serum Alkaline Phosphatase |
| SEC | Second |
| SGPT | Serum Glutamic Pyruvic Transaminase |
| SGOT | Serum Glutamic Oxalacetic Transaminase |
| SGR | Specific Gravity |
| SHUR | Standard Hospital Utilization Reporting |
| STOOL OB | Occult Blood |
| SUG | Sugar |
| SUM | Standard Unit of Measure (SHUR) |
| TG | Triglycerides |
| TP | Total Protein |
| U | Units |
| UG/DL | Micrograms/Deciliter |
| URIC | Uric Acid |
| UUG | Micro Microgram |
| U3 | Cubic Micron |
| U/DL | Units/Deciliter |
| WBC | White Blood Count, Cells |
| WT | Weight |

Category I includes four data packages which contain all routinely performed hematology tests. As with all of the data packages in this category, the names of the tests and the units in which results are reported are set forth across the page, allowing a vertical chronological listing of a large number of test results underneath. Where the units in which adjacent tests are identical a single line is drawn beneath the abreviations for all such tests with only a single indication of the units appearing below the line. The first data package in the Hematology category appears in Chart II below.

CHART II

| COULTER: | HGB | HCT | WBC | PLAT | RBC | MCV | MCH | MCHC |
|---|---|---|---|---|---|---|---|---|
| | GM/DL | % | K/MM3 | | M/MM3 | U3 | UUG | % |

The first data package Chart II presents the tests performed by the automated Coulter blood counting equipment. To present a complete overall picture of all of the important components of the blood, this data package has included the Platelet Count (represented by PLAT), information not heretofore included with the data generated by the Coulter machine as it has been presented by other computerized systems.

The second data package in the hematology section appears in Chart III below:

CHART III

| DIFF (%)/MORPH: | POLYS | BND | LYM | MONO | EOS | BASO | OTHR | RBC | PLAT |
|---|---|---|---|---|---|---|---|---|---|

This data package condenses all essential morphological information for both white and red blood cells and platelets so that it is presented in one place. The extensive list of abnormalities which are occasionally encountered in red blood cells has been eliminated to reduce the amount of space occupied by the remaining tests. In the rare instances where additional information is required, such information can be supplied by footnotes. For example, if an abnormal red cell form is found, the system of the present invention will note the existence of the abnormality under the column headed RBC and a footnote will be generated at the bottom of the report to explain specifically what has been found. Any similarly encountered abnormality of the platelets will be treated in a like manner under the column headed PLAT. (See Chart II). Such a condensed presentation is much more convenient to use than prior data displays and eliminates what is usually a substantial amount of wasted space and paper.

Chart IV below presents the third data package in the hematology section:

CHART IV

| MISC: | | | | | | | | |
|---|---|---|---|---|---|---|---|---|
| STOOL OB | RETIC CT | EOS CT | ESR | FE | IBC | FERRITIN | B12 | FOLATE |
| | % | CELLS/MM3 | MM/HR | UG/DL | | NG/ML | PG/ML | NG/ML |

This data package compiles in one place miscellaneous hematology tests that have not been grouped together in previous patient test data reports. Most of the data presented here, specifically the tests entitled STOOL OB, FE, IBC, FERRITIN, B12 and FOLATE, relate to the major causes of anemia, a commonly encountered clinical condition. This data package enables the physician to review at a glance the information most helpful in diagnosing the kind of anemia a patient has and following the effects of treatment. The remaining tests are commonly used hematology tests which are not necessarily specific for any particular clinical condition.

The final hematology data package is presented in Chart V below:

CHART V

| COAG: | | | | |
|---|---|---|---|---|
| PTA | APTT | BT | FIBRINO | FDP |
| SEC | SEC | MIN | MG/DL | UG/ML |

This data package sets forth in one place information essential to the physician's knowledge of the patient's blood coagulation characteristics. These tests have not appeared together in the same place in any other computerized patient test data report. Consequently, in the past a physician desiring to obtain a complete picture of a patient's blood coagulation characteristics was forced to flip through several pages of information. By having all of this information together, the physician can now easily monitor the effects of anticoagulation therapy with the tests entitled PTA and APTT and the indicia of such disorders as diffuse intravascular coagulopathy at the same time.

Chart VI below sets forth the data packages which make up Category II:

CHART VI

| ROUTINE: | APP | PH | II. URINALYSIS SGR | SUG | ACET | PROT | BLD | BILE |
|---|---|---|---|---|---|---|---|---|
| MICRO: | WBC | RBC | BACT | CASTS | EPC | OTHR | | |

The second major category of information presented in the system of the present invention pertains to that which a physician expects to receive when a routine urinalysis is ordered on a patient. The information presented in these two data packages is displayed above in Chart VI and includes that generated by routine chemical, macroscopic and microscopic analysis. Any specific quantitative chemical analyses ordered on the urine would be reported in the Special Chemistry section described below.

Category III, which includes all the basic and special chemical analyses done on blood, contains those tests which, in prior systems, are particularly the ones which have not been organized into a format which is logical from the perspective of the end user of the data, the clinical physician. Heretofore, the organ system relationship between the diagnostic tests and the conditions of which they are diagnostic has not been utilized to present test data in a format designed to facilitate its assimilation, interpretation and application by the clinical physician. The data packages in this section have been organized and arranged to present the clinical physician with all of the essential information needed to ascertain the existence or nonexistence of disease conditions involving the major organ systems. The first of these data packages, entitled Chem I, is displayed in Chart VII below:

CHART VII

| CHEM I: | | | |
|---|---|---|---|
| GLU BUN CREA | Na K CL CO2 | OSM(S) OSM(U) |
| MG/DL | MMOL/L | MOSM/KG |

The Chem I data package displayed above includes tests which tend to be ordered frequently and are usually repeated together. These tests have traditionally been grouped together, primarily for the convenience of the ordering physician. However, because the goal of the format of this data package is to enable the physician to obtain a complete picture of renal function as it coordinates with acid-base balance, this data package is more complete than previously available groupings of these test results.

Not only is the arrangement of the tests in the data packages clinically oriented in the system of the present invention, the sequence in which the data packages appear has also been selected with regard to clinical considerations. Therefore, the next data package, displayed in Chart VIII below, contains information from tests on arterial blood gases. There are clinical conditions in which it is extremely helpful to the physician to be able to evaluate this information in conjunction with test data on acid-base balance, which appears in the preceeding data package. While some of this information has been set forth together in one existing system, no attempt was made before now to do so in a format which considered its relationship to another interrelated set of test results.

CHART VIII

| A.B.G.: | | | | | |
|---|---|---|---|---|---|
| PH | PCO2 PO2 | O2 SAT | CO2 | L/MIN % O2 |
| | MMHG | % | MMOL/L | O2 RX |

The third chemistry data package, entitled Chem II, is set forth in Chart IX below:

CHART IX

| CHEM II: | CA PO4 URIC | MG | AMY | LIP | CHOL TG HDL LDL |
|---|---|---|---|---|---|
| | MG/DL | MEQ/L | U/DL | U | MG/DL |

The Chem II data package displayed above groups together for the first time a series of tests which are indicated in many clinical conditions. The levels of many of these chemical substances, such as calcium (represented by CA) and phosphate (represented by PO4), are deranged at the same time and may be diagnostic of more than one clinical condition. This data package is ideal from the clinical physician's standpoint, for example, for diagnosing, prescribing treatment and monitoring the effects of that treatment in an alcoholic patient. It is also a valuable aid in the differential diagnosis of certain clinical conditions affecting the pancreas, gall bladder and parathyroid which produce some of the same initial test results as those encountered in an alcoholic patient. The physician has in one place the most relevant data relating to these conditions which will reflect the effects of what therapy or surgery has been ordered. This enables him to rule out the presence of one of these conditions and confirm the existence of another much more efficiently and effectively than has been possible up to now. This data package provides a far more complete clinical picture than that provided by previous systems, which have grouped some, but not all, of these tests together.

Two related chemistry data packages are displayed in Chart X below:

CHART X

| PROTEINS: | TP ALB GLOB ALPHA 1 ALPHA 2 BETA GAMMA |
|---|---|
| | GM/DL |
| CHEM III: | BILT BILD SAP GGTP SGPT SGOT LDH CPK |
| | MG/DL         ID/L |

The Chem III and Proteins data package displayed above are presented in that sequence in the hard copy report of patient test data in the present invention. Together they provide the clinical physician with all of the most important data relating to liver function. The Chem III data package includes tests which are performed by automated laboratory equipment and by itself, presents an essentially complete clinical picture of this important organ system. However, the inclusion of the Proteins data package adjacent to the Chem III test results is a more complete presentation from the clinical physician's perspective.

The final data packages in the chemistry section are displayed in Chart XI below:

CHART XI

| HOSPITAL LAB: | TEST | RESULT | REFERENCE RANGE | UNITS |
|---|---|---|---|---|
| REFERENCE LAB: | | | | |

Category IV, which includes all of the rest of the known blood chemistry tests, presents its data packages in a slightly different format than those discussed above. Since this group of tests is so numerous and since most of these tests are ordered infrequently, a vertical listing of these tests is adequate for assimilation and interpretation from the clinician's perspective. Once the physician is familiar with the format of the basic chemistry data packages and knows which tests will always appear in that section, he knows to consult the special chemistry section for all other test results. Category IV is subdivided to reflect those tests which were performed in the hospital laboratory and those which were sent to a commercial or reference laboratory. This information will enable hospitals to compare turn around times and, desirably, costs of performing these tests in the hospital laboratory as compared to the reference laboratory. This section will also include information, in the form of footnotes (using the additional storage means 76 of FIG. 3), generated when a test result is outside the reference range. These footnotes will provide a concise statement of the significance of an abnormal test result and, will, when appropriate, direct the physician to other interrelated test results. An example of the use of such a footnote is included in Chart XIV below. The ready availability of such important information assures that results of rarely used tests will be interpreted accurately, saves valuable physician time and adds to the medical knowledge of the physicians and other health care personnel who use the test data.

The microbiology data package is set forth in Chart XII below:

CHART XII

| ORIGIN | MICRO EXAM | CULTURE | SENSITIVITIES |
|---|---|---|---|

Category V provides all information concerning microbiological tests routinely performed in hospitals. The format of this data package is designed to include all essential information in a space-saving condensed form. This data package will provide not only routine microbiological data but also includes information concerning antibiotic therapy. Space is provided to present information regarding the sensitivities of the infective organism to a group of antibiotics. A number next to the same of the drug will indicate the order of desirability of treating the infective organism with that particular drug. A footnote will, in addition, be generated to give information concerning the cost per day to the patient of prescribing each drug of choice. This is more clearly illustrated with reference to the following example set forth in Chart XIII below:

CHART XIII

| | ORIGIN | MICRO EXAM | CULTURE | SENSITIVITIES |
|---|---|---|---|---|
| 20 APR 1600 | URINE | GRAM POS. COCCI | STAPH. EPIDER- MIDIS G.T. 100 K/ML | CHLORO(1); KANA(2); FURA(3) CEPH: VANCO: METH; CLINDA; TRIM; ERYTHRO |
| (1) $10.00; (2) $2.50; (3) $6.00 | | | | |

Chart XIII illustrates the Category V data package containing actual test results. The urine culture done on April 20 demonstrates the use of the treatment information referred to above. The infective organism, *Staphylococcus epidermidis*, was found to be sensitive to the drugs listed under the column headed "Sensitivities." The first three drugs are followed by numbers indicating that all three are drugs of choice for use against this particular organism and should be considered for therapy according to the order designated. At the bottom of the page is listed for each drug the cost to the patient per day of drug therapy. The physician may then chose the antibiotic therapy with up to date cost information provided with the test results. In the case illustrated, assuming the absence of problems interfering with the efficacy of the drug, drug number 2 should be prescribed since it costs substantially less. In the past, doctors have had to consult additional reference materials for information regarding the drugs of choice once a microbiology test result was available. Moreover, the only way to ascertain the cost information as presented in the chart above would be to contact the hospital pharmacy, which is likely to be a time consuming procedure. It is highly unlikely that many doctors in the past took the time to determine the cost of the treatment they prescribed.

The last section of the patient test data report of the present invention includes all the known diagnostic procedures used by the different medical subspecialities. Data provided in this section encompasses such areas as pathology, radiology, cardiology, neurology and gastroenterology. Information generated by such procedures as electrocardiograms, endoscopic examinations, x-rays and the like is presented in this section in a concise narrative form.

Chart XIV presents an example of the hard copy report of patient test data.

CHART XIV

LAB REPORT -- Acute Care Hospital, Busytown, U.S.A.
SMITH, JOHN J.   ADM: 30 DEC 77
DOB: 4/30/35   AGE: 42   SEX: M   WT: 175   HT: 72
29 88 04   LOC: 4S RM 470
DR: COLI

CHART XIV-continued

CUMULATIVE AT 04 FEB 1300

I. HEMATOLOGY

| COULTAR | HGB GM/DL | HCT % | WBC K/MM3 | PLAT | RBC M/MM3 | MCV U3 | MCH UUG | MCHC % |
|---|---|---|---|---|---|---|---|---|
| REFERENCE | 14.0 | 42.0 | 4.0 | 140 | 4.6 | 80 | 26 | 31 |
| RANGE | 18.0 | 54.0 | 11.6 | 440 | 6.2 | 110 | 33 | 36 |
| 30 DEC 0800 | 15.4 | 47.5 | 9.6 | 300 | 4.48 | 105 | 24.1 | 30.4 |
| 31 DEC 0700 | 15.3 | 47.3 | 12.5+ | | 4.66 | 108 | 25.0 | 33.0 |
| 01 JAN 0700 | 15.5 | 48.0 | 18.6+ | | 4.78 | 106 | 24.0 | 34.0 |
| 08 JAN 0400 | 10.8− | 33.1− | | | | | | |
| 10 JAN 1400 | 10.2− | 31.4− | 11.0 | 240 | 4.75 | 102 | 28.0 | 33.0 |
| 10 JAN 1700 | 10.9− | 33.1− | | | | | | |
| 11 JAN 0200 | 8.6− | 27.0− | | | | | | |
| 11 JAN 0700 | 10.1− | 30.8− | | | | | | |
| 12 JAN 1400 | 10.1− | 31.4− | | | | | | |
| 13 JAN 1700 | 7.7− | 23.9− | | | | | | |
| 13 JAN 2100 | 8.9− | 27.5− | | | | | | |
| 14 JAN 0700 | 7.1− | 22.1− | | | | | | |
| 14 JAN 1600 | 10.0− | 30.2− | | | | | | |
| 15 JAN 0700 | 8.8− | 28.2− | | | | | | |
| 16 JAN 0700 | 9.8− | 29.6− | | | | | | |
| 17 JAN 0700 | 10.8− | 33.4− | | | | | | |
| 18 JAN 0700 | 11.8− | 34.4− | | | | | | |
| 24 JAN 0700 | 12.4− | 37.2− | | | | | | |
| 26 JAN 0700 | 12.8− | 37.5− | | | | | | |
| 27 JAN 0700 | 10.9− | 33.3− | | | | | | |
| 28 JAN 0700 | 11.5− | 35.1− | 7.0 | | 3.77− | 92 | 27.2 | 32.1 |
| 29 JAN 0700 | 12.6− | 38.1− | | | | | | |
| 30 JAN 0700 | 12.8− | 36.0− | | | | | | |
| 31 JAN 0700 | 13.0− | 38.0− | | | | | | |
| 01 FEB 0700 | 12.8− | 36.8− | | | | | | |
| 02 FEB 0700 | 12.0− | 36.3− | | | | | | |
| 03 FEB 0700 | 12.8− | 38.1− | 8.7 | | 4.07− | 98 | 30.1 | 32.1 |

| DIFF (%)/MORPH: | POLYS | BND | LYM | MONO | EOS | BASO | OTHR | RBC | PLAT |
|---|---|---|---|---|---|---|---|---|---|
| REFERENCE | 42 | 0 | 10 | 0 | 0 | 0 | | | |
| RANGE | 81 | 5 | 47 | 10 | 8 | 2 | | | |
| 30 DEC 0800 | 54 | 20+ | 11 | 09 | 01 | 01 | 00 | OK | OK |
| 31 DEC 0700 | 58 | 26+ | 10 | 06 | 00 | 00 | 00 | OK | OK |
| 01 JAN 0700 | 52 | 21+ | 14 | 11+ | 01 | 01 | 00 | OK | OK |
| 10 JAN 0700 | 51 | 07+ | 30 | 05 | 02 | 02 | 00 | OK | OK |
| 28 JAN 0700 | 43 | 21+ | 27 | 07 | 01 | 01 | 00 | OK | OK |
| 03 FEB 0700 | 51 | 03 | 28 | 02 | 01 | 00 | 00 | OK | OK |

| MISC: | STOOL OB | RETIC CT % | EOS CT CELLS/MM3 | ESR MM/HR | FE UG/DL | IBC | FERRITIN NG/ML | B12 PG/ML | FOLATE NG/ML |
|---|---|---|---|---|---|---|---|---|---|
| REFERENCE | | 0.2 | 40 | 2 | 45 | 250 | G.T. | 200 | 3 |
| RANGE | | 2.5 | 423 | 20 | 200 | 350 | 20 | 900 | 16 |
| 30 DEC 0800 | | | | 40+ | | | | | |
| 11 JAN 1400 | − | 2.0 | | | 60 | 250 | | | |
| 12 JAN 0800 | + | 3.1+ | | | | | | | |
| 13 JAN 0800 | + | | | | | | | | |
| 15 JAN 0800 | − | | | | | | | | |

| COAG: | PTA SEC | APTT SEC | BT MIN | FIBRINO MG/DL | FDP MCG/ML |
|---|---|---|---|---|---|
| REFERENCE | 11.0 | 19 | 3 | 200 | L.T. |
| RANGE | 12.5 | 32 | 5 | 400 | 10 |
| 30 DEC 0800 | 11.2 | 21.8 | | | |
| 16 JAN 1500 | 11.8 | 23.0 | | | |

II. URINALYSIS

| ROUTINE: | APP | PH | SGR | SUG | ACET | PROT | BLD | BILE |
|---|---|---|---|---|---|---|---|---|
| 30 DEC 0800 | CLR | 8.5 | 1.007 | NEG | NEG | NEG | NEG | NEG |
| 31 JAN 1200 | CLR | 5.5 | 1.017 | NEG | NEG | NEG | NEG | NEG |

| MICRO: | WBC | RBC | BACT | CASTS | EPC | OTHR |
|---|---|---|---|---|---|---|
| 30 DEC 0800 | 0-2 | 0 | 0 | 0 | 0 | 0 |
| 31 JAN 1200 | 2-4 | 1-2 | 1+ | 0 | 2+ | 0 |

III. BASIC CHEMISTRY

| CHEM I: | GLU | BUN | CREA | Na | K | CL | CO2 | OSM(S) | OSM(U) |
|---|---|---|---|---|---|---|---|---|---|
| | MG/DL | | | MMOL/L | | | | MOSM/KG | |
| REFERENCE | 65 | 6 | 0.5 | 134 | 3.5 | 96 | 25 | 282 | 50 |
| RANGE | 140 | 25 | 1.7 | 145 | 5.5 | 110 | 32 | 296 | 1200 |

CHART XIV-continued

| | | | | | | | |
|---|---|---|---|---|---|---|---|
| 30 DEC 0800 | 103 | 9 | 0.8 | 142 | 4.2 | 93− | 34+ |
| 31 DEC 0700 | | | | 142 | 4.9 | 87− | 36+ |
| 31 DEC 1600 | | | | 138 | 4.2 | 88− | 38+ |
| 01 JAN 0700 | 110 | 14 | | 137 | 3.3− | 98 | 36+ |
| 01 JAN 0700 | | 11 | | 135 | 3.1− | 87− | 31+ |
| 02 JAN 0700 | | | | 135 | 3.2− | 90− | 32+ |
| 03 JAN 0700 | 128 | 23 | 1.2 | | | | |
| 10 JAN 0700 | | 16 | | 134− | 4.3 | 92− | 26 |
| 20 JAN 0700 | | | | 134− | 4.7 | 98 | 28 |
| 02 FEB 0700 | 80 | 7 | 0.4− | 142− | 5.5+ | 103 | 28 |

| A.B.G.: | PH | PCO2 PO2 MMHG | | O2 SAT % | CO2 MMOL/L | L/MIN % O2 O2 RX | |
|---|---|---|---|---|---|---|---|
| REFERENCE | 7.38 | 35 | 75 | 85.0 | 24 | | |
| RANGE | 7.42 | 45 | 85 | 95.0 | 30 | | |
| 30 DEC 0800 | 7.07− | 143+ | 76 | 86.0 | 44+ | | |
| 30 DEC 1000 | 7.45+ | 53+ | 371+ | 99.8+ | 38+ | | |
| 30 DEC 1400 | 7.48+ | 56+ | 57− | 90.5− | 43+ | | |
| 31 DEC 0800 | 7.52+ | 42 | 62− | 92.8− | 35+ | | |
| 01 JAN 0800 | 7.47+ | 48+ | 61− | 91.9 | 36+ | | |
| 01 JAN 1400 | 7.49+ | 46+ | 77 | 95.2+ | 36+ | | |
| 02 JAN 1000 | 7.52+ | 41 | 73− | 95.2+ | 35+ | | |
| 02 JAN 1400 | 7.52+ | 42 | 87+ | 96.8+ | 35+ | 45 | |
| 02 JAN 1500 | 7.51+ | 41 | 73− | 94.9 | 34+ | 40 | |
| 02 JAN 1900 | 7.44 | 49+ | 72− | 94.0 | 34+ | 50 | |
| 03 JAN 1200 | 7.38 | 57+ | 91+ | 95.9 | 35+ | | |
| 03 JAN 1400 | 7.47+ | 44 | 74− | 94.5 | 33+ | 40 | |
| 04 JAN 0900 | 7.45+ | 46+ | 67− | 92.8 | 33+ | 40 | |
| 04 JAN 2200 | 7.47+ | 44 | 65− | 92.8 | 33+ | | |
| 06 JAN 1100 | 7.31− | 69+ | 79 | 92.8 | 36+ | | |
| 06 JAN 1500 | 7.36− | 59+ | 72− | 92.4 | 34+ | | |
| 08 JAN 0100 | 7.42 | 55+ | 49− | 85.0− | 36+ | | |
| 08 JAN 1200 | 7.37− | 65+ | 47− | 80.1− | 39+ | | |
| 10 JAN 0800 | 7.37− | 67+ | 44− | 77.9− | 40+ | | |
| 10 JAN 1100 | 7.33− | 74+ | 39− | 70.0− | 40+ | | |
| 12 JAN 1200 | 7.26− | 90+ | 64− | 86.6 | 42+ | | |
| 12 JAN 1900 | 7.46+ | 53+ | 63− | 92.0 | 38+ | 50 | |
| 14 JAN 0900 | 7.54+ | 42 | 54− | 91.0 | 37+ | | |
| 14 JAN 2100 | 7.50+ | 45 | 50− | 88.0 | 37+ | | |
| 16 JAN 1300 | 7.50+ | 40 | 81 | 96.0+ | 33+ | 55 | |
| 18 JAN 1100 | 7.52+ | 40 | 66− | 93.7 | 34+ | | |
| 20 JAN 1100 | 7.44+ | 43 | 92+ | 96.5+ | 30 | | |
| 22 JAN 1300 | 7.42 | 42 | 82 | 95.2+ | 28 | | |
| 24 JAN 1000 | 7.34− | 55+ | 80 | 93.7 | 31+ | | |
| 26 JAN 1100 | 7.39 | 48+ | 72− | 92.8 | 30 | | |
| 26 JAN 1400 | 7.44 | 42 | 60− | 90.5 | 29 | | |
| 28 JAN 0600 | 7.48+ | 38 | 69− | 94.1 | 30 | | |
| 28 JAN 1100 | 7.40 | 42 | 56− | 87.8 | 27 | | |
| 30 JAN 1600 | 7.45+ | 37 | 79 | 95.0 | 27 | | |
| 02 FEB 1100 | 7.39 | 45 | 96+ | 96.2+ | 28 | | |
| 03 FEB 1300 | 7.47+ | 36 | 56− | 89.4 | 27 | | |
| 04 FEB 1300 | 7.40 | 39 | 67− | 91.9 | 25 | | |

| CHEM II: | CA | PO4 MG/DL | URIC | MG MEQ/L | AMY U/DL | LIP U | CHOL | TG MG/DL | HDL | LDL |
|---|---|---|---|---|---|---|---|---|---|---|
| REFERENCE | 8.8 | 2.0 | 2.5 | 1.0 | 5 | L.T. | 125 | 50 | 25 | 60 |
| RANGE | 10.8 | 4.7 | 8.5 | 2.2 | 37 | 1.0 | 300 | 200 | 75 | 185 |
| 30 DEC 0800 | 9.5 | 3.0 | 6.7 | | 20 | 0.5 | 205 | 160 | | |

| CHEM III: | BILT | BILD MG/DL | SAP | GGTP | SGPT | SGOT IU/L | LDH | CPK |
|---|---|---|---|---|---|---|---|---|
| REFERENCE | 0.1 | 0.0 | 10 | 1 | 1 | 1 | 90 | 0 |
| RANGE | 1.7 | 0.3 | 50 | 40 | 70 | 70 | 250 | 125 |
| 30 DEC 0800 | 0.9 | 0.2 | 40 | 35 | 40 | 25 | 100 | 100 |
| 22 JAN 1600 | | | | | 20 | 20 | 94 | 30 |
| 28 JAN 1100 | 1.2 | | 36 | | 26 | 26 | 90 | 37 |

| PROTEINS: | TP | ALB GM/DL | GLOB | ALPHA 1 | ALPHA 2 | BETA | GAMMA |
|---|---|---|---|---|---|---|---|
| REFERENCE | 6.2 | 3.6 | 1.9 | 0.15 | 0.50 | 0.60 | 0.60 |
| RANGE | 8.3 | 5.2 | 3.7 | 0.40 | 1.00 | 1.20 | 1.60 |
| 30 DEC 0800 | 6.1− | 3.7 | 2.4 | | | | |
| 28 JAN 0800 | 5.8− | 3.3− | 2.5 | | | | |

IV. SPECIAL CHEMISTRY

| HOSPITAL LAB: | TEST | RESULT | REFERENCE RANGE | UNITS |
|---|---|---|---|---|

CHART XIV-continued

| | | | | | |
|---|---|---|---|---|---|
| 30 DEC 0800 | ART | non-reactive | non-reactive | | |
| 30 DEC 0800 | T3 uptake(resin) | 32 | 25-35 | % | |
| 30 DEC 0800 | T4 thyroxin(RIA) | 6.8 | 4.5-12.5 | MG/DL | |
| 08 JAN 0800 | DIGOXIN(RIA) | 0.8 | 0.8-2.0 | NG/ML | |
| REFERENCE LAB: | TEST | | RESULT | REFERENCE RANGE | UNITS |
| 03 JAN 0800 | CEA | | 5.00[1]* | .00-2.50 | NG/ML |
| 08 JAN 0800 | ALPHA 1 ANTITRYPSIN | | 200 | 80-260 | MG/DL |
| 12 JAN 1400 | FACTOR VIII | | 90 | 50-200 | % AC |
| 12 JAN 1700 | HEMOGLOBIN, PLASMA | | 4 | 0-7 | MG/DL |
| 12 JAN 1700 | HEMOGLOBIN, FREE, URINE | | NEG | NEGATIVE | |
| 12 JAN 1700 | HAPTOGLOBIN | | 140 | 25-180 | MG/DL |

[1]*Plasma CEA titers are not an absolute test for malignancy. In the management and diagnosis of the patient suspected or known to have cancer, all other tests and procedures must continue to be given emphasis. CEA titers less than 2.5 NG/ML are not proof of the absence of malignant disease.

V. MICROBIOLOGY

| | ORIGIN | MICRO EXAM | CULTURE | SENSITIVITIES |
|---|---|---|---|---|
| 30 DEC 0800 | CSF | NEG | NO GROWTH | |
| 31 DEC 0800 | URINE | | NO GROWTH | |
| 02 JAN 0800 | STOOL | WNL | NORMAL FLORA | |
| 11 JAN 0800 | BLOOD | NEG | NO GROWTH | |
| 11 JAN 0900 | BLOOD | NEG | NO GROWTH | |
| 11 JAN 1000 | BLOOD | NEG | NO GROWTH | |

The patient test data in Chart XIV above is the same data which was displayed in over 40 pages of computer print out in a prior art system.

INTRODUCTION TO FLOWCHARTS

FIGS. 4-39 show flow charts that illustrate the operation of the system of FIGS. 1-3. More specifically, these flowcharts illustrate how cumulative patient reports are generated by the subject invention as part of a system providing for the generation, storage and reporting of medical test data for a clinical laboratory and ancillary testing areas servicing a continually changing patient population.

The symbols in the flow charts are keyed to the files and reports of FIG. 1 or to other portions of the flow charts. The processing associated with a flow chart process block is either described fully within that individual process block, for example 85, or is summarized in a defined process block, for example 86, with a reference annotation defining the flowchart figure providing the detailed illustration of the processing summarized in the defined process block. The entry point symbol at the top of the detailed illustration contains a mnemonic abbreviation of the processing being performed. This mnemonic abbreviation is used as identification of the defined process at the top of the defined processing block in the referencing flow chart. When a predefined process is terminated by an exit flowchart symbol containing RETURN, processing resumes at the next processing block in the original referencing flow chart.

SYSTEM CONTROL

As indicated by the flow charts, the system initially consists of a single initialization process enabled upon system power up. This initialization process enables a configuration dependent number of processes, one each per console in the system. A console may be a CRT display 46; a keyboard printer pair 32,44; an automated laboratory equipment communications link 34; or a telecommunications interface with an outside laboratory 36. Installation dependent system adaptation defines the number of consoles and the system functions accessible by each console.

Control passes to the system on power up at the SYSTEM POWER ON entry point 87, FIG. 4. System initialization processing causes the system controller hardware to be initialized 86 and the Diagnostic Data System Control Program (DDSCP) to be loaded and verified along with its data base 88. The date and time are then entered, validated 89 and maintained 90. Each input/output device in the installation specific equipment configuration is initialized 91 to the Console Menu Input Mode. For each console, the system initiates processing whenever either of the following two conditions occurs. First, once every five seconds control is transferred to entry point CONSOLE TIMER 92, FIG. 8, in order to monitor console activity. If the console is in the Console Menu Input Mode, the input/output interface is reinitialized thus providing for automatic establishment of communications with interfaced equipment as it is placed on line. If the console is not in Console Menu Input Mode and has not been used for over five minutes, the console is automatically returned to Console Menu Input Mode, thereby limiting the potential for unauthorized or inadvertent access to patient data contained in the system. Second, when in Console Menu Input Mode, input from a console will cause processing to be initiated at entry point CONSOLE-MENU-INPUT 93. A valid input, i.e., one of the menu selections defined as accessible by that console as part of the configuration specific system adaptation, will cause processing to be initiated at the entry point for the associated system function 94 through 101. The processing associated with each of the various system functions is described separately below.

SYSTEM FUNCTIONS

Test Request Entry Function

Figure 10:
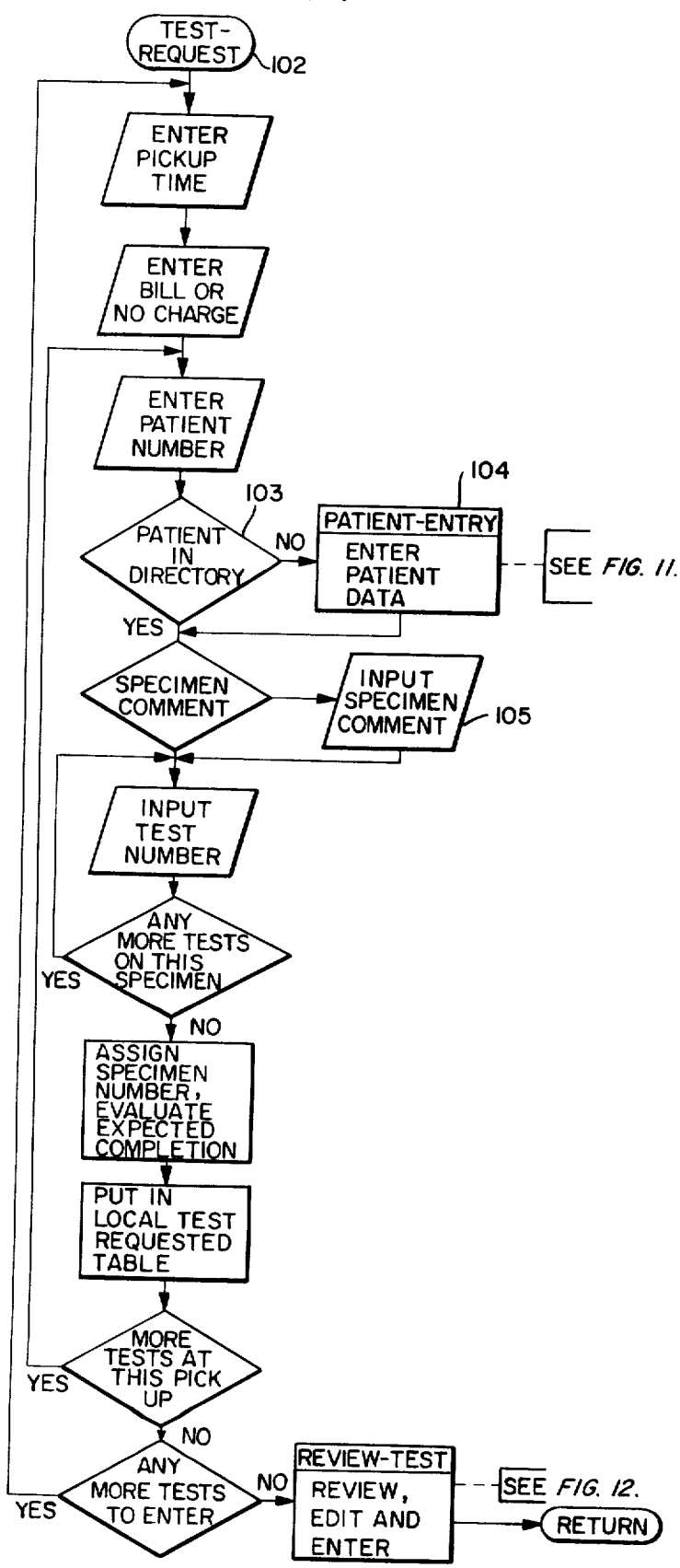

Test Request Entry processing begins at entry point TEST—REQUEST 102, FIG. 10, upon operator input of the associated menu selection. The processing shown in FIG. 10 provides for efficient on line entry of multiple test requests per patient in an otherwise unstructured stream of test requests. Patient numbers are validated against the patient directory 103. Test request processing provides for the on line entry of a new patient into the patient directory or register when the first test request for this patient is received in the laboratory 104. Specific specimen handling instructions may be added at entry time 105 if indicated on the test request 2. Test type is input by test codes which are encoded to include one or more check digits. Entry of test requests for one or more patients is followed by a verification operation starting at 106, FIG. 12. Quality control procedures generally require that each entered test request be verified for correctness. The operator is allowed to edit individual test requests as required prior to entry into the system test request file. When a complete set of test requests has been verified, it is added to the system test request file 8. At this time, specimen numbers are assigned by the system and expected completion dates established. Multiple individual tests may be replaced by batteries of tests where cost savings are possible. Also at this time, laboratory utilization data and cost accounting data are added to their respective files. Utilization data is provided to meet the College of American Pathologists (CAP) requirements on clinical laboratories.

Figure 11:
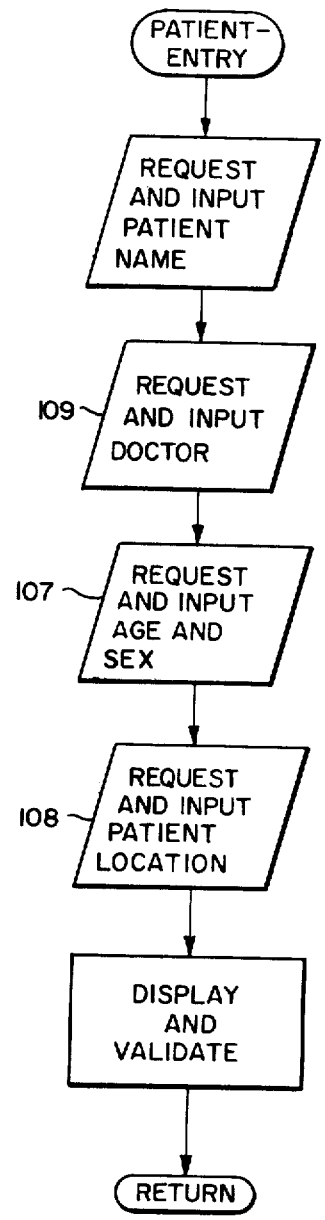
Figure 12:
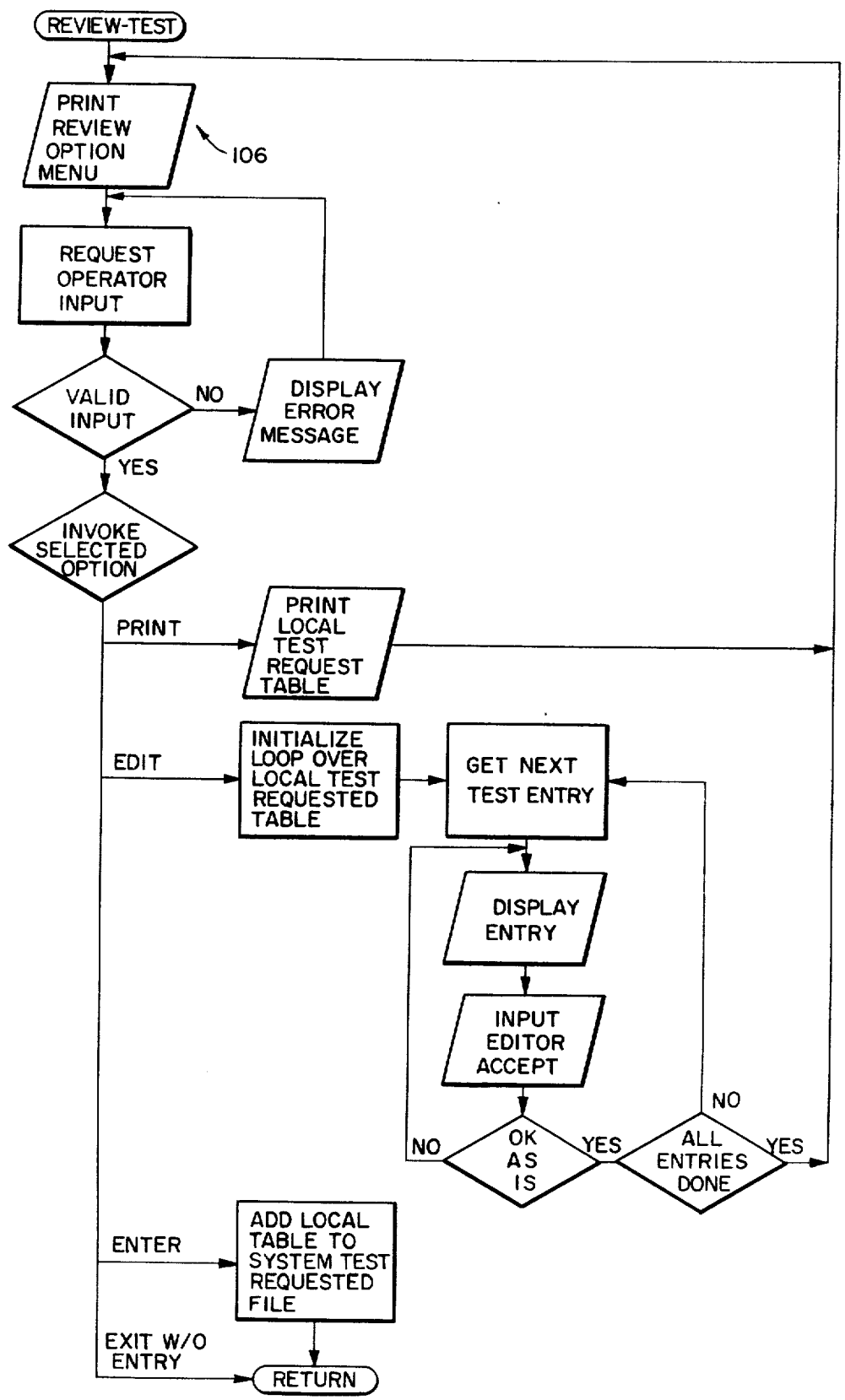

Patient data entry as illustrated in FIG. 11 provides for the input of key administrative and laboratory control data for each new patient. The patient data entered includes patient name, age and sex for proper reporting of test normal values, patient location and sufficient additional identifying data, such as physician's name, to support the data retention and retrieval requirements placed on clinical laboratories.

REPORT GENERATION PROCESSING FUNCTION

Figure 13:
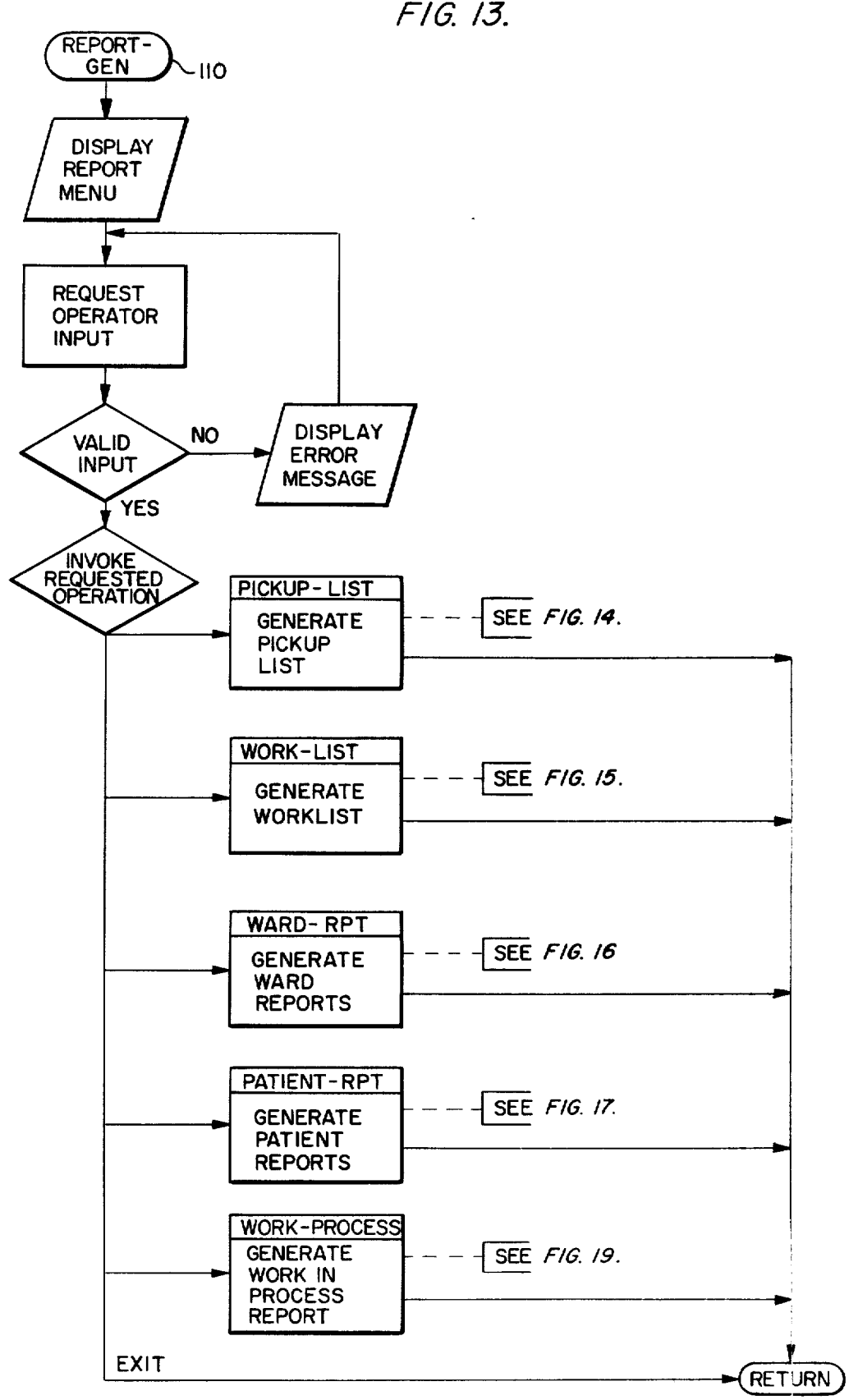

Report Generation processing begins at entry point REPORT—GEN 110, FIG. 13, upon operator input of the associated menu selection. Using this system function, the operator may select one of five report types to be generated and printed on a high speed line printer. These reports include the specimen pick up list, the laboratory work list, the ward report, the patient report and the work in progress report.

Figure 14:
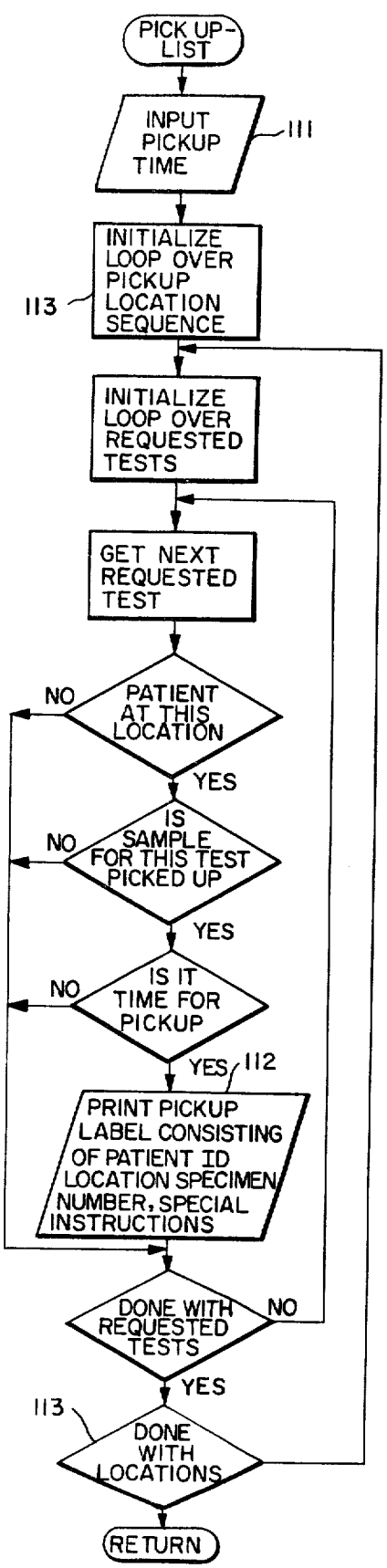

The processing associated with the generation of the pick up list report is as shown in FIG. 14. The operator inputs a pick up time 111. The system then generates a set of specimen labels 112, one for each specimen due on or before the input pick up time. The labels are printed in an installation dependent order based on patient location 113.

Figure 15:
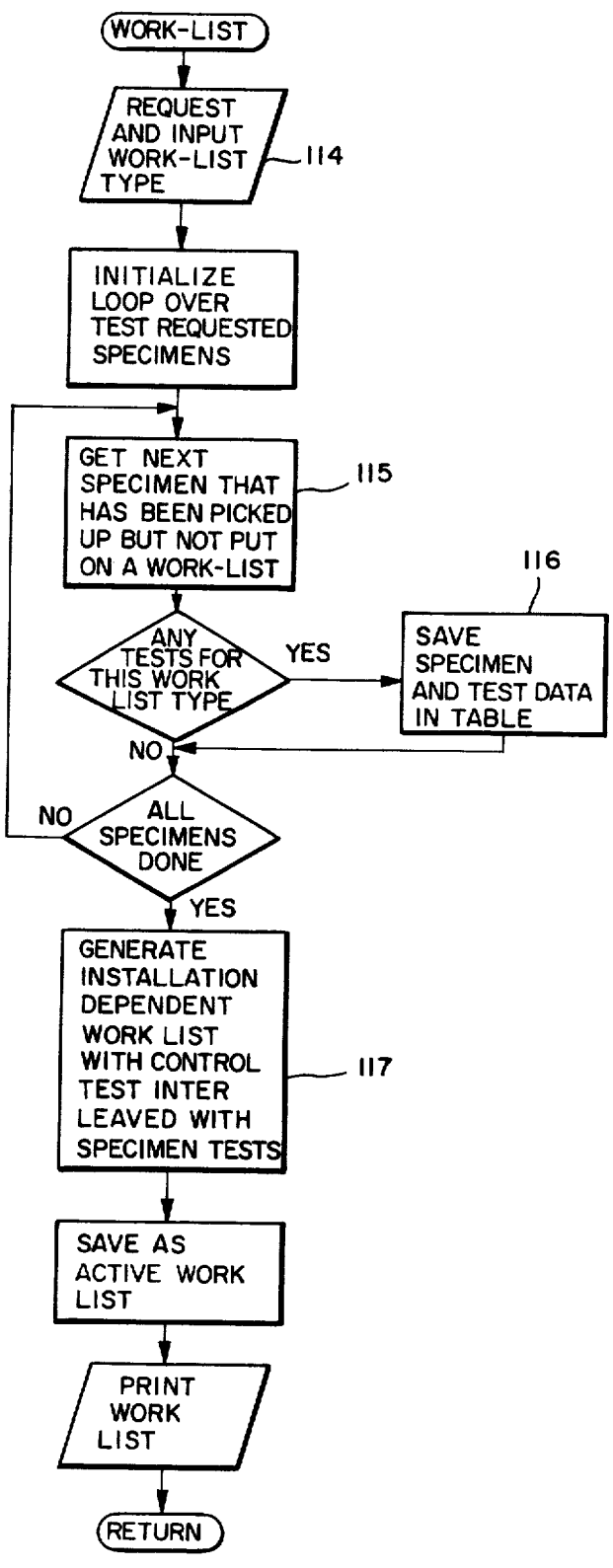

The processing associated with the generation of work list reports is as shown in FIG. 15. The work list report type is input by the operator from a list of installation specific work stations 114. The file of requested tests is examined to locate all instances where a test of the type performed at the specific work station has been requested and the specimen has been listed on a pick up list but the test has not yet appeared on a work list 115. The test type and specimen number of each such test are added to the work list 116. The complete work list is generated by interleaving the requested patient tests with quality control tests as required by laboratory quality control requirements. The work list is printed for use by laboratory personnel at each work station to define the specimens to be used, to specify the tests to be run, and to serve as a test result data sheet for those test results recorded manually. The work lists are retained in the system for efficient entry of the tests results in the order they appear on the work list report.

Figure 16:
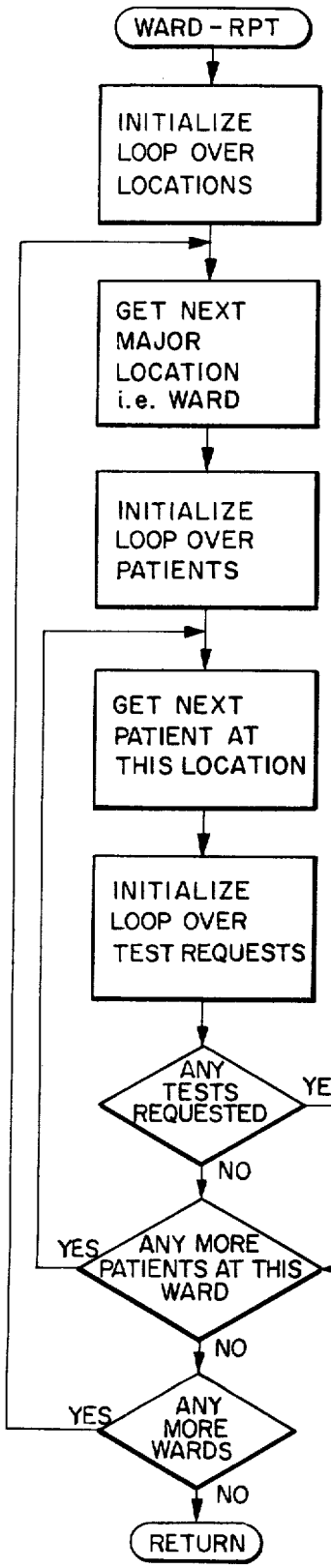
Figure 24:
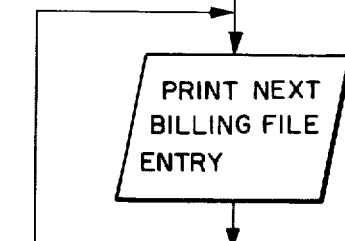

The processing associated with the generation of the ward report is as shown in FIG. 16. This report provides the work personnel with the status of any tests that have been requested but have not yet been reported in a patient report. The report indicates that the test is in progress or provides the results of that test.

Figure 17:
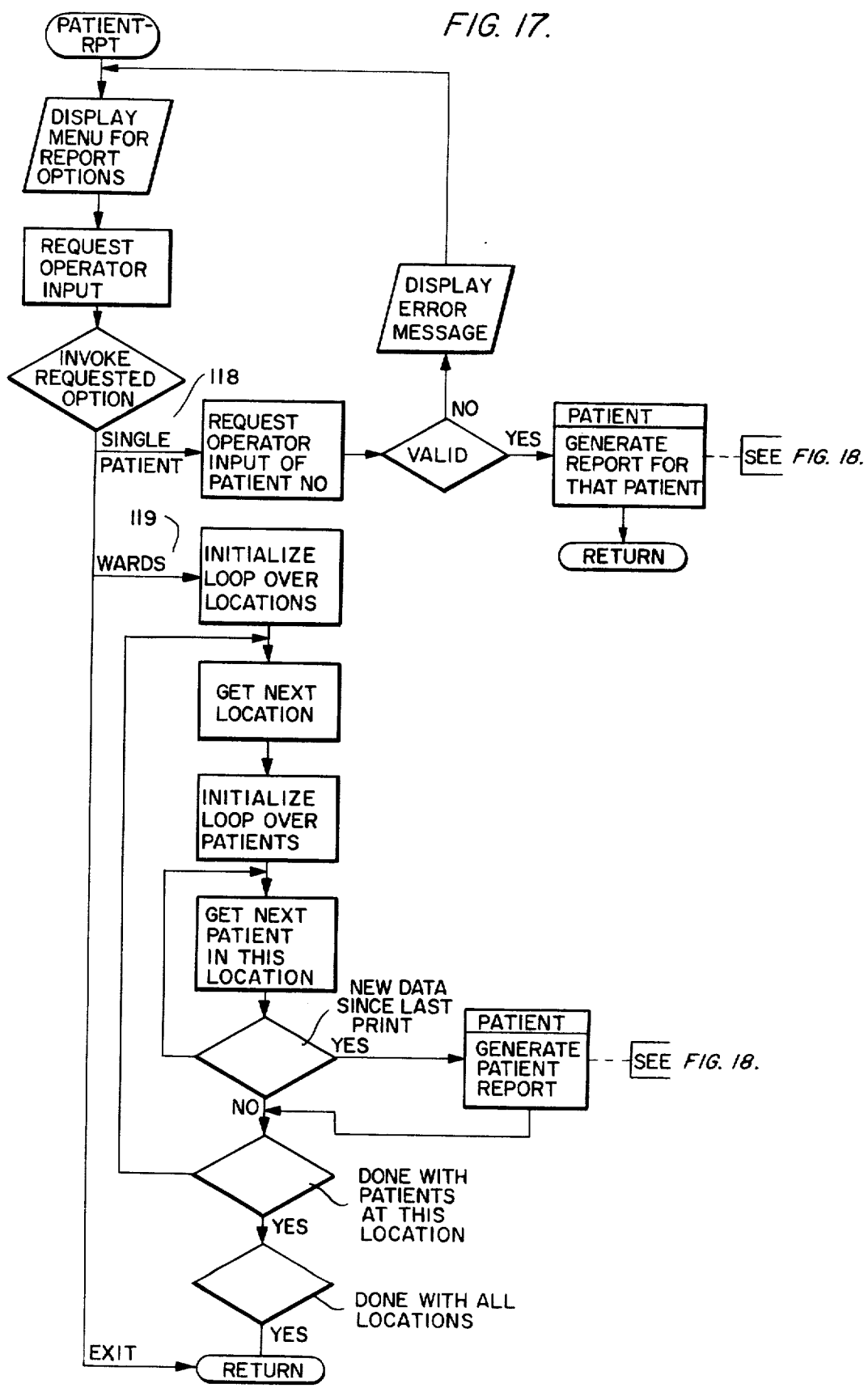

The patient report is generated as shown in FIG. 17. The operator may select printout of either a single patient report 118 or the complete patient population. Whenever a single patient report is requested, it is printed regardless of whether any new data has become available since the last printout. When the patient population option is selected, reports are printed only for those patients that have had new test requests and/or results entered since the last report was printed. As in the generation of pick up lists, the the patient reports are generated in patient location order for ease of distribution to the various wards serviced by the clinical laboratory and ancillary testing areas.

Figure 18:
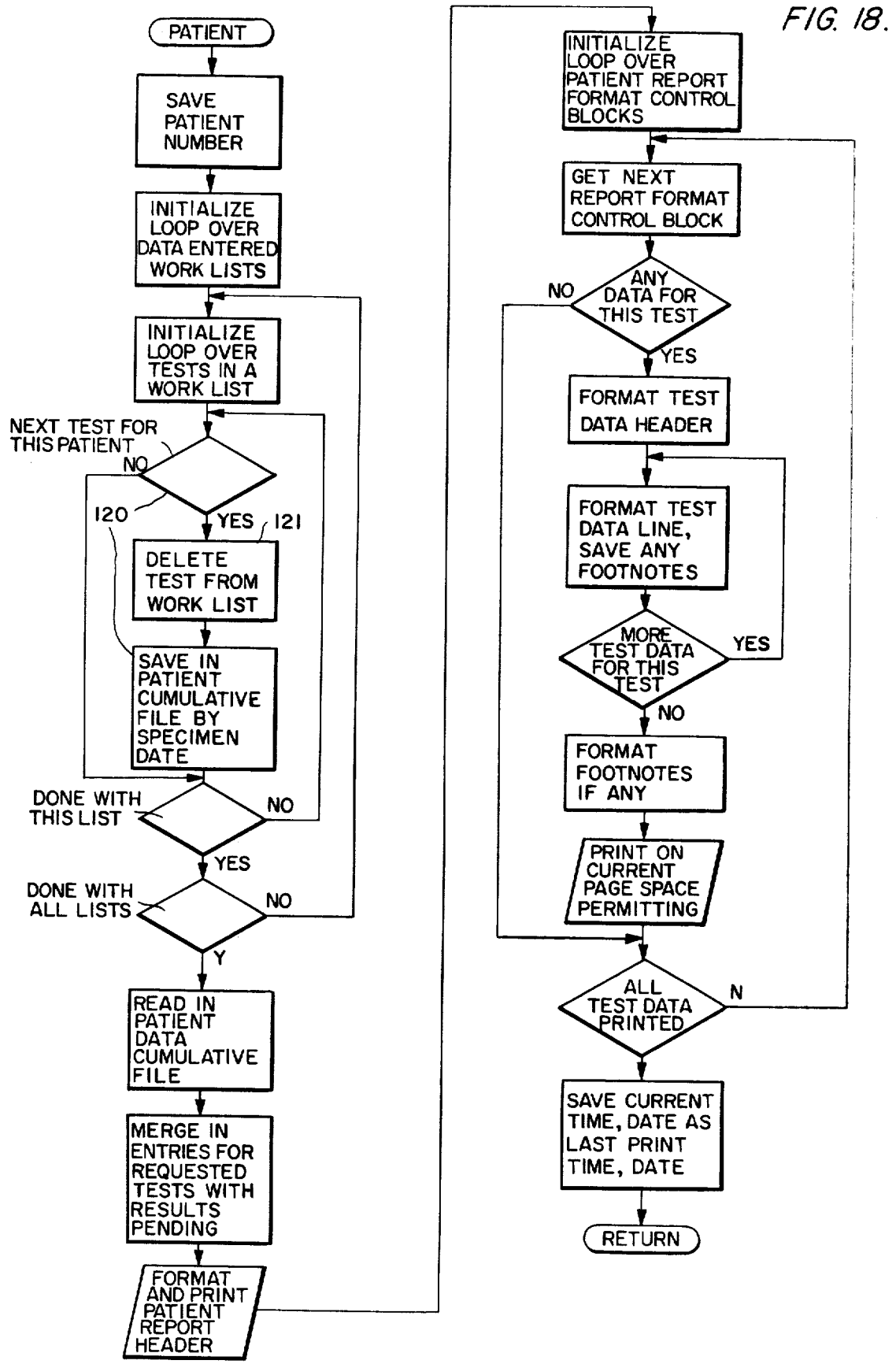

The detailed processing associated with the generation of the patient cumulative test report is shown in FIG. 18. The first operation is to locate all new data for a given patient and save it in the patient's cumulative test result file 120. As each result is added to the patient file, the associated work list entries are deleted as they are no longer needed 121. Entries are added to the report for pending test requests that have not yet been completed. The report is formatted by interpretation of a prespecified sequence of report format control blocks by the Diagnostic Data System Control Program. The report formal control blocks define the sequence of data reporting, the format of the label and nominal value printouts and the selection of line format control blocks used to format individual lines of data output. The report format control blocks and line format control blocks may be modified during system maintenance as illustrated later in FIG. 35 and FIG. 36 to reflect changes in installation dependent test capabilities, for example, addition of a new or deletion of an obsolete special chemistry category IV test.

Figure 19:
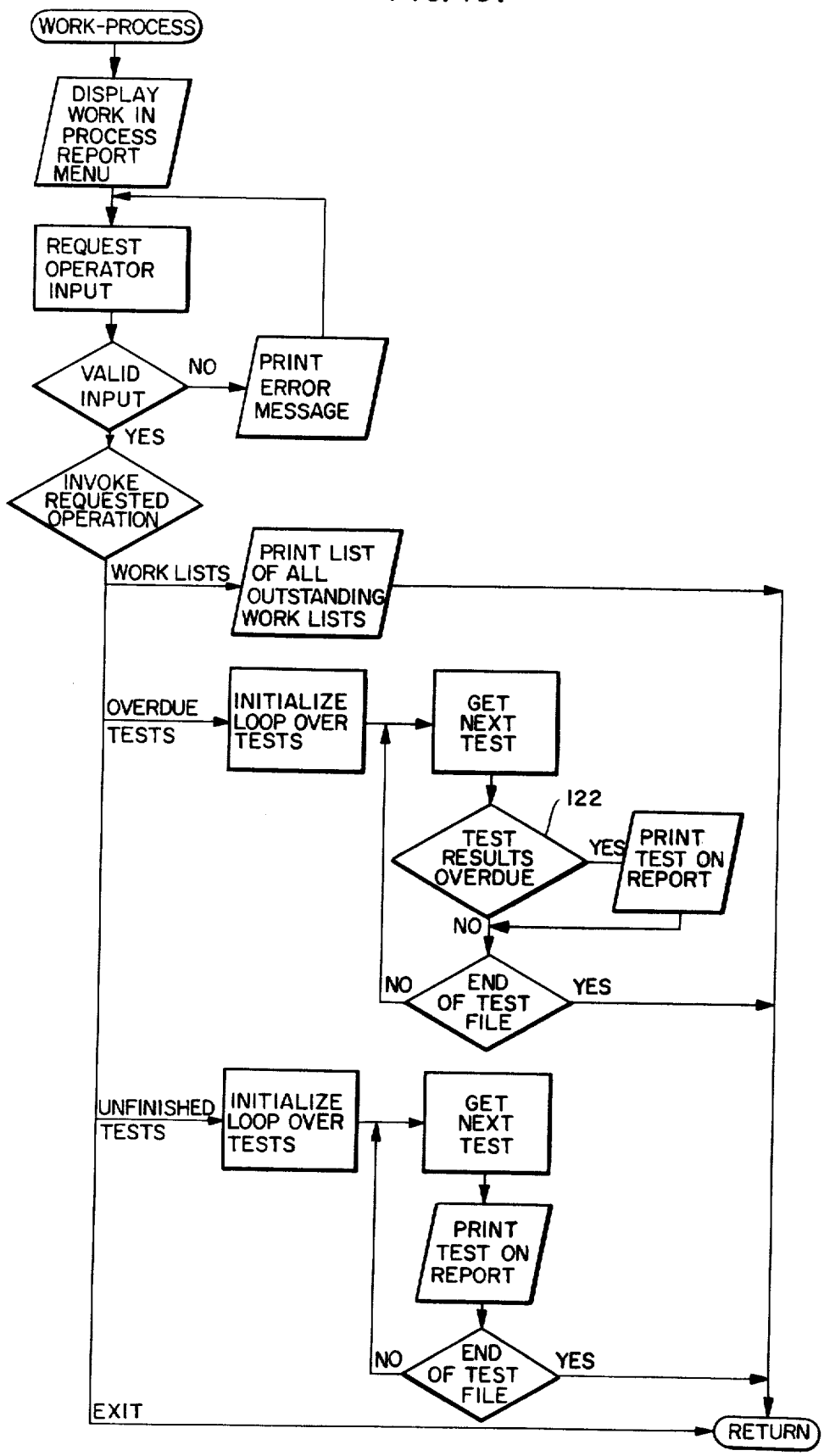

The Work In Process Report is generated as shown in FIG. 19. The operator selects from among the available options listed. The determination that a test is overdue 122 is based on the expected completion time/date as evaluated by test request processing. The other processing illustrated in FIG. 19 is self explanatory.

TEST RESULTS ENTRY PROCESSING FUNCTION

Figure 20:
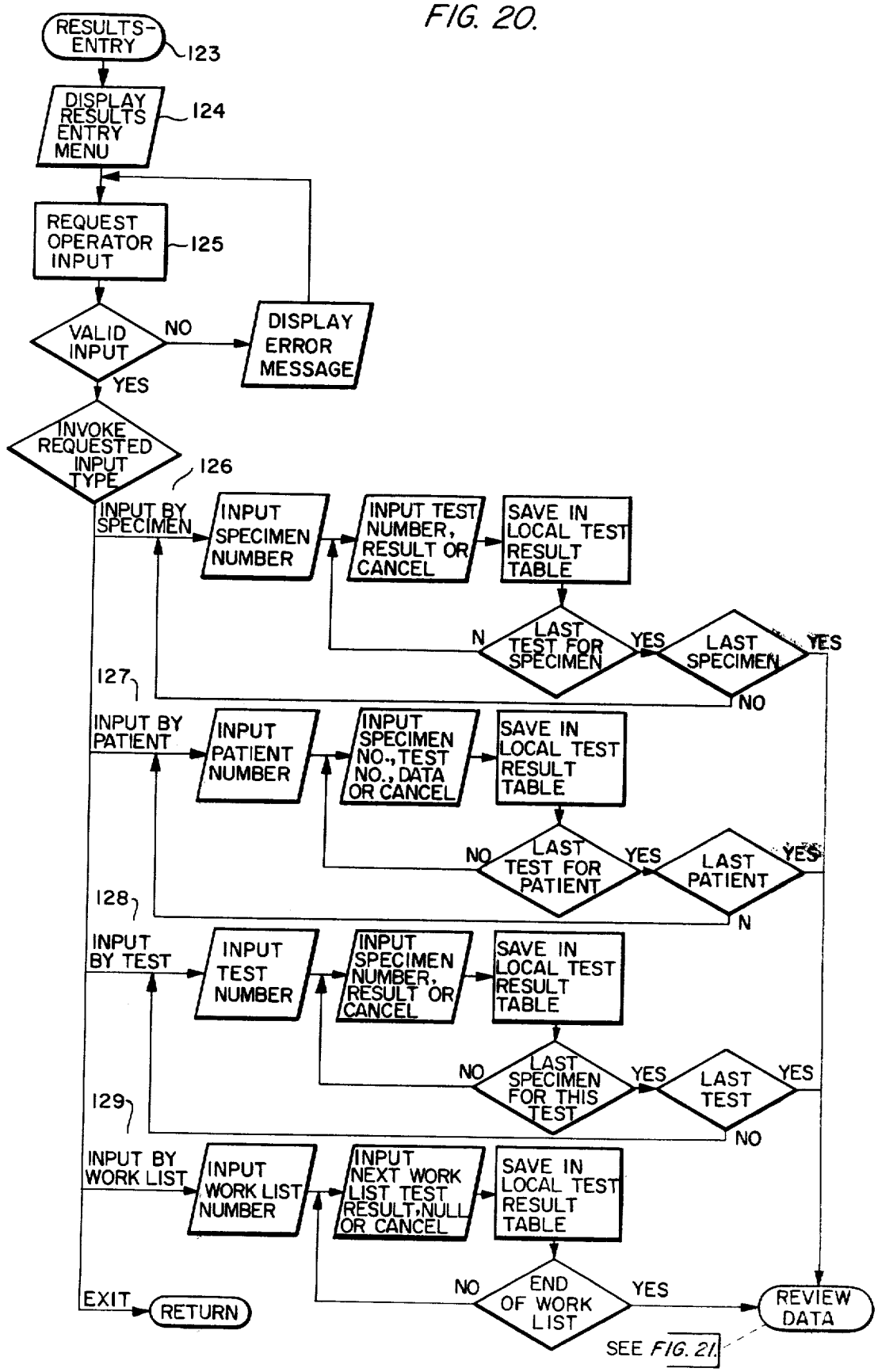
Figure 21:
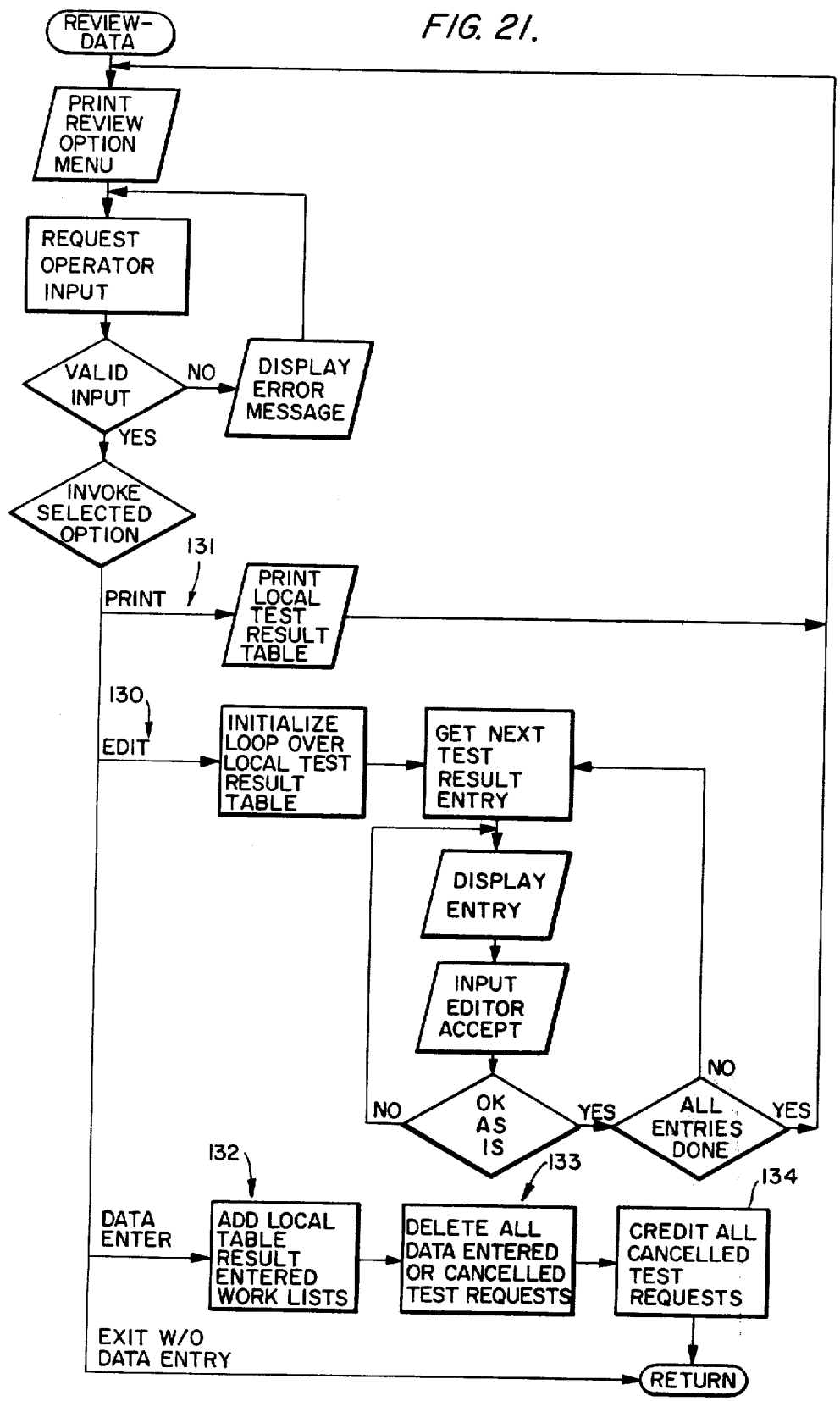

Test results entry processing begins at entry point RESULTS—ENTRY 123, FIG. 20, upon operator input of the associated menu selection. The available modes of test result entry are presented in menu form 124 for operator selection 125. Input of test data may be made by specimen 126, patient 127, test 128 or work list 129. Work list results entry is the most efficient method of input as the system retains the work list specimen and test sequence allowing the actual keystroked inputs to be limited to the test results themselves. At the conclusion of test data entry, a validation step is provided as shown in FIG. 21. On line review and editing may be performed 130. A hard copy printout 131 may be obtained. Subsequent to validation, the results are entered into the system as completed test results 132 and the associated pending test requests are deleted 133 from the system test request file. Any tests that are cancelled during test result entry are flagged for credit in the cost accounting file. Editing displays and hard copy printouts are annotated with alerts when individual test results exceed the reasonable test range tolerance or test-to-test max variance tolerance of the test definition 135, FIG. 34.

TEST STATUS, DATA INQUIRY AND EDITING FUNCTION

Figure 22:
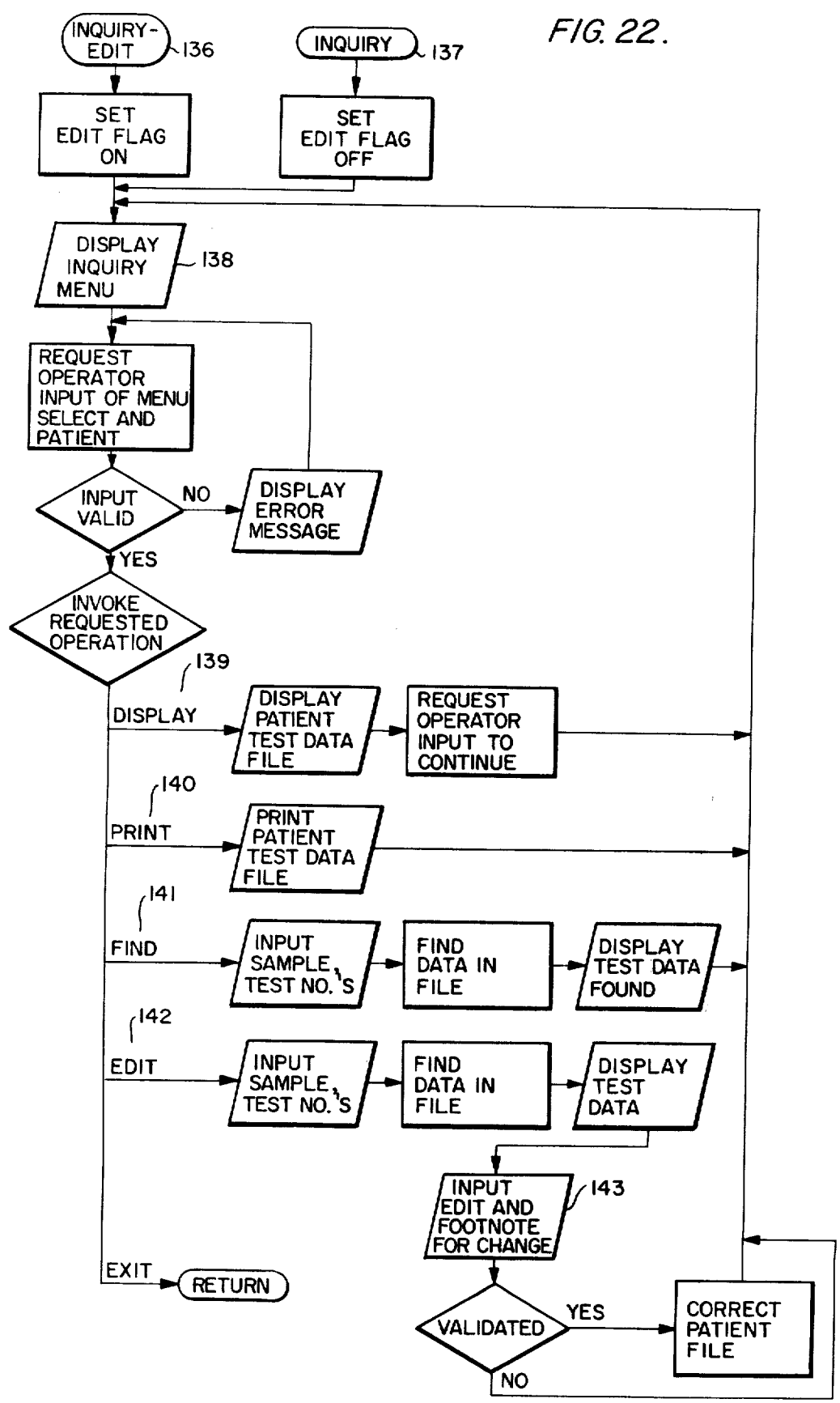

The test status and data inquiry processing begins at entry point INQUIRY 136, FIG. 22. The test status Inquiry and edit processing begins at entry point INQUIRY—EDIT 137, FIG. 22. The only difference between these two system functions is that access to the data editing menu selection 138 is limited to the test status inquiry and edit function and is therefore limited to those consoles having predefined access rights to that processing function. The DISPLAY menu selection 139 allows the operator to examine the patient test results report on a CRT display. The PRINT menu selection 140 causes a patient report to be generated per FIG. 17. This function reproduces the single patient report generation capability of FIG. 13 for those consoles that do not have access to the Report Generation system function. The FIND menu selection allows the operator to determine the current status of a requested test. The EDIT menu selection provides the means to update individual test results in the Patient Result File 22. Each update requires footnoting 143 for quality control auditing of test result changes after initial validation and entry.

LABORATORY SUPPORT FUNCTION

Figure 23:
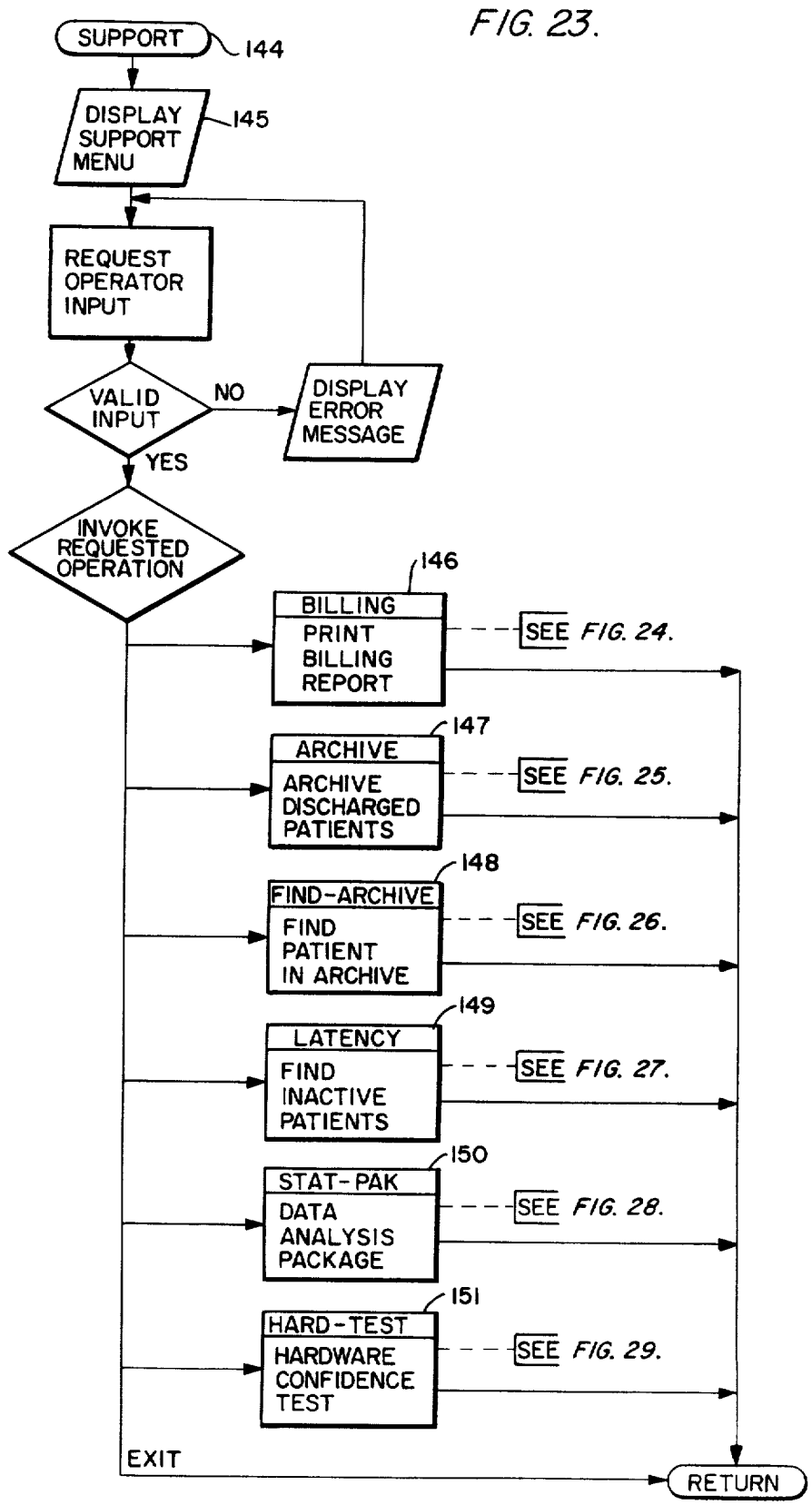
Figure 25:
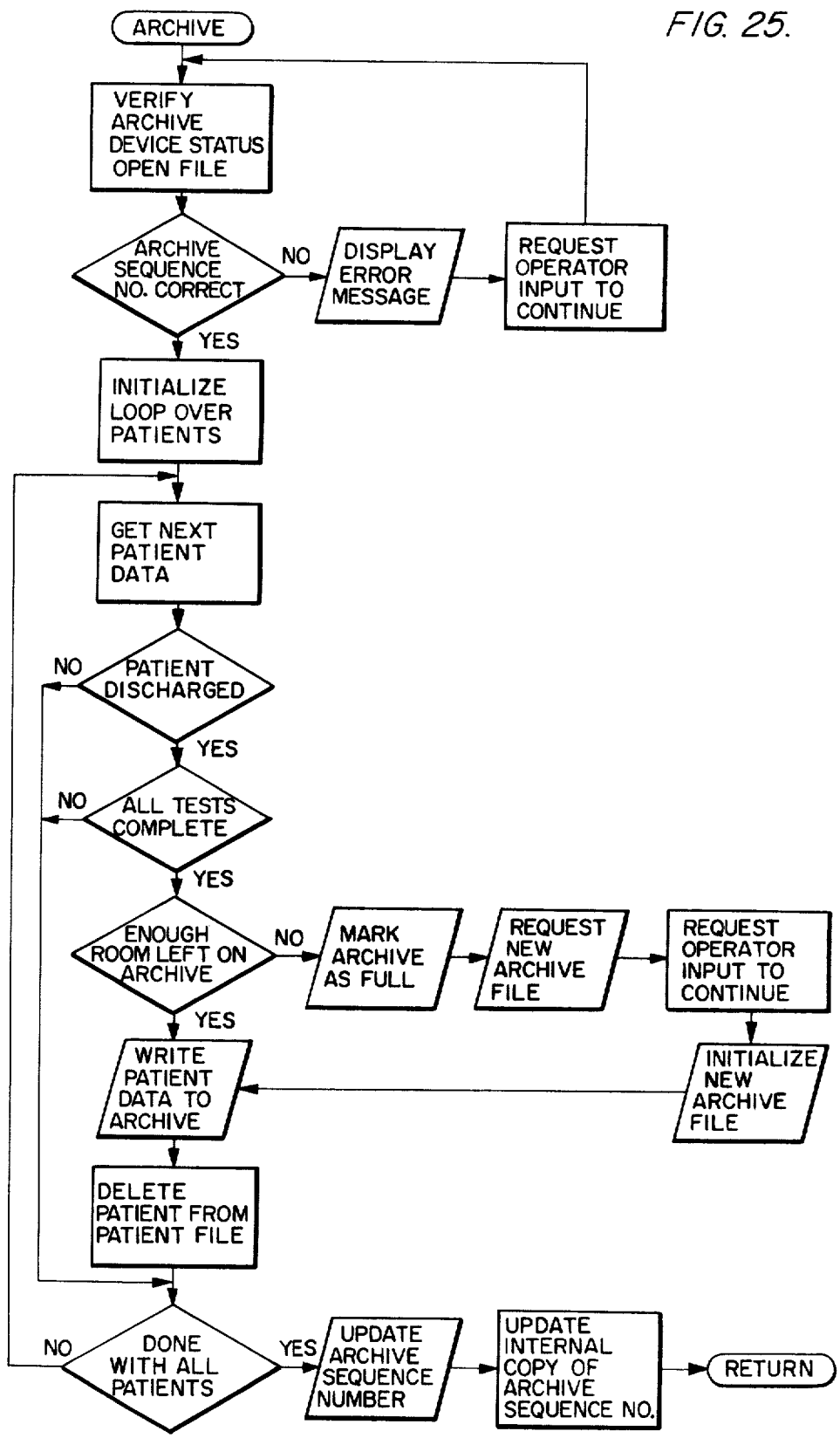
Figure 26:
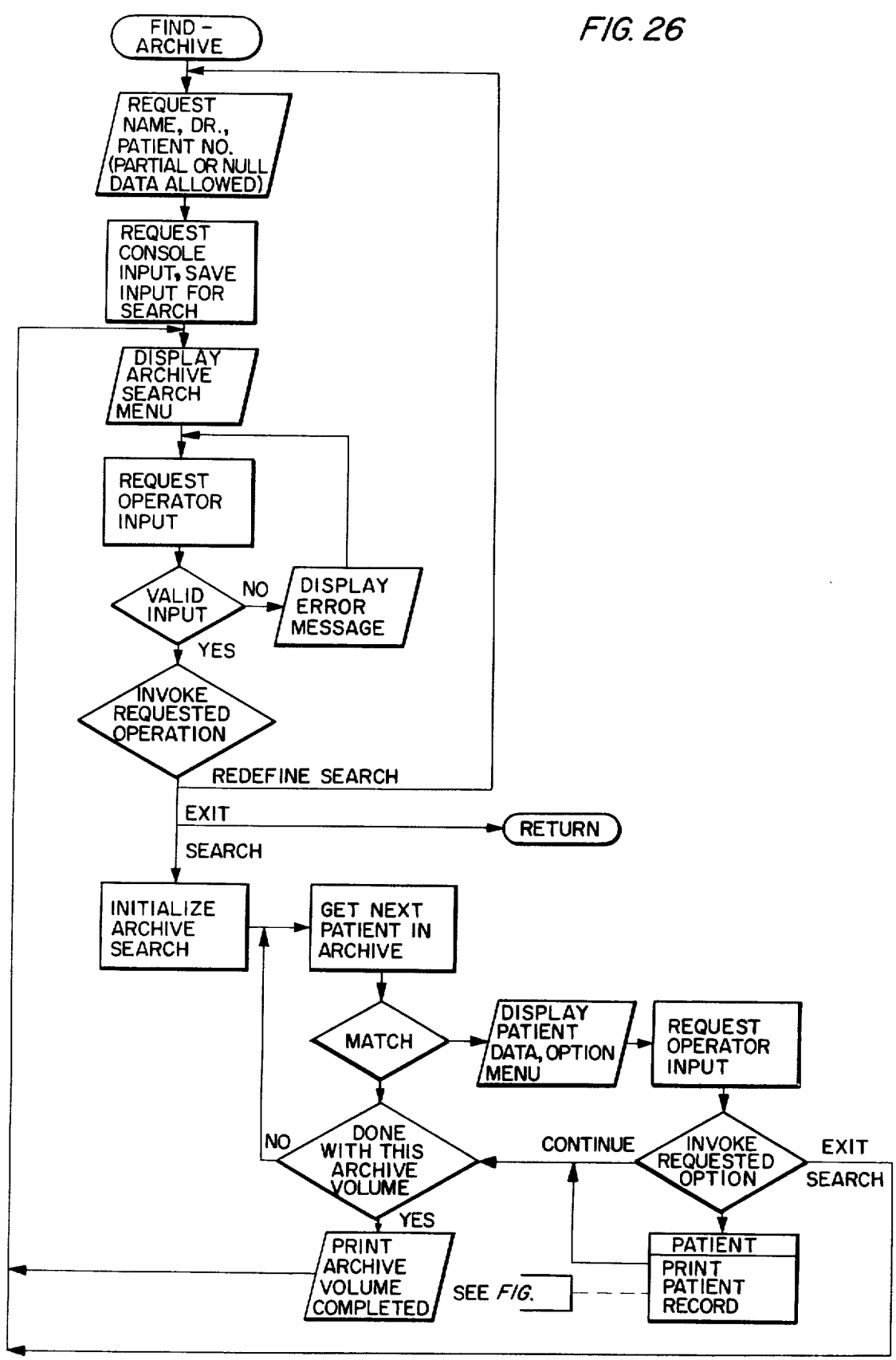
Figure 27:
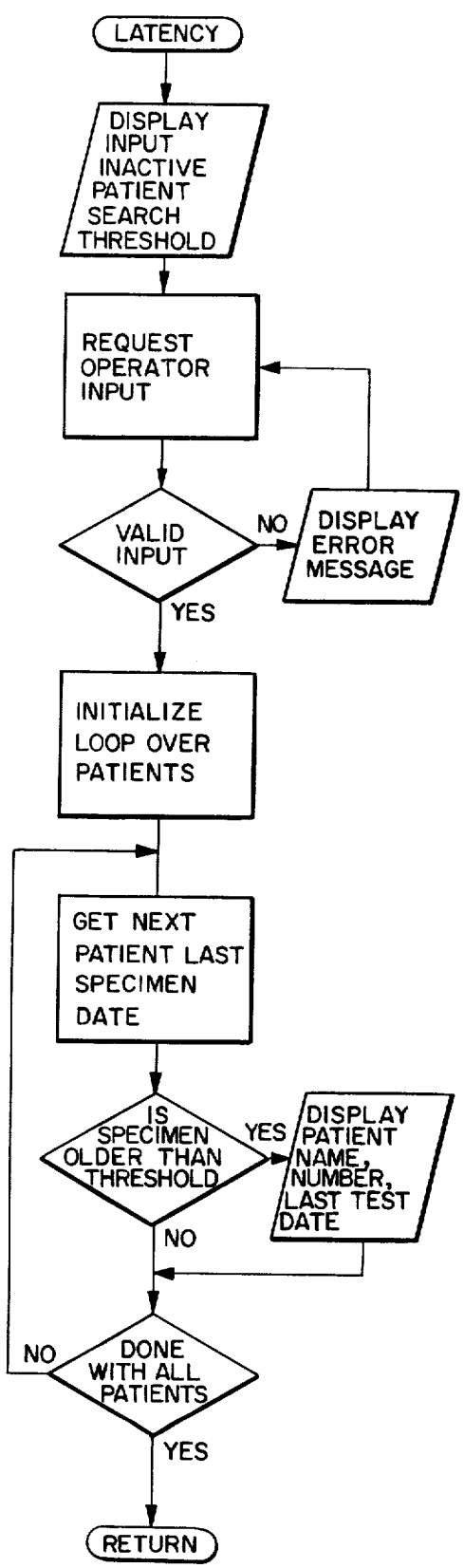
Figure 28:
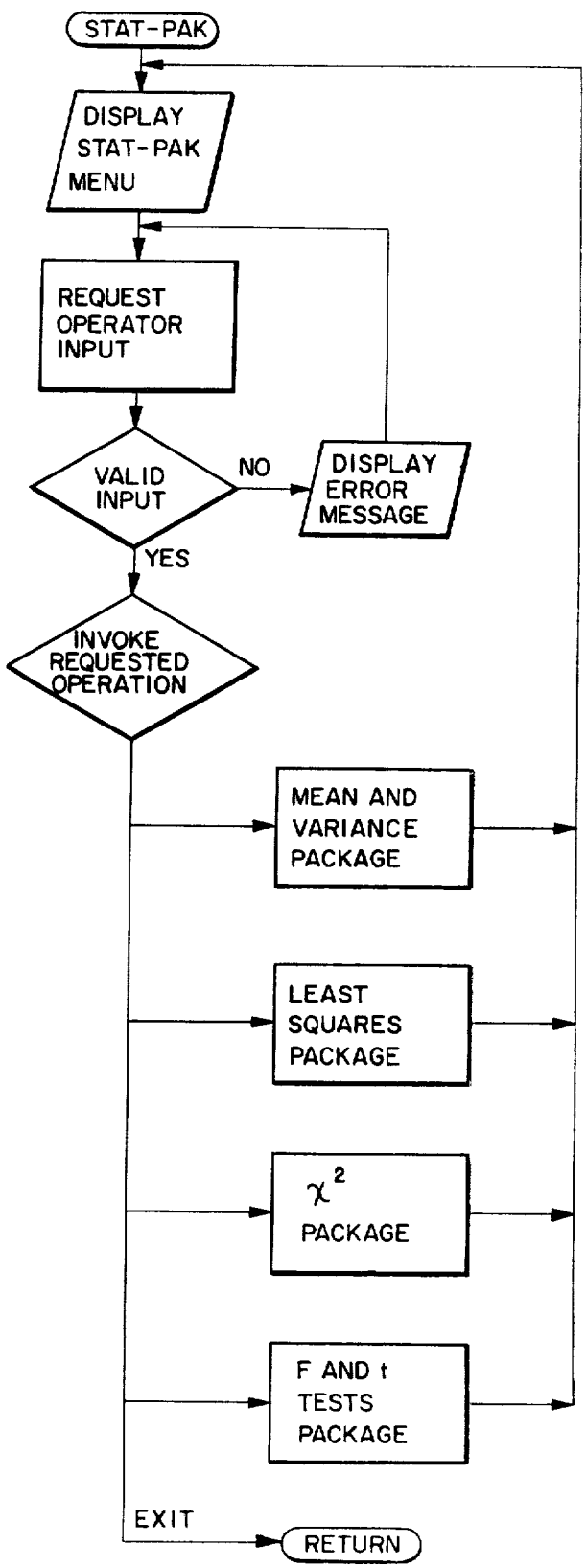
Figure 29:
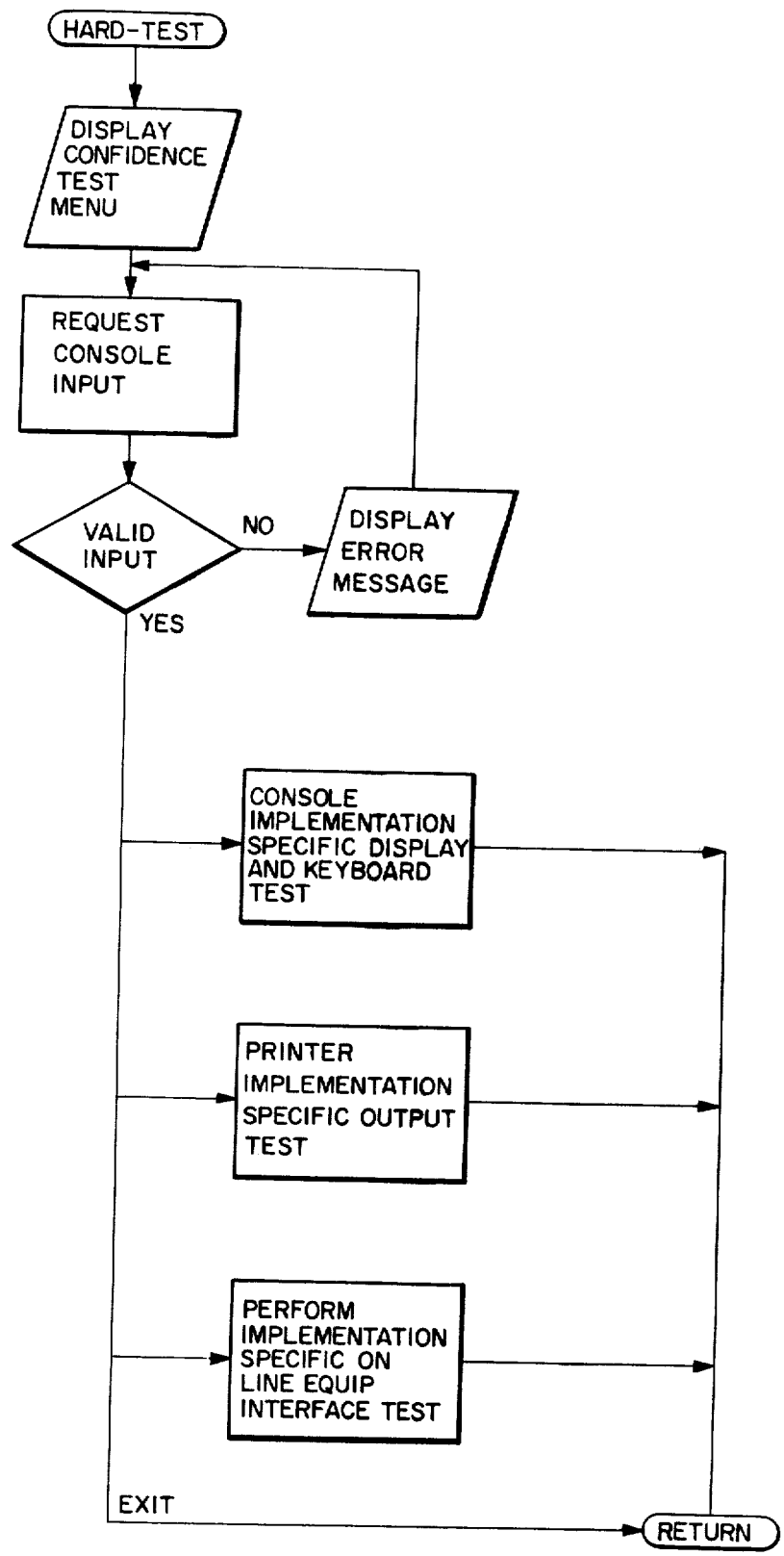

The Laboratory Support processing provided by the Diagnostic Data System Control Program begins at entry point SUPPORT 144, FIG. 23, upon operator input of the associated menu selection. The capabilities provided by this function support routine operation of the clinical laboratory. The laboratory support menu 145 provides six operator selections. The BILLING menu selection 146 provides for operator initiated output of the laboratory cost accounting file in report form. On an installation dependent basis this report may be provided on machine readable output media for direct input into the cost accounting data processing system. The menu selections ARCHIVE 147 and FIND-ARCHIVE 148 allow the operator to transfer all patient test data to the Archive Files 28 when the patient is discharged and to recall that data upon request. The LATENCY menu selection 149 allows the operator to search the patient file for inactive patients. This capability is used to find and archive discharged patients. The STAT-PAK menu selection 150 provides the laboratory staff with an on-line data entry and analysis package in support of the data analysis and data reduction tasks commonly performed in a clinical laboratory. The hardware confidence test menu selection 151 provides a set of installation dependent tests for the on-line verification of proper functioning of individual CRT's, keyboards, printers and other interfaced equipment.

SYSTEM MAINTENANCE FUNCTION

Figure 30:
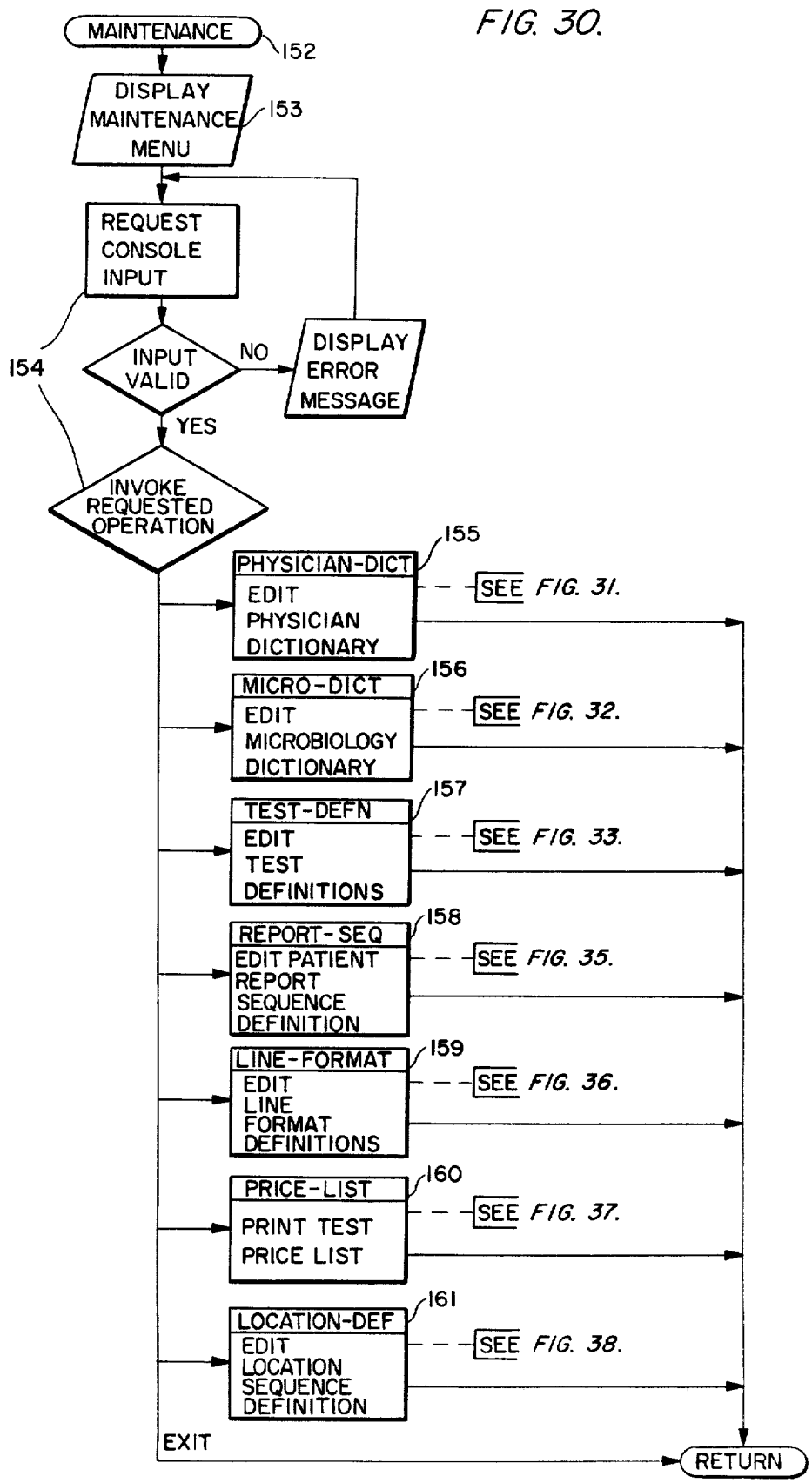
Figure 31:
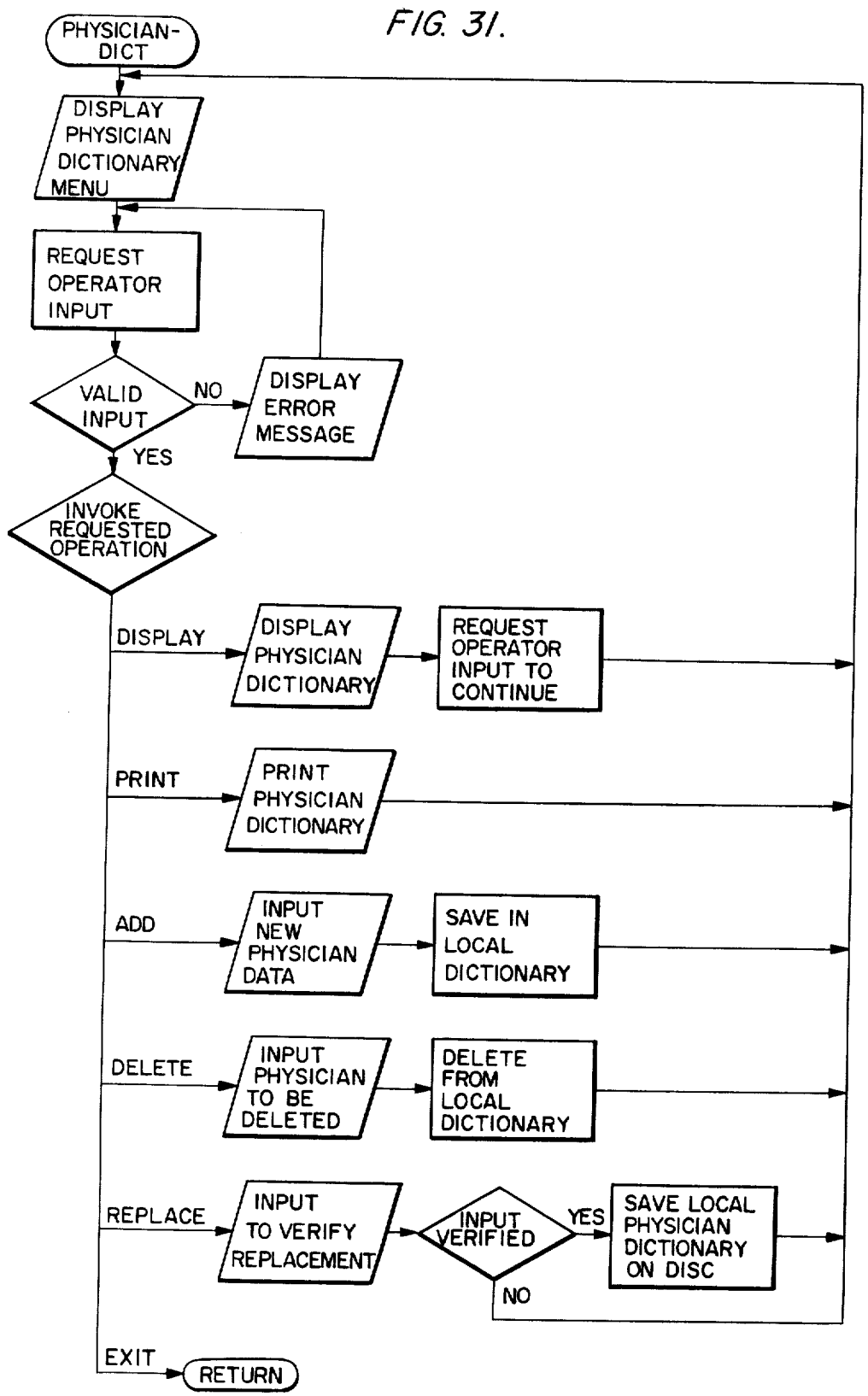
Figure 32:
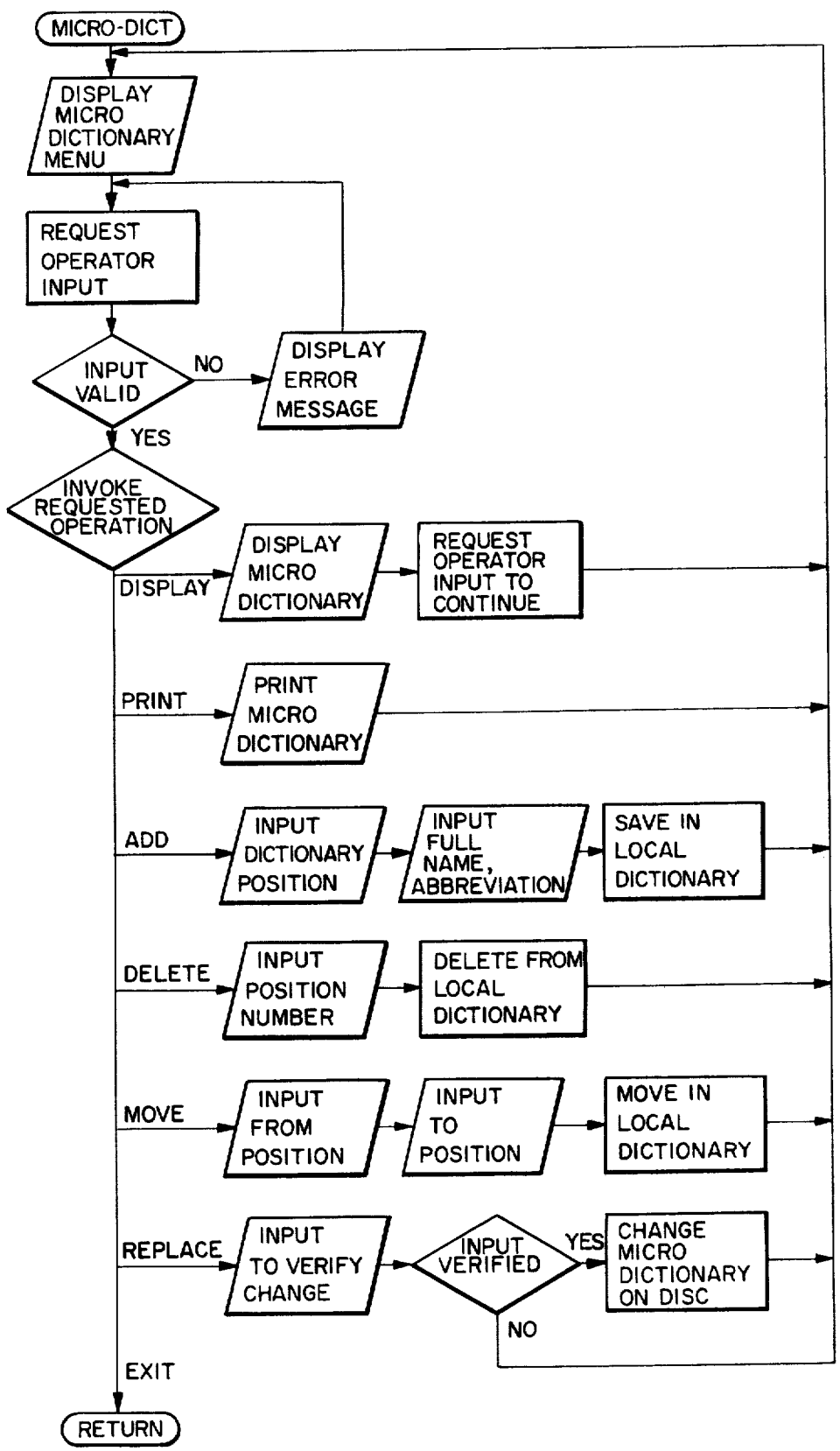
Figure 33:
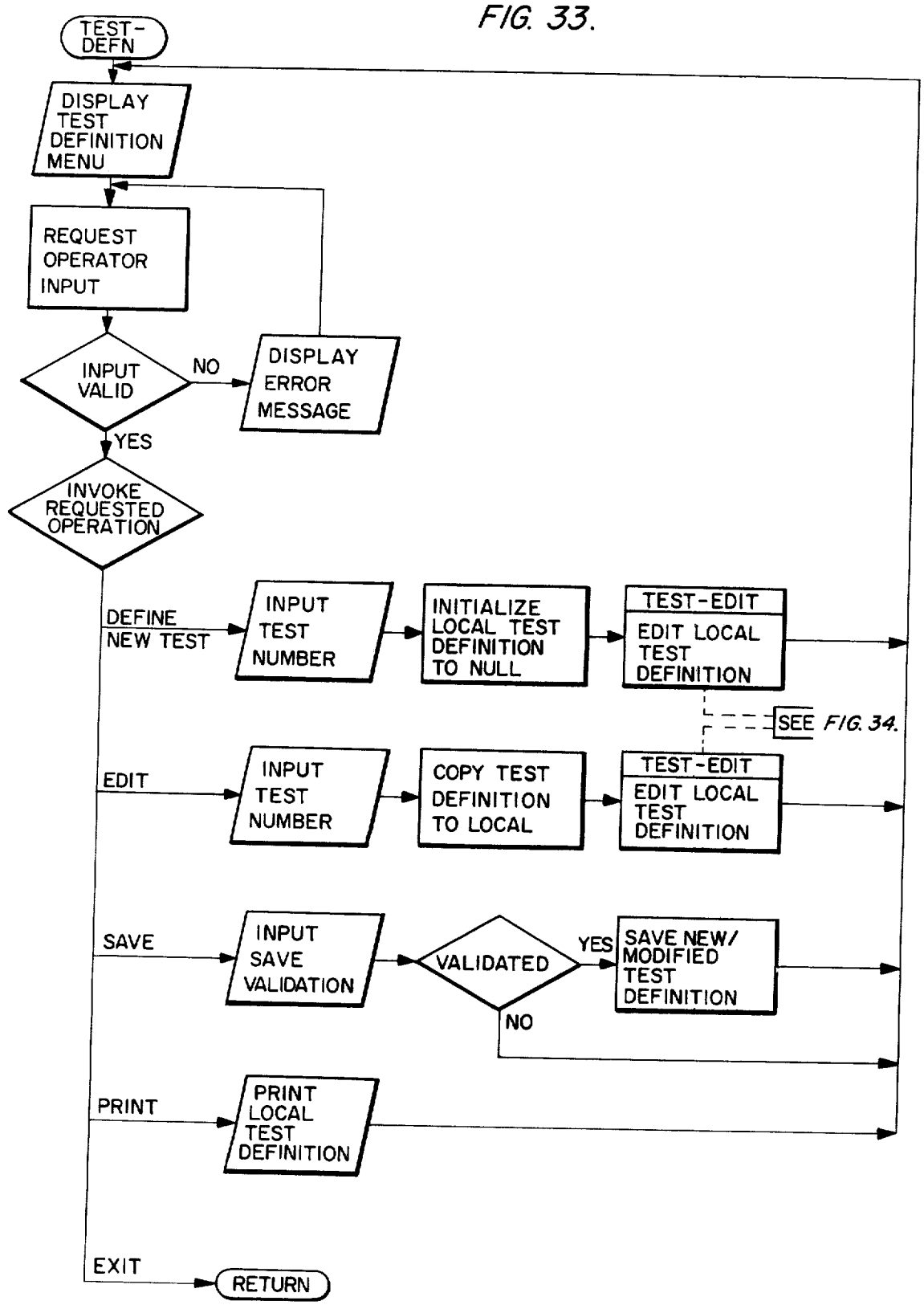
Figure 34:
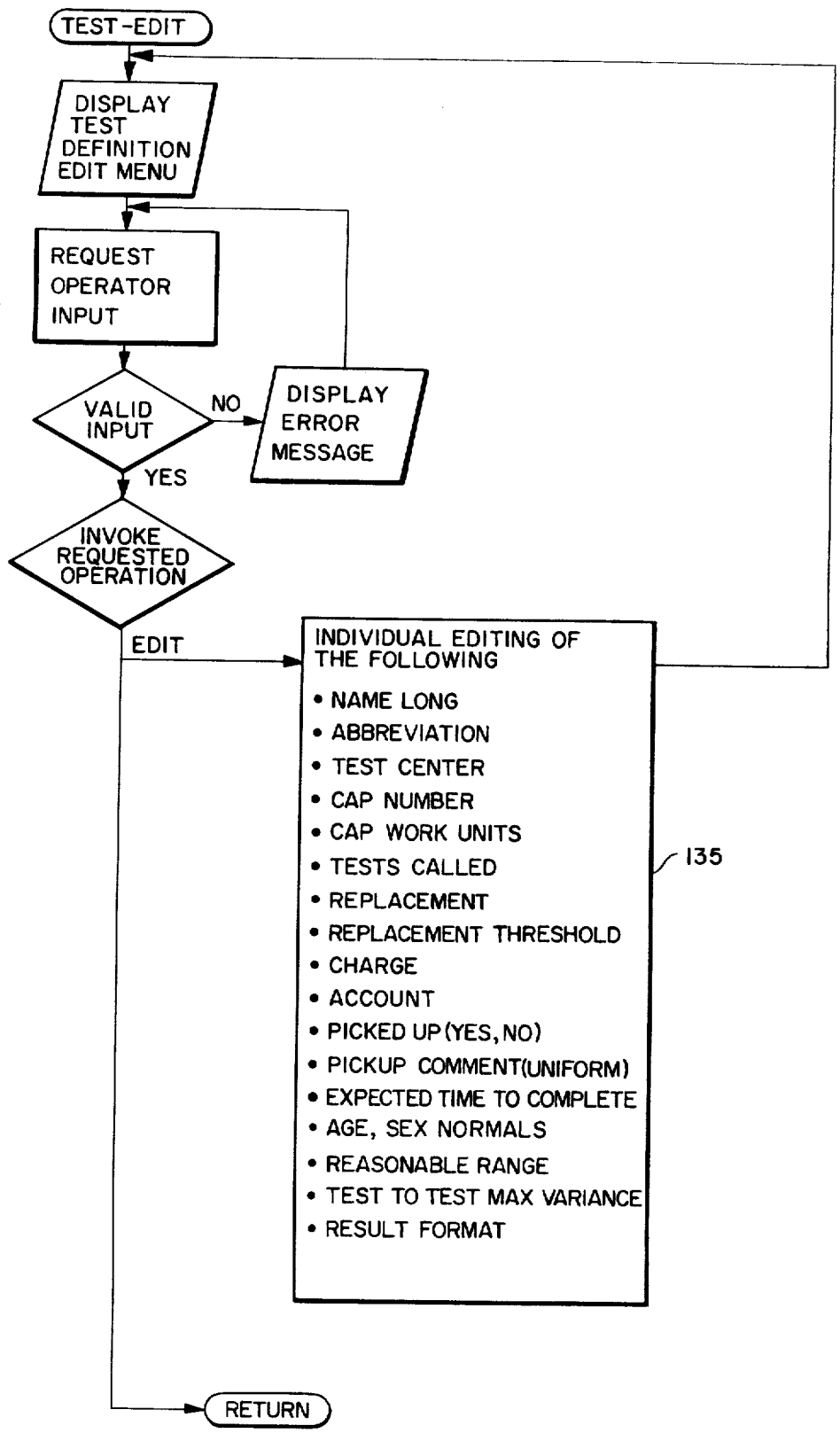
Figure 35:
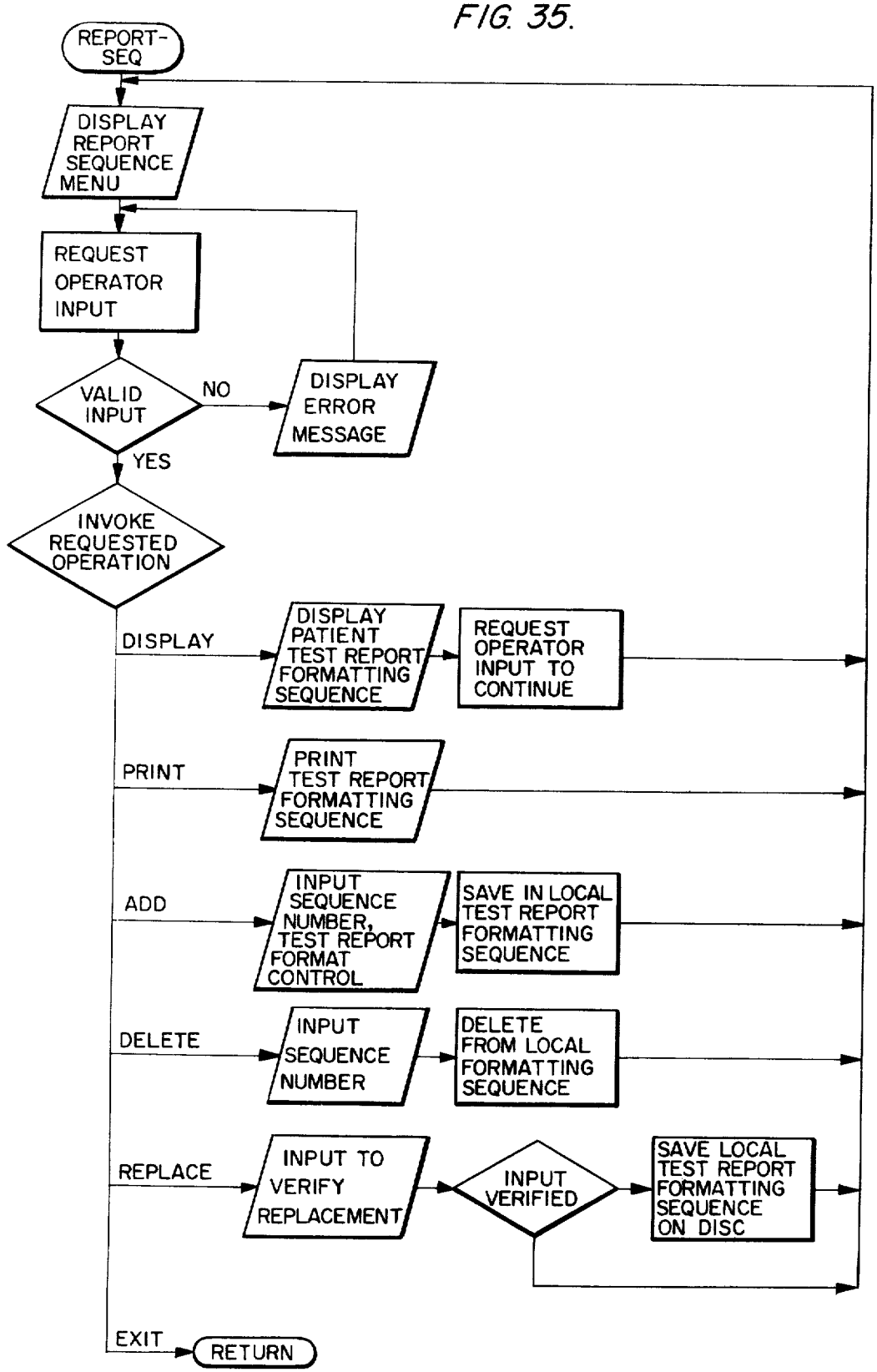

System maintenance processing begins at the entry point MAINTENANCE 152, FIG. 30, upon operator input of the associated menu selection. The maintenance functions available to the operator are displayed in menu form 153 for input selection 154. The Edit Physician Dictionary menu selection allows the laboratory personnel to add, delete or modify dictionary entries as shown in FIG. 31. The physician dictionary entries are used to validate the physician input field in the patient register. The Edit Microbiology Dictionary menu selection 156 allows the hospital staff to update the order and content of the Category V drugs of choice for each of the various infective organisms identified by the laboratory. Each infective organism in the dictionary is followed in descending order of preference by drugs of choice for use against that partcular organism. The occurrence of a particular drug both in the Microbiology dictionary and in the list of sensitivity results of the microbiology test causes a preferred treatment recommendation to be generated on the patient report. A dictionary for the relative daily costs of the antibiotics of choice may also be included.

The Edit Test Definition menu selection 157 allows laboratory personnel to edit existing test definitions or add new tests as they become available. The definition of a test includes the data items 135 identified in FIG. 34. College of American Pathologics (CAP) data is used to automate laboratory utilization reports. Replacement data provides for the minimization of cost by replacing multiple tests by inclusive batteries of tests at lower cost. Result formats include footnotes selectively added to the patient report based on result data that is outside of upper and/or lower tolerances for the test.

The Patient Report Sequence and Line Format Editing menu selections allow the laboratory staff to adapt the patient report to new tests, predominately special chemistry category, to update footnoting controls for the addition or deletion of footnotes associated with specific tests, and to provide for range and/or units changes due to changes in laboratory equipment, methods and outside services.

The Print Test Price List menu selection 160 causes the current price for each test in the test definition library to be printed. The Edit Location Sequence menu selection 161 provides laboratory personnel with a means of updating the location sequence used to order the printout of Pick Up Lists and patient reports for efficient handling of specimen pick up and report distribution tasks.

UTILIZATION AND QUALITY CONTROL SUPPORT FUNCTION

Figure 36:
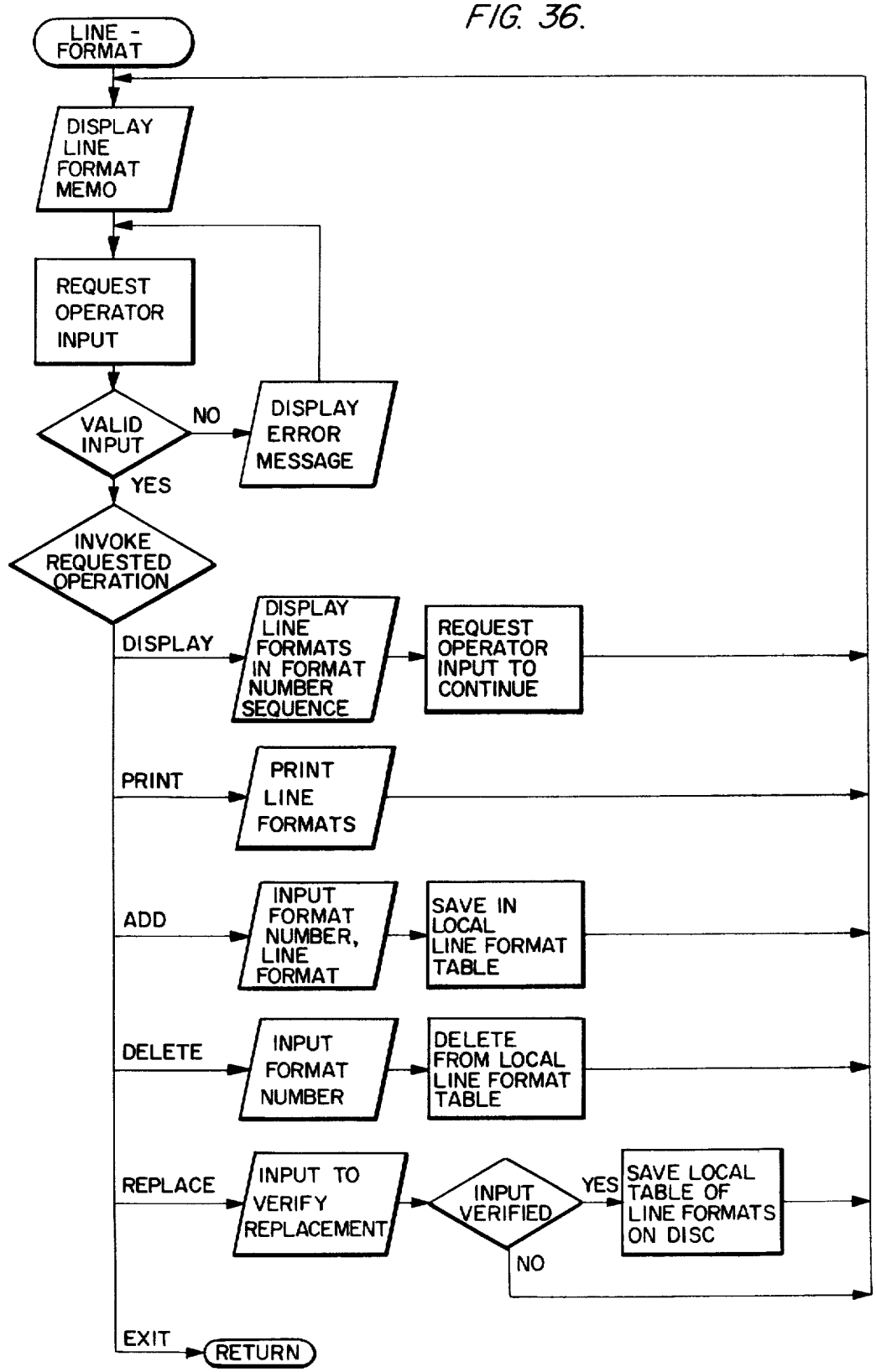
Figure 38:
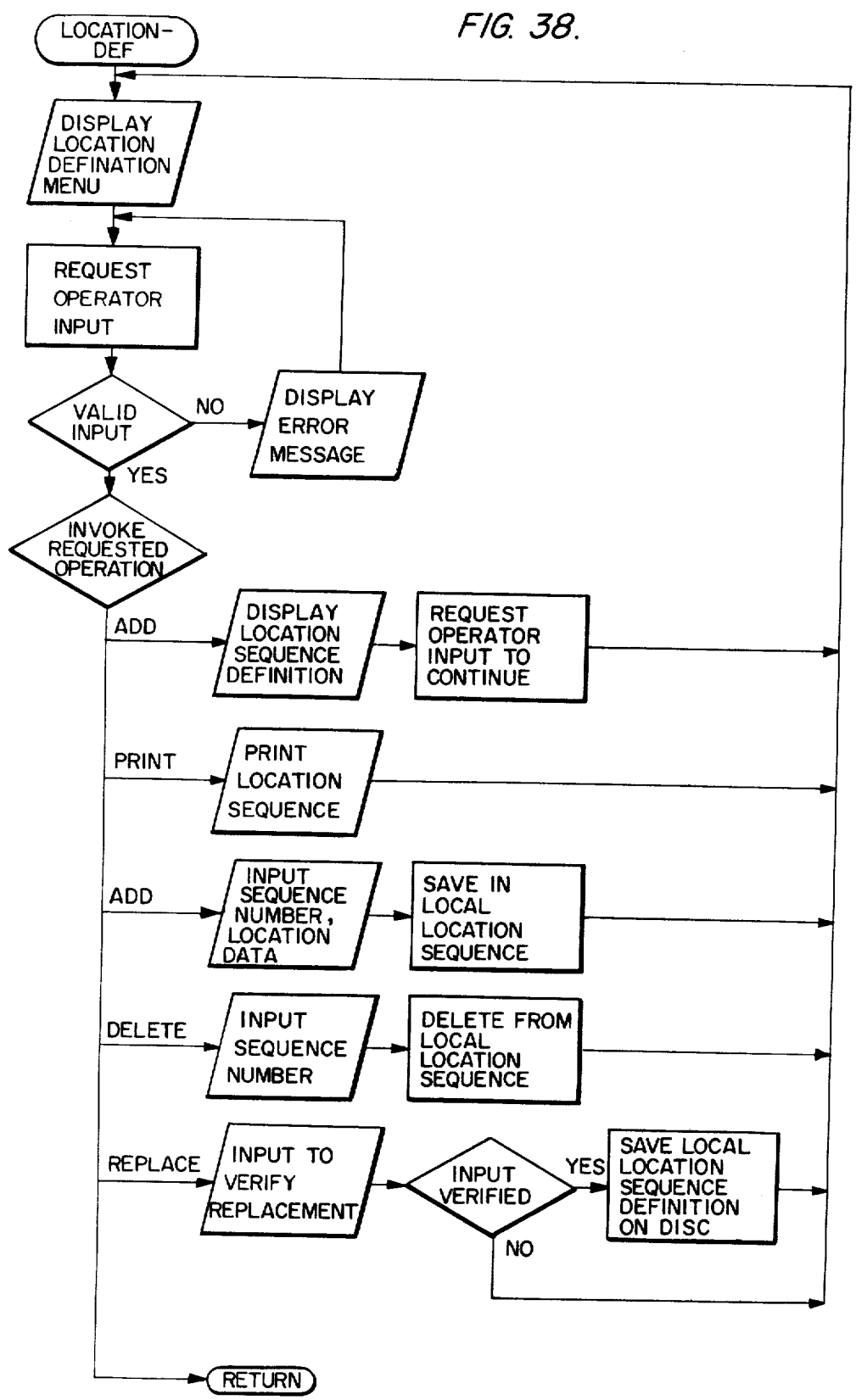
Figure 39:
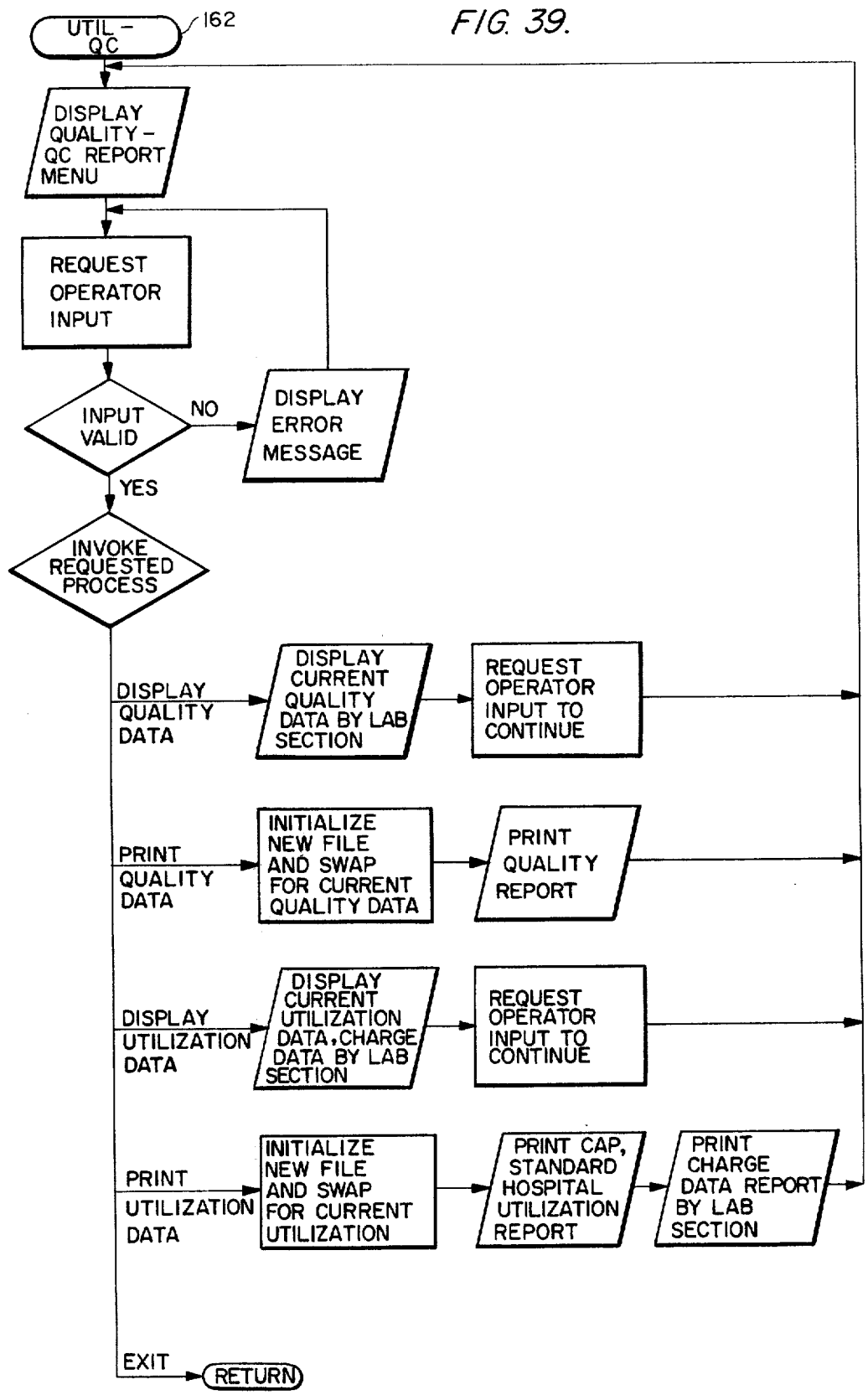

Utilization and Quality Control support processing begins at entry point UTIL-QC 162, FIG. 36, upon operator input of the associated menu selection. The purpose of this function is to automate the reporting of quality and utilization data as required to meet laboratory quality, certification and regulatory requirements.

INDUSTRIAL APPLICABILITY

The patient test data reporting system of the present invention is designed to accumulate, store and report laboratory and other diagnostic test data provided by a hospital linked or independent laboratory for a continuously changing patient population. The system is particularly suited for use in processing and reporting the test data of patients in acute and chronic care hospitals.

I claim:

1. Apparatus for generating, storing and reporting medical test data resulting from the performance of various medical tests selected from a predetermined set of known medical tests which are divisible into subsets of tests useful to patient treatment personnel in diagnosing and treating organ system related diseases, such tests being conducted on a plurality of medical patients which collectively define a continually changing patient population, said apparatus comprising (a) electronic data generating means for generating a digital electrical signal field for each test conducted on the patient population, said each field including
  (1) a first set of electrical digital signals identifying a particular medical test from the predetermined set of known medical tests,
  (2) a second set of electrical digital signals identifying the results of the test identified by said first set,
  (3) a third set of electrical digital signals identifying the date on which the test identified by said first set was conducted, and
  (4) a fourth set of electrical digital signals identifying the patient for whom the test identified by said first set was conducted;
(b) data storage means for receiving and storing all said digital electrical signal fields generated by said electronic data generating means on the entire patient population, said data storage means including a random access memory means connected with said electronic data generating means for permitting said digital electrical signal sets stored by said data storage means to be retrieved randomly in accordance with the information identified by said sets; and
(c) report generating means for generating periodically individual patient test data reports for each patient within the patient population wherein each report includes all stored test data for the particular patient for the total time period during which the patient has been a member of the patient population and wherein each report is organized to present the cumulative test data in a highly compact pattern of data packages wherein each data package includes only results of tests making up a particular organ system disease related subset of tests, said report generating means including
  (1) printing means responsive to control signals for producing the individual patient reports by converting digital electrical signals representative of the type of tests and of the dates and results of such tests into visually perceptible indicia appearing in an orthogonal pattern of rows and columns on a hard copy report,
  (2) data package formatting means for generating successive data package formatting signals to cause results of repeated performance of the same test on the same patient to appear in a single column of a single data package and to cause the results of all tests which are included in the data package and which were performed on the same patient on the same date to appear in a single row of the same data package,
  (3) report formatting means for generating an identical succession of report formatting electrical signals each time a patient report is produced by said printing means for identifying the tests and sequence of tests included in each successively formed data package and for identifying the sequence in which said data packages are to appear in each patient report, and
  (4) controller means connected with said data storage means, said printing means, said data package formatting means and said report formatting means, for generating printer control signals which cause the printing means to form a patient report for each patient within the patient population by retrieving all test data accumulated on each patient during the entire period that the patient has remained a member of the patient population and for causing the printing means to form a predetermined succession of comprehensive data packages in accordance with said report and data package formatting signals with each data package containing an orthogonal pattern of visible indicia including the results of all tests defined by the data package which were conducted on the patient during the entire period in which the patient has remained a member of the patient population and with the visible indicia in each column representing said second sets of all signal fields having identical first sets stored in said data storage means for such patient and for generating printer control signals which cause the printer to print the visible indicia in each column of each data package in chronological order as determined by said fourth set of each corresponding signal field, whereby each successively printed patient report supersedes all prior reports and includes all stored medical test results organized in a compact comprehensive organ system disease related pattern in which the order of the data packages and the order of tests appearing in each package is identical in all reports to assist patient treatment personnel to assimilate and understand organ system disease related test information in the least amount of time.

2. Apparatus as defined in claim 1, wherein said report formatting means includes label signal generating means for generating label signals representative of each type of test within the predetermined set of known medical tests and said data package formatting means includes label formatting means for generating label formatting signals to cause visible indicia identifying the type of test above each column of test results in each data package corresponding to the said first set of each signal field associated with the column, said controller means responding to said label signals and said label formatting signals to cause said printing means to form visible indicia at the top of each column in each data package identifying the type of tests which appear in the corresponding columns.

3. Apparatus as defined in claim 2, wherein said data storage means includes a patient register for recording signals representative of each patient making up the patient population and representative of the age and sex of each patient and a reference level storage register for storing reference level information signals indicating the normal range for a patient of a given sex and age for each test of the predetermined set of known medical tests and wherein said data package formatting means includes reference level formatting means for generating reference level formatting signals to cause reference levels for a patient to be displayed above each column of test results appearing in each data package, and wherein said controller means generates control signals in response to said reference level information and formatting signals for causing said printer means to print reference levels corresponding to the age and sex of the patient whose report is being printed in association with each column of test results appearing in each data package.

4. Apparatus as defined in claim 3, wherein said controller means includes a comparator means for comparing the test results represented by said second set of each signal field with the normal reference level for the age and sex of the patient whose report is being generated to produce an out of range signal for any test result which is out of the corresponding stored reference range, said controller means causing said printer means to place a visible out-of-range indicator adjacent the visible indicia appearing in the patient report which represents the out of range test result.

5. Apparatus as defined in claim 3, wherein said data storage means further includes supplemental information and threshold criteria storage means for storing information useful to a clinician in interpreting specific test results which are out of the normal range for such test, and wherein said controller means includes a comparator means for comparing the test results represented by said second set of each signal field with the stored reference level for the age and sex of the patient whose report is being generated and wherein said controller means is connected with said supplemental information and threshold criteria storage means for causing said printer means to print said stored supplemental information corresponding to a particular test whenever the results for such particular test is out of the range defined by said supplemental information and threshold criteria storage means.

6. Apparatus as defined in claim 5, wherein said supplemental information and threshold criteria storage means includes additional means for storing signals representative of information regarding alternative treatment and the current costs for each type of treatment and wherein said controller means is connected with said additional means to cause said printer means to print said alternative treatment and current cost information on the patient report in association with a particular printed test result whenever the results for such test indicate an out of range result given the age and sex of the patient as determined by said comparator means.

7. A method for generating, storing and reporting medical tests data resulting from the performance of various medical tests selected from a predetermined set of known medical tests which are divisible into subsets of tests useful to patient treatment personnel in diagnosing and treating organ systems related diseases, such tests being conducted on a plurality of medical patients which collectively define a continually changing patient population, wherein said method comprises the steps of (a) generating a digital electrical signal field for each test conducted on the patient population including generating a first set of electrical digital signals identifying a particular medical test from the predetermined set of known medical tests, generating a second set of electrical digital signals identifying the results of the test identified by said first set, generating a third set of electrical digital signals identifying the date on which the test identified by said first set was conducted, and generating a fourth set of electrical digital signals identifying the patient for whom the test identified by said first set was conducted;

(b) storing all said digital electrical signal fields generated in step (a) on the entire patient population;

(c) generating periodically individual patient test data reports for each patient within the patient population wherein each report includes all stored test data for the particular patient for the total time period during which the patient has been a member of the patient population and wherein each report is organized to present the cumulative test data in a highly compact pattern of data packages wherein each data package includes only results of tests making up a particular organ system disease related subset of tests by (1) converting digital electrical signals representative of the type of tests and of the dates and results of such tests into visually perceptible indicia appearing in an orthogonal pattern of rows and columns on a hard copy report, (2) generating successive data package formatting signals to cause results of repeated performance of the same test on the same patient to appear in a single column of a single data package and to cause the results of all tests which are included in the data package and which were performed on the same patient on the same data to appear in a single row of the same data package, (3) generating an identical succession of report formatting electrical signals each time a patient report is produced for identifying the tests and sequence of tests included in each successively formed data package and for identifying the sequence in which said data packages are to appear in each patient report, and (4) forming a patient report for each patient within the patient population by retrieving all tests data accumulated on each patient during the entire period that the patient has remained a member of the patient population and forming a predetermined succession of comprehensive data packages in accordance with said report and data package formatting signals with each data package containing an orthogonal pattern of visible indicia including the results of all tests defined by the data package which were conducted on the patient during the entire period in which the patient has remained a member of the patient population and with the visible indicia in each column representing said second sets of all signal fields having identical first sets stored in step (b) and printing the visible indicia in each column of each data package in chronological order as determined by said fourth set of each corresponding signal field, whereby each successively printed patient report supersedes all prior reports and includes all stored medical test results organized in a compact comprehensive organ system disease related pattern in which the order of the data packages and the order of tests appearing in each package is identical in all reports to assist patient treatment personnel to assimilate and understand organ system disease related test information in the least amount of time.

8. A method as defined in claim 7, further including the steps of generating label signals representative of each type of test within the predetermined set of known medical tests and generating label formatting signals to cause visible indicia identifying the type of test above each column of test results in each data package corresponding to the said first set of each signal field associated with the column, forming, in response to said label signals and said label formatting signals, visible indicia at the top of each column in each data package identifying the type of tests which appear in the corresponding columns.

9. A method as defined in claim 8, further including the steps of recording signals representative of each patient making up the patient population, recording signals representative of the age and sex of each patient, storing reference level information signals indicating the normal range for a patient of a given sex and age for each test of the predetermined set of known medical tests, generating and printing reference levels corresponding to the age and sex of the patient whose report is being printed in association with each column of test results appearing in each data package in response to the stored reference level information signals corresponding to the age and sex of the patient whose report is being generated.

10. A method as defined in claim 9, further including the steps of comparing the test results represented by said second set of each signal field with the normal reference level for the age and sex of the patient whose report is being generated to produce an out of range signal for any test result which is out of the corresponding stored reference range, and printing a visible out-of-range indicator adjacent the visible indicia appearing in the patient report which represents the out-of-range test result.

11. A method as defined in claim 9, further including the steps of storing information useful to a clinician in interpreting specific test results which are out of the normal range, comparing the test results represented by said second set of each signal field with the stored reference level for the age and sex of the patient whose report is being generated, and printing said stored supplemental information on the patient report whenever any individual test result is out of the range defined by said supplemental information and threshold criteria storage means.

12. A method as defined in claim 10, further including the step of storing signals representative of information regarding alternative treatment and the current costs for each type of treatment and printing the alternative treatment and current cost information on the patient report in association with a particular printed test result whenever the result for such test indicate an out of range level given the age and sex of the patient.

13. Apparatus for generating, storing and reporting medical test data resulting from the performance of various medical tests selected from a predetermined set of known medical tests which are divisible into subsets of tests useful to patient treatment personnel in diagnosing and treating organ system related diseases, such test being conducted on a plurality of medical patients which collectively define a continually changing patient population, said apparatus comprising (a) electronic data generating means for generating a digital electrical signal field for each test conducted on the patient population, each said field including (1) a first set of electrical digital signals identifying a particular medical test from the predetermined set of known medical tests, (2) a second set of electrical digital signals identifying the results of the test identified by said first set, (3) a third set of electrical digital signals identifying the date on which the test identified by said first set was conducted, and (4) a fourth set of electrical digital signals identifying the patient for whom the test identified by said first set was conducted;

(b) data storage means for receiving and storing all said digital electrical signal fields generated by said electronic data generating means on the entire patient population, said data storage means including a random access memory means connected with said electronic data generating means for permitting said digital electrical signal sets stored by said data storage means to be retrieved randomly in accordance with the information identified by said sets; and (c) report generating means for generating periodically individual patient test data reports for each patient within the patient population wherein each report includes all stored test data for the particular patient for the total time period during which the patient has been a member of the patient population and wherein each report is organized to present the cumulative test data in a highly compact pattern of data packages wherein each data package includes only results of tests making up a particular organ system disease related subset of tests, said report generating means including (1) image forming means responsive to control signals for producing the individual patient reports by converting digital electrical signals representative of the type of tests and of the dates and results of such tests into visually perceptible indicia appearing in an orthogonal pattern of rows and columns, (2) data package formatting means for generating successive data package formatting signals to cause results of repeated performance of the same test on the same patient to appear in a single column of a single data package and to cause the results of all tests which are included in the data package and which were performed on the same patient on the same date to appear in a single row of the same data package, (3) report formatting means for generating an identical succession of report formatting electrical signals each time a patient report is produced by said image forming means for identifying the tests and sequence of tests included in each successively formed data package and for identifying the sequence in which said data packages are to appear in each patient report, and (4) controller means connected with said data storage means, said image forming means, said data package formatting means and said report formatting means, for generating image forming control signals which cause the image forming means to form a patient report for each patient within the patient population by retrieving all tests data accumulated on each patient during the entire period that the patient has remained a member of the patient population and for causing the image forming means to form a predetermined succession of comprehensive data packages in accordance with said report and data package formatting signals with each data package containing an orthogonal pattern of visible indicia including the results of all tests defined by the data package which were conducted on the patient during the entire period in which the patient has remained a member of the patient population and with the visible indicia in each column representing said second sets of all signal fields having identical first sets stored in said data storage means for such patient and for generating image forming control signals which cause the image forming means to form the visible indicia in each column of each data package in chronological order as determined by said fourth set of each corresponding signal field, whereby each successively formed patient report supersedes all prior reports and includes all stored medical test results organized in a compact comprehensive organ system disease related pattern in which the order of the data packages and the order of tests appearing in each package is identical in all reports to assist patient treatment personnel to assimilate and understand organ system disease related test information in the least amount of time.

14. Apparatus as defined in claim 13, wherein said image forming means is a CRT.

15. Apparatus as defined in claim 13, wherein said image forming means is a high speed line printer.

16. Apparatus as defined in claim 1, wherein said report formatting means includes a Coag. data package generator for generating report formatting electrical signals which define a single data package including the following medical tests: Prothrombin Activity, Activated Partial Thromboplastin Time, Bleeding Time, Fibrinogen and Fibrin Degradation Products.

17. Apparatus as defined in claim 16, wherein said report formatting means includes a Chem II data package generator for generating report formatting electrical signals which define a single data package including the following medical tests:

Calcium, Phosphate, Uric Acid, Amylase, Lipase, Cholesterol, Triglycerides, High Density Lipoproteins and Low Density Lipoproteins.

18. Apparatus as defined in claim 17, wherein said report formatting means includes a Chem II data package generator for generating report formatting electrical signals which define a single data package including the following medical tests:

Bilirubin Total, bilirubin Direct, Serum Alkaline Phosphatase, Gamma Glutamyl Transpeptidase, Serum Glutamic Pyruvic Transaminase, Serum Glutamic Oxalacetic Transaminase, Lactate Dehydrogenase and Creatine Phosphokinase.

19. Apparatus as defined in claim 18, wherein said report formatting means includes a Misc. Hem. data package generator for generating report formatting electrical signals which define a single data package including the following medical tests:

Stool Occult Blood, Reticulocyte Count, Eosinophil Count, Erythrocyte Sedimentation Rate, Iron, Iron Binding Capacity, Ferritin, $B_{12}$ and Folate.

20. Apparatus as defined in claim 19, wherein said report formatting means includes a Chem I data package generator for generating report formatting electrical signals which define a single data package including the following medical tests:

Glucose, Blood Urea Nitrogen, Creatinine, Sodium, Potassium, Chloride, Carbon Dioxide, Osmolarity (Serum) and Osmolarity (Urine).

21. Apparatus as defined in claim 20, wherein said report formatting means includes a Coulter data package generator for generating report formatting electrical signals which define a single data package including the following medical tests:

Hemoglobin, Hematocrit, White Cell Blood Count, Platelets, Red Cell Blood Count, Mean Corpuscular Volume, Mean Corpuscular Hemoglobin, and Mean Corpuscular Hemoglobin Cencentration.

22. Apparatus as defined in claim 21, wherein said report formatting means includes a Diff(%) Morph data package generator for generating report formatting electrical signals which define a single data package including the following medical tests:

Polymorphonuclear Leukocytes, Bands, Lymphoctyes, Monocytes, Eosinophils, Basophils, Other, Red Blood Cells, and Platelets.

23. Apparatus as defined in claim 1, wherein said report formatting means includes a Chem II data package generator for generating report formatting electrical signals which define a single data package including the following medical tests:

Calcium, Phosphate, Uric Acid, Amylase, Lipase, Cholesterol, Triglycerides, High Density Lipoproteins and Low Density Lipoproteins.

24. Apparatus as defined in claim 1, wherein said report formatting means includes a Chem III data package generator for generating report formatting electrical signals which define a single data package including the following medical tests:

Bilirubin Total, Bilirubin Direct, Serum Alkaline Phosphatase, Gamma Glutamyl Transpeptidase, Serum Glutamic Pyruvic Transaminase, Serum Glutamic Oxalacetic Transaminase, Lactate Dehydrogenase and Creatine Phosphokinase.

25. Apparatus as defined in claim 1, wherein said report formatting means includes a Chem II data package generator for generating report formatting electrical signals which define a single data package including the following medical tests:

Calcium, Phosphate, Uric Acid, Amylase, Lipase, Cholesterol, Triglycerides, High Density Lipoproteins and Low Density Lipoproteins.

26. Apparatus as defined in claim 1, wherein said report formatting means includes a Misc. Hem. data package generator for generating report formatting electrical signals which define a single data package including the following medical tests:

Stool Occult Blood, Reticulocyte Count, Eosinophil Count, Erylthrocyte Sedimentation Rate, Iron, Iron Binding Capacity, Ferritin, $B_{12}$ and Folate.

27. Apparatus as defined in claim 1, wherein said report formatting means includes a Chem I data package generator for generating report formatting electrical signals which define a single data package including the following medical tests:

Glucose, Blood Urea Nitrogen, Creatinine, Sodium, Potassium, Chloride, Carbon Dioxide, Osmolarity (Serum) and Osmolarity (Urine).

28. Apparatus as defined in claim 1, wherein said report formatting means includes a Coulter data package generator for generating report formatting electrical signals which define a single data package including the following medical tests:

Hemoglobin, Hematocrit, White Cell Blood Count, Platelets, Red Cell Blood Count, Mean Corpuscular Volume, Mean Corpuscular Hemoglobin and Mean Corpuscular Hemoglobin Concentration.

29. Apparatus as defined in claim 1, wherein said report formatting means includes a Diff(%) Morph data package generator for generating report formatting electrical signals which define a single data package including the following medical tests:

Polymorphonuclear Leukocytes, Bands, Lymphocytes, Monocytes, Eosinophils, Basophils, Other, Red Blood Cells and Platelets.

30. Apparatus as defined in claim 1, wherein said report formatting means includes a Microbiology data package generator for generating report formatting electrical signals which define a signal data package including the following information: origin of the body fluid or tissue to be cultured, the presence or absence of micro-organisms as determined by microscopic examination, the identification of those microorganisms appearing in the culture, the names of antibiotic agents to which the identified organisms are sensitive, a numerical indication of the order in which the antibiotics are indicated for use against the identified micro-organisms and the cost per day of use for each of the numerically indicated antibiotic agents.

* * * * *